US007510768B2

(12) United States Patent
Crawford et al.

(10) Patent No.: US 7,510,768 B2
(45) Date of Patent: *Mar. 31, 2009

(54) THERMOPLASTIC ARTICLES COMPRISING CYCLOBUTANEDIOL HAVING A DECORATIVE MATERIAL EMBEDDED THEREIN

(75) Inventors: Emmett Dudley Crawford, Kingsport, TN (US); David Scott Porter, Blountville, TN (US); Gary Wayne Connell, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 147 days.

This patent is subject to a terminal disclaimer.

(21) Appl. No.: 11/391,642

(22) Filed: Mar. 28, 2006

(65) Prior Publication Data

US 2006/0286384 A1 Dec. 21, 2006

Related U.S. Application Data

(60) Provisional application No. 60/750,692, filed on Dec. 15, 2005, provisional application No. 60/750,693, filed on Dec. 15, 2005, provisional application No. 60/750,682, filed on Dec. 15, 2005, provisional application No. 60/750,547, filed on Dec. 15, 2005, provisional application No. 60/739,058, filed on Nov. 22, 2005, provisional application No. 60/738,869, filed on Nov. 22, 2005, provisional application No. 60/731,454, filed on Oct. 28, 2005, provisional application No. 60/731,389, filed on Oct. 28, 2005, provisional application No. 60/691,567, filed on Jun. 17, 2005.

(51) Int. Cl.
*B32B 27/36* (2006.01)
*C08G 64/00* (2006.01)

(52) U.S. Cl. .................. 428/412; 428/46; 428/111; 428/212; 428/411.1; 528/176; 528/190; 528/193; 528/194; 528/198

(58) Field of Classification Search ............ 428/46, 428/111, 212, 411, 412; 528/176, 190, 193, 528/194, 196, 198

See application file for complete search history.

(56) References Cited

U.S. PATENT DOCUMENTS

| | | | |
|---|---|---|---|
| 1,602,699 A | 10/1926 | Nightingale | |
| 2,160,841 A | 6/1939 | Dreyfus | |
| 2,202,046 A | 5/1940 | Dreyfus et al. | |
| 2,278,537 A | 4/1942 | Dreyfus et al. | |
| 2,720,507 A | 10/1955 | Caldwell | |
| 2,806,064 A | 9/1957 | McKlveen | |
| 2,901,466 A | 8/1959 | Kibler | |
| 2,936,324 A | 5/1960 | Hasek et al. | |
| 3,000,906 A | 9/1961 | Hasek et al. | |
| 3,030,335 A | 4/1962 | Goldberg | |
| 3,062,852 A | 11/1962 | Martin et al. | |
| 3,075,952 A | 1/1963 | Coover et al. | |
| 3,091,600 A | 5/1963 | Caldwell et al. | |
| 3,169,121 A | 2/1965 | Goldberg et al. | |
| 3,190,928 A | 6/1965 | Elam et al. | |
| 3,201,474 A | 8/1965 | Hasek et al. | |
| 3,207,814 A | 9/1965 | Goldberg et al. | |
| 3,227,764 A | 1/1966 | Martin et al. | |
| 3,236,899 A | 2/1966 | Clark | |
| 3,249,652 A | 5/1966 | Quisenberry | |
| 3,259,469 A | 7/1966 | Painter et al. | |
| 3,287,390 A | 11/1966 | Poos et al. | |
| 3,288,854 A | 11/1966 | Martin | |
| 3,312,741 A | 4/1967 | Martin | |
| 3,313,777 A | 4/1967 | Elam et al. | |
| 3,317,466 A | 5/1967 | Caldwell et al. | |
| 3,329,722 A | 7/1967 | Rylander | |
| 3,360,547 A | 12/1967 | Wilson et al. | |
| 3,366,689 A | 1/1968 | Maeda et al. | |
| 3,386,935 A | 6/1968 | Jackson et al. | |
| 3,403,181 A | 9/1968 | Painter et al. | |
| 3,502,620 A | 3/1970 | Caldwell | |
| 3,541,059 A | 11/1970 | Schaper | |
| 3,456,177 A | 12/1970 | Kibler et al. | |
| RE27,682 E | 6/1973 | Hermann et al. | |
| 3,772,405 A | 11/1973 | Hamb | |

(Continued)

FOREIGN PATENT DOCUMENTS

BE 615850 4/1962

(Continued)

OTHER PUBLICATIONS

Abstract of U.S. Defense Publication T869,015, 869 O.G. 714, Dec. 16, 1969.

(Continued)

*Primary Examiner*—Terressa M Boykin
(74) *Attorney, Agent, or Firm*—B. J. Boshears; Bernard J. Graves, Jr.

(57) ABSTRACT

This invention relates to thermoplastic article having one or more decorative materials embedded therein which is obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend wherein the thermoplastic article comprises at least one polyester composition comprising at least one polyester which comprises terephthalic acid and 2,2,4,4-tetramethyl-1,3-cyclobutanediol.

95 Claims, 3 Drawing Sheets

U.S. PATENT DOCUMENTS

| | | | |
|---|---|---|---|
| 3,799,953 A | 3/1974 | Freitag et al. |
| 3,907,754 A | 9/1975 | Tershansy et al. |
| 3,915,913 A | 10/1975 | Jackson, Jr. et al. |
| 3,962,189 A | 6/1976 | Russin et al. |
| 4,001,184 A | 1/1977 | Scott |
| 4,010,145 A | 3/1977 | Russin et al. |
| 4,156,069 A | 5/1979 | Prevorsek et al. |
| 4,160,383 A | 7/1979 | Rauschenberger |
| 4,185,009 A | 1/1980 | Idel et al. |
| 4,194,038 A | 3/1980 | Baker et al. |
| 4,356,299 A | 10/1982 | Cholod et al. |
| 4,367,186 A | 1/1983 | Adelmann et al. |
| 4,424,140 A | 1/1984 | Weinberg et al. |
| 4,427,614 A | 1/1984 | Barham et al. |
| 4,430,484 A | 2/1984 | Quinn |
| 4,431,793 A | 2/1984 | Rosenquist |
| 4,452,933 A | 6/1984 | McCready |
| 4,465,820 A | 8/1984 | Miller et al. |
| 4,469,861 A | 9/1984 | Mark et al. |
| 4,525,504 A | 6/1985 | Morris et al. |
| 4,749,773 A | 6/1988 | Weaver et al. |
| 4,826,903 A | 5/1989 | Weaver et al. |
| 4,845,188 A | 7/1989 | Weaver et al. |
| 4,880,592 A | 11/1989 | Martini et al. |
| 4,882,412 A | 11/1989 | Weaver et al. |
| 4,892,922 A | 1/1990 | Weaver et al. |
| 4,892,923 A | 1/1990 | Weaver et al. |
| 4,976,057 A | 12/1990 | Bianchi |
| 4,981,898 A | 1/1991 | Bassett |
| 5,017,679 A | 5/1991 | Chang et al. |
| 5,017,680 A | 5/1991 | Sublett |
| 5,104,450 A | 4/1992 | Sand et al. |
| 5,118,847 A | 6/1992 | Jackson et al. |
| 5,142,088 A | 8/1992 | Phelps et al. |
| 5,169,994 A | 12/1992 | Sumner, Jr. et al. |
| 5,183,863 A | 2/1993 | Nakamura et al. |
| 5,191,038 A | 3/1993 | Krabbenhoft et al. |
| 5,219,510 A | 6/1993 | Machell et al. |
| 5,239,020 A | 8/1993 | Morris |
| 5,256,761 A | 10/1993 | Blount, Jr. |
| 5,258,556 A | 11/1993 | Sumner, Jr. et al. |
| 5,288,715 A | 2/1994 | Machell et al. |
| 5,292,783 A | 3/1994 | Buchanan et al. |
| 5,310,787 A | 5/1994 | Kutsuwa et al. |
| 5,333,073 A | 7/1994 | Suzuki |
| 5,372,864 A | 12/1994 | Weaver et al. |
| 5,372,879 A | 12/1994 | Handa et al. |
| 5,378,796 A | 1/1995 | George et al. |
| 5,382,292 A | 1/1995 | Conroy et al. |
| 5,384,377 A | 1/1995 | Weaver et al. |
| 5,475,144 A | 12/1995 | Watson et al. |
| 5,480,926 A | 1/1996 | Fagerburg et al. |
| 5,486,562 A | 1/1996 | Borman et al. |
| 5,489,665 A | 2/1996 | Yamato et al. |
| 5,494,992 A | 2/1996 | Kanno et al. |
| 5,498,668 A | 3/1996 | Scott |
| 5,498,688 A | 3/1996 | Oshino et al. |
| 5,506,014 A | 4/1996 | Minnick |
| 5,654,347 A | 8/1997 | Khemani et al. |
| 5,656,715 A | 8/1997 | Dickerson et al. |
| 5,668,243 A | 9/1997 | Yau et al. |
| 5,681,918 A | 10/1997 | Adams et al. |
| 5,696,176 A | 12/1997 | Khemani et al. |
| 5,705,575 A | 1/1998 | Kelsey |
| 5,783,307 A | 7/1998 | Fagerburg et al. |
| 5,863,622 A | 1/1999 | Jester |
| 5,907,026 A | 5/1999 | Factor et al. |
| 5,942,585 A | 8/1999 | Scott et al. |
| 5,955,565 A | 9/1999 | Morris et al. |
| 5,958,539 A * | 9/1999 | Eckart et al. .................. 428/46 |
| 5,977,347 A | 11/1999 | Shuto et al. |
| 5,989,663 A | 11/1999 | Morris et al. |
| 6,001,910 A | 12/1999 | Blumenthal et al. |
| 6,005,059 A | 12/1999 | Scott et al. |
| 6,011,124 A | 1/2000 | Scott et al. |
| 6,022,603 A | 2/2000 | Umeda et al. |
| 6,037,424 A | 3/2000 | Scott et al. |
| 6,043,322 A | 3/2000 | Scott et al. |
| 6,096,854 A | 8/2000 | Morris et al. |
| 6,126,992 A | 10/2000 | Khanarian et al. |
| 6,146,228 A | 11/2000 | Mougin et al. |
| 6,150,494 A | 11/2000 | Wang et al. |
| 6,183,848 B1 | 2/2001 | Turner et al. |
| 6,191,209 B1 | 2/2001 | Andrews et al. |
| 6,211,309 B1 | 4/2001 | McIntosh et al. |
| 6,221,556 B1 | 4/2001 | Gallucci et al. |
| 6,225,436 B1 | 5/2001 | Eiffler et al. |
| 6,232,504 B1 | 5/2001 | Barteau et al. |
| 6,255,523 B1 | 7/2001 | Panandiker et al. |
| 6,307,006 B1 | 10/2001 | Konig et al. |
| 6,323,291 B1 | 11/2001 | Mason et al. |
| 6,323,304 B1 | 11/2001 | Lemmon et al. |
| 6,342,304 B1 | 1/2002 | Buchanan et al. |
| 6,352,783 B1 | 3/2002 | Fagerburg |
| 6,354,986 B1 | 3/2002 | Hlavinka et al. |
| 6,448,334 B1 | 9/2002 | Verhoogt et al. |
| 6,504,002 B1 | 1/2003 | Karlik et al. |
| 6,559,272 B1 | 5/2003 | Jeon et al. |
| 6,733,716 B2 | 5/2004 | Belcher |
| 6,740,377 B2 | 5/2004 | Pecorini et al. |
| 6,818,293 B1 | 11/2004 | Keep et al. |
| 6,846,440 B2 | 1/2005 | Flynn et al. |
| 6,908,650 B2 | 6/2005 | Odorisio et al. |
| 7,048,978 B2 | 5/2006 | Tanaka et al. |
| 2001/0029324 A1 | 10/2001 | Walker et al. |
| 2001/0044003 A1 | 11/2001 | Gallucci et al. |
| 2002/0055586 A1 | 5/2002 | Dalgewicz, III et al. |
| 2002/0128357 A1 | 9/2002 | Goossens et al. |
| 2002/0137856 A1 | 9/2002 | Andrews et al. |
| 2002/0198297 A1 | 12/2002 | Odorisio et al. |
| 2003/0032737 A1 | 2/2003 | Andrews et al. |
| 2003/0060546 A1 | 3/2003 | Moskala et al. |
| 2003/0075516 A1 | 4/2003 | Rothman et al. |
| 2003/0139497 A1 | 7/2003 | Odorisio et al. |
| 2003/0149177 A1 | 8/2003 | Andrews et al. |
| 2003/0169514 A1 | 9/2003 | Bourdelais et al. |
| 2003/0195295 A1 | 10/2003 | Mahood et al. |
| 2003/0221716 A1 | 12/2003 | Olson |
| 2003/0229181 A1 | 12/2003 | Hariharan et al. |
| 2004/0022526 A1 | 2/2004 | Kuno et al. |
| 2004/0101687 A1 | 5/2004 | Crawford et al. |
| 2004/0106767 A1 | 6/2004 | Simon et al. |
| 2004/0108623 A1 | 6/2004 | Deeter et al. |
| 2004/0138381 A1 | 7/2004 | Blasius et al. |
| 2004/0214984 A1 | 10/2004 | Keep et al. |
| 2005/0008885 A1 | 1/2005 | Blakely et al. |
| 2005/0072060 A1 | 4/2005 | Moncho et al. |
| 2005/0101759 A1 | 5/2005 | Odorisio et al. |
| 2005/0113556 A1 | 5/2005 | Strand et al. |
| 2005/0119359 A1 | 6/2005 | Shelby et al. |
| 2005/0124779 A1 | 6/2005 | Shelby et al. |
| 2006/0004151 A1 | 1/2006 | Shaikh et al. |
| 2006/0094858 A1 | 5/2006 | Turner et al. |
| 2006/0111481 A1 | 5/2006 | Pearson et al. |
| 2006/0146228 A1 | 7/2006 | Sogo et al. |
| 2006/0180560 A1 | 8/2006 | Robinson |
| 2006/0197246 A1 | 9/2006 | Hale et al. |
| 2006/0199904 A1 | 9/2006 | Hale et al. |
| 2006/0199919 A1 | 9/2006 | Hale et al. |
| 2006/0228507 A1 | 10/2006 | Hale et al. |
| 2006/0234073 A1 | 10/2006 | Hale et al. |
| 2006/0235167 A1 | 10/2006 | Hale et al. |
| 2006/0247388 A1 | 11/2006 | Hale et al. |

| | | |
|---|---|---|
| 2006/0270773 A1 | 11/2006 | Hale et al. |
| 2006/0270806 A1 | 11/2006 | Hale |

FOREIGN PATENT DOCUMENTS

| | | | |
|---|---|---|---|
| CA | 2035149 | A1 | 8/1991 |
| DE | 29 21 868 | A1 | 12/1980 |
| DE | 197 27 709 | A1 | 6/1997 |
| DE | 198 11 773 | A1 | 9/1999 |
| EP | 0 039 838 | A1 | 11/1981 |
| EP | 0 273 144 | A2 | 5/1987 |
| EP | 0 714 764 | A2 | 6/1996 |
| EP | 0902052 | A1 | 3/1999 |
| EP | 0 930 531 | A1 | 7/1999 |
| EP | 1 066 825 | A1 | 1/2001 |
| EP | 1 674 496 | A1 | 6/2006 |
| FR | 1291273 | | 5/1965 |
| FR | 1432471 | | 2/1966 |
| FR | 1434658 | | 2/1966 |
| FR | 2.112.400 | | 6/1972 |
| GB | 962913 | | 7/1964 |
| GB | 1041651 | | 9/1966 |
| GB | 1044015 | | 9/1966 |
| GB | 1047043 | | 11/1966 |
| GB | 1130558 | | 10/1968 |
| GB | 1278284 | | 6/1972 |
| GB | 1364732 | | 8/1974 |
| GB | 2216919 | A | 10/1989 |
| JP | 56-88440 | A | 12/1979 |
| JP | 03207743 | | 9/1991 |
| JP | 65-01040 | | 2/1994 |
| JP | 9-59371 | A | 4/1997 |
| JP | 11-222516 | | 8/1999 |
| JP | 2001-066701 | A | 8/1999 |
| JP | 2000-352620 | A | 12/2000 |
| JP | 2001-098086 | A | 4/2001 |
| JP | 2004-244497 | A | 9/2004 |
| JP | 2004-292558 | A | 10/2004 |
| KR | 2001 0089942 | | 10/2001 |
| KR | 2003/054611 | | 7/2003 |
| WO | WO 01/06981 | | 2/2001 |
| WO | 0185824 | A2 | 11/2001 |
| WO | WO 02/059207 | A2 | 8/2002 |
| WO | WO 2004/106988 | A2 | 12/2004 |
| WO | 2005007735 | A2 | 1/2005 |
| WO | WO 2006/127755 | A2 | 11/2006 |
| WO | WO 2006/127831 | A1 | 11/2006 |
| WO | 2007/053550 | A1 | 5/2007 |
| WO | 2007053549 | A1 | 5/2007 |
| WO | WO 2007/053434 | A1 | 5/2007 |
| WO | WO 2007/053548 | A2 | 5/2007 |

OTHER PUBLICATIONS

Abstract of U.S. Defense Publication T875,010, 875 O.G. 342, Jun. 9, 1970.
Chen et al., "The molecular basis for the relationship between the secondary relaxation and mechanical properties of a series of polyester copolymer glasses," Marcromolecules, 32:5944-5955 (1999).
English language Abstract of JP 02-305816 from Patent Abstracts of Japan, Dec. 19, 1990.
English language translation Belgian Patent No. BE 615,850, Apr. 13, 1962.
English language translation of French Patent No. FR 1,432,471, Feb. 7, 1966.
English language translation of French Patent No. FR 1,434,658, Feb. 28, 1966.
U.S. Appl. No. 11/390,555, filed Mar. 28, 2006, Emmett Dudley Crawford, et al.
U.S. Appl. No. 11/390,563, filed Mar. 28, 2006, Emmett Dudley Crawford, et al.
U.S. Appl. No. 11/390,629, filed Mar. 28, 2006, Emmett Dudley Crawford, et al.
U.S. Appl. No. 11/390,630, filed Mar. 28, 2006, Emmett Dudley Crawford, et al.
U.S. Appl. No. 11/390,631, filed Mar. 28, 2006, Emmett Dudley Crawford, et al.
U.S. Appl. No. 11/390,654, filed Mar. 28, 2006, Emmett Dudley Crawford, et al.
U.S. Appl. No. 11/390,655, filed Mar. 28, 2006, Emmett Dudley Crawford, et al.
U.S. Appl. No. 11/390,671, filed Mar. 28, 2006, Emmett Dudley Crawford, et al.
U.S. Appl. No. 11/390,672, filed Mar. 28, 2006, Emmett Dudley Crawford, et al.
U.S. Appl. No. 11/390,722, filed Mar. 28, 2006, Emmett Dudley Crawford, et al.
U.S. Appl. No. 11/390,750, filed Mar. 28, 2006, Emmett Dudley Crawford, et al.
U.S. Appl. No. 11/390,751, filed Mar. 28, 2006, Emmett Dudley Crawford, et al.
U.S. Appl. No. 11/390,752, filed Mar. 28, 2006, Emmett Dudley Crawford, et al.
U.S. Appl. No. 11/390,773, filed Mar. 28, 2006, Emmett Dudley Crawford, et al.
U.S. Appl. No. 11/390,793, filed Mar. 28, 2006, Emmett Dudley Crawford, et al.
U.S. Appl. No. 11/390,794, filed Mar. 28, 2006, Emmett Dudley Crawford, et al.
U.S. Appl. No. 11/390,809, filed Mar. 28, 2006, Wesley Raymond Hale, et al.
U.S. Appl. No. 11/390,811, filed Mar. 28, 2006, Emmett Dudley Crawford, et al.
U.S. Appl. No. 11/390,812, filed Mar. 28, 2006, Wesley Raymond Hale, et al.
U.S. Appl. No. 11/390,814, filed Mar. 28, 2006, Emmett Dudley Crawford, et al.
U.S. Appl. No. 11/390,826, filed Mar. 28, 2006, Emmett Dudley Crawford, et al.
U.S. Appl. No. 11/390,827, filed Mar. 28, 2006, Emmett Dudley Crawford, et al.
U.S. Appl. No. 11/390,836, filed Mar. 28, 2006, Emmett Dudley Crawford, et al.
U.S. Appl. No. 11/390,846, filed Mar. 28, 2006, Wesley Raymond Hale, et al.
U.S. Appl. No. 11/390,847, filed Mar. 28, 2006, Emmett Dudley Crawford, et al.
U.S. Appl. No. 11/390,853, filed Mar. 28, 2006, Emmett Dudley Crawford, et al.
U.S. Appl. No. 11/390,858, filed Mar. 28, 2006, Emmett Dudley Crawford, et al.
U.S. Appl. No. 11/390,864, filed Mar. 28, 2006, Wesley Raymond Hale, et al.
U.S. Appl. No. 11/390,865, filed Mar. 28, 2006, Emmett Dudley Crawford, et al.
U.S. Appl. No. 11/390,882, filed Mar. 28, 2006, Emmett Dudley Crawford, et al.
U.S. Appl. No. 11/390,883, filed Mar. 28, 2006, Thomas Joseph Pecorini, et al.
U.S. Appl. No. 11/390,908, filed Mar. 28, 2006, Wesley Raymond Hale, et al.
U.S. Appl. No. 11/391,063, filed Mar. 28, 2006, Emmett Dudley Crawford, et al.
U.S. Appl. No. 11/391,124, filed Mar. 28, 2006, Wesley Raymond Hale, et al.
U.S. Appl. No. 11/391,125, filed Mar. 28, 2006, Emmett Dudley Crawford, et al.
U.S. Appl. No. 11/391,137, filed Mar. 28, 2006, Emmett Dudley Crawford, et al.
U.S. Appl. No. 11/391,156, filed Mar. 28, 2006, Emmett Dudley Crawford, et al.
U.S. Appl. No. 11/391,485, filed Mar. 28, 2006, Emmett Dudley Crawford, et al.
U.S. Appl. No. 11/391,495, filed Mar. 28, 2006, Emmett Dudley Crawford, et al.

U.S. Appl. No. 11/391,505, filed Mar. 28, 2006, Emmett Dudley Crawford, et al.
U.S. Appl. No. 11/391,565, filed Mar. 28, 2006, Emmett Dudley Crawford, et al.
U.S. Appl. No. 11/391,571, filed Mar. 28, 2006, Emmett Dudley Crawford, et al.
U.S. Appl. No. 11/391,576, filed Mar. 28, 2006, Emmett Dudley Crawford, et al.
U.S. Appl. No. 11/391,659, filed Mar. 28, 2006, Emmett Dudley Crawford, et al.
Kelsey: Macromolecules, vol. 33, 2000, pp. 5810-5818.
Copending U.S. Appl. No. 11/588,524, filed Oct. 27, 2006, Emmett Dudley Crawford, et al.
Copending U.S. Appl. No. 11/588,458, filed Oct. 27, 2006, Emmett Dudley Crawford, et al.
Copending U.S. Appl. No. 11/588,907, filed Oct. 27, 2006, Emmett Dudley Crawford, et al.
Copending U.S. Appl. No. 11/588,527, filed Oct. 27, 2006, Emmett Dudley Crawford, et al.
Copending U.S. Appl. No. 11/588,906, filed Oct. 27, 2006, Ted Calvin Germroth, et al.
Copending U.S. Appl. No. 11/588,893, filed Oct. 27, 2006, Ted Calvin Germroth, et al.
Copending U.S. Appl. No. 11/588,554, filed Oct. 27, 2006, Emmett Dudley Crawford, et al.
U.S. Appl. No. 11/635,434, filed Dec. 7, 2006, Emmett Dudley Crawford.
U.S. Appl. No. 11/635,433, filed Dec. 7, 2006, Emmett Dudley Crawford.
Chapter 4—*Processing of Plastics in "Plastics Engineering, 3rd ed"*, R.J. Crawford, Butterworth-Heinemann Publisher, 1998, Oxford, England, pp. 245-342.
Fox equation (T.G. Fox, Session J, Bull. Am. Phys. Soc., 1, 123 (1956)).
*The Technology of Plasticizers*, by J. Kern Sears and Joseph R Darby, published by Society of Plastic Engineers/Wiley and Sons, New York, 1982; pp. 136-139.
Coleman et al., "Polymer Reviews—A Practical Guide to Polymer Miscibility," *Polymer 31*, pp. 1187-1203 (1990).
"*Hansen Solubility Parameters, a Users Handbook*", by Charles M. Hansen, Chapter 1, CRC Press, 2000, pp. 1-24.
Martinez et al., "*Phase Behavior and Mechanical Properties of Injection Molded Poly (Ethylene Terephthalate) / Polyarylate Blends*"; Journal of Applied Polymer Science, John Wiley and Sons Inc. New York, US, vol. 45, No. 7, Jul. 5, 1992, p. 1135-1143.
Won Ho Jo et al. : :*Miscibility of poly(ether imide)/poly(ethylene terephthalate) blends*; Polymer Bulletin, Springer, Heidelberg, DE, vol. 33, No. 1, Jun. 1, 1994, p. 113-118 (1994).
Anonymous: "*Poly (ethylene naphthalenedicarboxylate)/polyetherimide blends*" Research Disclosure, Mason Publications, Hampshire, GB, vol. 283, No. 38, Nov. 1987.
ASTM D1525-06, *Standard Test Method for Vicat Softening Temperature of Plastics*, Mar. 15, 2006.
ASTM D648-06, *Standard Test Method for Deflection Temperature of Plastics Under Flexural Load in the Edgewise Position*, Mar. 15, 2006.
ASTM D256-06, *Standard Test Methods for Determining the Izod Pendulum Impact Resistance of Plastics*, Mar. 15, 2006.
ASTM D790-03, *Standard Test Methods for Flexural Properties of Unreinforced and Reinforced Plastics and Electrical Insulating Materials*, Mar. 10, 2003.
ASTM D638-03, *Standard Test Method for Tensile Properties of Plastics*, Dec. 1, 2003.
ASTM D3418-03, *Transition Temperatures and Enthalpies of Fusion and Crystallization of Polymers by Differential Scanning Calorimetry*, Dec. 1, 2003.
Bergen, R.L., Jr., "Stress Cracking of Rigid Thermoplastics,"SPE Journal, Jun. 1962.
C.I. Constitution No. 515240.
C.I. Constitution No. 515245.
Database WPI, Section Ch, Week 200536, Derwent Publications Ltd., London, GB; AN 2005-355258, XP002396922 & WO 2005-030833 A1 (Kanebo Ltd) Apr. 7, 2005 abstract.
"Plastic Additives Handbook," 5th Edition, 2001, pp. 98-108 and pp. 109-112 (Hanser Gardner Publications, Inc., Cincinnati, OH).
Shearer, N.H., "T18-Type 1 Polyesters," Mar. 1996, SPE Annual Technical Conference and Exhibition, XP009080224.
U.S. Appl. No. 11/439,062, filed May 23, 2006, Wesley Raymond Hale, et al.
U.S. Appl. No. 11/439,340, filed May 23, 2006, Wesley Raymond Hale, et al.
U.S. Appl. No. 11/706,476, filed Feb. 14, 2007, Leslie Shane Moody, et al.
U.S. Appl. No. 11/706,791, filed Feb. 14, 2007, Leslie Shane Moody, et al.
Gachter, Muller, "Taschenbuch der Kunststoff-Additive," 1990, Carl Hanser Verlag Munchen Wien, XP002450422, pp. 96-97.
Gachter, Muller, "Kunststoff-Additive," 1990, Carl Hanser Verlag Munchen Wien, XP002449987, pp. 96-99.
Brown, R., "Taschenbuch Kunststoff-Additive," 1990, Carl Hanser Verlag Munchen Wiel, XP002455247, pp. 361-363.
USPTO Office Action dated Apr. 15, 2008 for copending U.S. Appl. No. 11/390,629.
USPTO Office Action dated Mar. 24, 2008 for copending U.S. Appl. No. 11/390,908.
USPTO Office Action dated Apr. 16, 2008 for copending U.S. Appl. No. 11/390,751.
USPTO Office Action dated Apr. 17, 2008 for copending U.S. Appl. No. 11/390,814.
U.S. Appl. No. 11/827,696, filed Jul. 13, 2007, Ryan Thomas Neill, et al.
U.S. Appl. No. 12/091,568, filed Apr. 25, 2008, Emmett Dudley Crawford, et al.
U.S. Appl. No. 12/091,566, filed Apr. 25, 2008, Emmett Dudley Crawford, et al.
U.S. Appl. No. 12/091,570, filed Apr. 25, 2008, Ted Calvin Germroth, et al.
U.S. Appl. No. 12/091,572, filed Apr. 25, 2008, Ted Calvin Germroth, et al.
USPTO Office Action dated Jun. 3, 2008 for copending U.S. Appl. No. 11/391,063.
Copending application, U.S. Appl. No. 12/294,690, filed Sep. 26, 2008, Ted Calvin Germroth et al.
Copending application, U.S. Appl. No. 12/294,686, filed Sep. 26, 2008, Ted Calvin Germroth et al.
USPTO Office Action dated Sep. 10, 2008 for copending U.S. Appl. No. 11/390,752.
USPTO Office Action dated Sep. 10, 2008 for copending U.S. Appl. No. 11/390,794.
USPTO Office Action dated Sep. 19, 2008 for copending U.S. Appl. No. 11/391,565.
USPTO Office Action dated Oct. 2, 2008 for copending U.S. Appl. No. 11/390,671.
USPTO Office Action dated Sep. 24, 2008 for copending U.S. Appl. No. 11/390,631.
USPTO Office Action dated Oct. 1, 2008 for copending U.S. Appl. No. 11/390,655.
USPTO Office Action dated Sep. 29, 2008 for copending U.S. Appl. No. 11/391,137.
USPTO Office Action dated Sep. 9, 2008 for copending U.S. Appl. No. 11/391,571.
Copending application, U.S. Appl. No. 12/254,894, filed Oct. 21, 2008, Gary Michael Stack, et al.
USPTO Office Action dated Oct. 22, 2008 for copending U.S. Appl. No. 11/391,125.
USPTO Office Action dated Oct. 20, 2008 for copending U.S. Appl. No. 11/390,672.
USPTO Office Action dated Oct. 8, 2008 for copending U.S. Appl. No. 11/390,853.
USPTO Office Action dated Oct. 9, 2008 for copending U.S. Appl. No. 11/391,505.
USPTO Notice of Allowance dated Oct. 7, 2008 for copending U.S. Appl. No. 11/390,908.
USPTO Office Action dated Oct. 14, 2008 for copending U.S. Appl. No. 11/390,811.

USPTO Office Action dated Oct. 22, 2008 for copending U.S. Appl. No. 11/390,750.

USPTO Office Action dated Oct. 22, 2008 for copending U.S. Appl. No. 11/390,865.

USPTO Office Action dated Oct. 14, 2008 for copending U.S. Appl. No. 11/390,654.

USPTO Office Action dated Oct. 20, 2008 for copending U.S. Appl. No. 11/390,836.

USPTO Office Action dated Oct. 29, 2008 for copending U.S. Appl. No. 11/390,955.

USPTO Office Action dated Nov. 3, 2008 for copending U.S. Appl. No. 11/390,883.

USPTO Office Action dated Oct. 29, 2008 for copending U.S. Appl. No. 11/390,864.

USPTO Office Action dated Nov. 3, 2008 for copending U.S. Appl. No. 11/391,485.

USPTO Office Action dated Oct. 31, 2008 for copending U.S. Appl. No. 11/391,156.

USPTO Office Action dated Oct. 30, 2008 for copending U.S. Appl. No. 11/391,495.

* cited by examiner

THE EFFECT OF COMONOMER ON
THE FASTEST CRYSTALLIZATION
HALFTIMES OF MODIFIED PCT COPOLYESTERS

THE EFFECT OF COMONOMER ON
THE BRITTLE-TO-DUCTILE TRANSITION
TEMPERATURE ($T_{bd}$) IN A NOTCHED IZOD TEST
(ASTM D256, 1/8 IN THICK, 10 MIL NOTCH)

THE EFFECT OF 2,2,4,4-TETRAMETHYL-1,3-CYCLOBUTANEDIOL COMPOSITION ON THE GLASS TRANSITION TEMPERATURE ($T_g$) OF THE COPOLYESTER

THERMOPLASTIC ARTICLES COMPRISING CYCLOBUTANEDIOL HAVING A DECORATIVE MATERIAL EMBEDDED THEREIN

CROSS-REFERENCES TO RELATED APPLICATIONS

This application is related to: U.S. Provisional Application Ser. No. 60/691,567 filed on Jun. 17, 2005, U.S. Provisional Application Ser. No. 60/731,454 filed on Oct. 28, 2005, U.S. Provisional Application Ser. No. 60/731,389, filed on Oct. 28, 2005, U.S. Provisional Application Ser. No. 60/739,058, filed on Nov. 22, 2005, and U.S. Provisional Application Ser. No. 60/738,869, filed on Nov. 22, 2005, U.S. Provisional Application Ser. No. 60/750,692 filed on Dec. 15, 2005, U.S. Provisional Application Ser. No. 60/750,693, filed on Dec. 15, 2005, U.S. Provisional Application Ser. No. 60/750,682, filed on Dec. 15, 2005, and U.S. Provisional Application Ser. No. 60/750,547, filed on Dec. 15, 2005, all of which are hereby incorporated by this reference in their entireties.

FIELD OF THE INVENTION

This invention pertains to a novel thermoplastic article having decorative materials embedded therein. More specifically, this invention pertains to an article produced by applying heat and pressure to a laminate comprising, in order: an upper sheet material, at least one decorative material, for example, a fabric, metallic wire, paper, or printed layer, and a lower sheet material to produce a thermoplastic article having the decorative materials embedded therein. The thermoplastic article comprises at least one polyester composition comprising at least one polyester which comprises terephthalic acid, 2,2,4,4-tetramethyl-1,3-cyclobutanediol, and 1,4-cyclohexanedimethanol. The novel thermoplastic articles provided by the present invention may be used in the construction industry as glazing for windows, in partitions and as decorative panels. One or both surfaces of the articles may be textured during or after formation of the articles.

BACKGROUND OF THE INVENTION

Glass, both transparent and translucent, has been used as glazing material for windows and partitions and, for certain uses, it is painted or stained to provide specific decorative effects. Glass is high in density and weight, is difficult to fabricate at the work site, is generally brittle, and can constitute a safety hazard.

Glass substitutes such as polyvinyl chloride sheeting, acrylic, e.g., poly(methyl methacrylate), sheeting and polycarbonate sheeting have been used as substitutes for glass in certain glazing applications. Generally, these substitutes are made for clear (transparent), non-decorative applications. The sheet material provided by this invention may be used primarily for producing or obtaining decorative applications with varying degrees of transparency and various levels of enhanced security.

Articles made from copolyester sheet are described in U.S. Pat. Nos. 5,894,04, 5,958,539, 5,998,028, 5,643,666, and 6,025,069. However, applications exist whereby higher creep/thermal resistances compared to neat copolyester are needed, for instance backlit paneling. In addition, replacing neat copolyester with neat polycarbonate is undesirable as well, since polycarbonate has to be dried prior to composite fabrication thereby increasing cycle time and cost. Polycarbonate also must be laminated at high temperatures, which can cause degradation of the decorative layer. Further, polycarbonate is difficult to post-form without pre-drying and requires higher forming temperatures.

U.S. Pat. No. 5,413,870 describes a sturdy wall covering especially useful in a bathroom or shower area, the wall covering being comprised of a laminate that includes a clear or transparent acrylic cast in the first layer, a clear polyester thermoset resin in the second layer, and a thin fabric sheet as the third layer and a pigmented polyester thermoset coating over the fabric layer. The polyester thermosetting resins in this case are applied as a liquid and subsequently cured as a solid. There are several difficulties when using polyester thermosetting resins. Removing air bubbles from the liquid thermosetting resins can be difficult. Thermosetting resins can undergo significant shrinkage during curing. In addition, crosslinked polyester resins are known to be brittle. This invention alleviates many of these difficulties.

Polymers containing 2,2,4,4-tetramethyl-1,3-cyclobutanediol have also been generally described in the art. Generally, however, these polymers exhibit high inherent viscosities, high melt viscosities and/or high Tgs (glass transition temperatures) such that the equipment used in industry is insufficient to manufacture or post polymerization process these materials. As a result, polymers containing this monomer are not believed to be produced in commercial amounts in the industry.

Advantages of this invention over the prior art include higher heat deflection temperature (HDT), increased stiffness and increased creep resistance with time.

SUMMARY OF THE INVENTION

The present invention generally provides a thermoplastic article, typically in the form of sheet material, having a decorative material embedded therein. The thermoplastic article is obtained by applying heat and pressure to one or more laminates or "sandwiches", wherein at least one of said laminates comprises, in order, (1) at least one upper sheet material, (2) at least one decorative material, and (3) at least one lower sheet material. Optionally, an adhesive layer may be used between (1) and (2) and/or between (2) and (3).

The upper and lower sheet materials are produced from miscible polyester/polycarbonate blends. The polyester component, as described below, in certain embodiments preferably comprises a minimum level of 1,4 cyclohexanedimethanol as a comonomer in order to effect miscibility with polycarbonate and a minimum level of a 1,3-cylcobutanediol.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:

(a) 1 to 99 weight % of a polyester comprising a dicarboxylic acid component comprising:

i) from about 70 to 100 mole % of terephthalic acid residues;

ii) 0 to about 30 mole % of an aromatic dicarboxylic residues having up to 20 carbon atoms; and iii) 0 to about 10 mole % of an aliphatic dicarboxylic acid residues having up to 16 carbon atoms; and a glycol component comprising:
  i) greater than 20 to 99 mole % of 2,2,4,4-tetramethyl-1,3-cyclobutanediol residues; and
  ii) about 1 to less than 80 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.
(b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:
(a) 1 to 99 weight % of a polyester comprising a dicarboxylic acid component comprising:
i) from about 70 to 100 mole % of terephthalic acid residues;
ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and
a glycol component comprising:
i) 21 to 99 mole % of 2,2,4,4-tetramethyl-1,3-cyclobutanediol residues; and
ii) about 1 to less than 79 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C. and
(b) 99 to 1 weight % of an aromatic polycarbonate;

wherein the total combined weight percentage of polyester and polycarbonate in the polyester/polycarbonate blend equals 100 weight %.

Another embodiment of the present provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:
(a) 1 to 99 weight % of a polyester comprising
(1) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and (2) a glycol component comprising:
  i) about 25 to 75 mole % of 2,2,4,4-tetramethyl-1,3-cyclobutanediol residues; and
  ii) about 75 to about 25 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C. and
(b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:
(a) 1 to 99 weight % of a polyester comprising
(1) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and
(2) a glycol component comprising:
  i) about 30 to about 70 mole % of 2,2,4,4-tetramethyl-1,3-cyclobutanediol residues; and
  ii) about 70 to about 30 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.
(b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:
(a) 1 to 99 weight % of a polyester comprising
(1) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and iii) 0 to about 10 mole % of an aliphatic dicarboxylic acid residues having up to 16 carbon atoms; and (2) a glycol component comprising:
  i) about 35 to 65 mole % of 2,2,4,4-tetramethyl-1,3-cyclobutanediol residues; and
  ii) about 65 to about 35 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C. and (b) 99 to 1 weight % of an aromatic polycarbonate;

wherein the total combined weight percentage of polyester and polycarbonate in the polyester/polycarbonate blend equals 100 weight %.

Another embodiment of the present provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:

(a) 1 to 99 weight % of a polyester comprising
(1) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and
(2) a glycol component comprising:
  i) about 40 to about 69 mole % of 2,2,4,4-tetramethyl-1,3-cyclobutanediol residues; and
  ii) about 40 to about 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C., and (b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:

(a) 1 to 99 weight % of a polyester comprising
(1) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and
(2) a glycol component comprising:
  i) greater than 20 to less than 50 mole % of 2,2,4,4-tetramethyl-1,3-cyclobutanediol residues; and
  ii) greater than 50 to less than 80 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C. and (b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:

(a) 1 to 99 weight % of a polyester comprising
(1) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and
(2) a glycol component comprising:
  i) greater than 20 to 30 mole % of 2,2,4,4-tetramethyl-1,3-cyclobutanediol residues; and
  ii) about 70 to less than 80 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C., and (b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:

(a) 1 to 99 weight % of a polyester comprising
(1) a dicarboxylic acid component comprising:
   i) from about 70 to 100 mole % of terephthalic acid residues;
   ii) 0 to about 30 mole % of an aromatic dicarboxylic acid residues having up to 20 carbon atoms; and
   iii) 0 to about 10 mole % of an aliphatic dicarboxylic acid residues having up to 16 carbon atoms; and
(2) a glycol component comprising:
   i) about 21 to about 50 mole % of 2,2,4,4-tetramethyl-1,3-cyclobutanediol residues; and
   ii) about 50 to less than 79 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C., and (b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester/aromatic polycarbonate blend, comprising:
(a) 1 to 99 weight % of a polyester comprising
(1) a dicarboxylic acid component comprising:
   i) from about 70 to 100 mole % of terephthalic acid residues;
   ii) 0 to about 30 mole % of an aromatic dicarboxylic acid residues having up to 20 carbon atoms; and
   iii) 0 to about 10 mole % of an aliphatic dicarboxylic acid residues having up to 16 carbon atoms; and
(2) a glycol component comprising:
   i) greater than 20 to 98.99 mole % of 2,2,4,4-tetramethyl-1,3-cyclobutanediol residues;
   ii) about 0.01 to less than 80 mole % of 1,4-cyclohexanedimethanol residues, and iii) about 0.01 to less than 15 mole % ethylene glycol;

wherein the total mole % of the dicarboxylic acid component is 100 mole %, and the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.,
(b) 99 to 1 weight % of an aromatic polycarbonate;

wherein the total combined weight percentage of polyester and polycarbonate in the polyester/polycarbonate blend equals 100 weight %.

One embodiment of the present invention provides a thermoplastic article having one or more decorative materials embedded therein comprising: at least one polyester which comprises:

(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 14 to 25 mole % of 2,2,4,4-tetramethyl-1,3-cyclobutanediol residues; and
   ii) 75 to 86 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is 0.75 dL/g or less as determined in 60/40 (wt/wt) phenol/tetrachloroethane at a concentration of 0.5 g/100 ml at 25° C.

One embodiment of the present invention provides a thermoplastic article having one or more decorative materials embedded therein comprising: at least one polyester which comprises:

(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 14 to 25 mole % of 2,2,4,4-tetramethyl-1,3-cyclobutanediol residues; and
   ii) 75 to 86 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is 0.35 to 0.75 dL/g as determined in 60/40 (wt/wt) phenol/tetrachloroethane at a concentration of 0.5 g/100 ml at 25° C.

One embodiment of the present invention provides a thermoplastic article having one or more decorative materials embedded therein comprising: at least one polyester which comprises:

(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 14 to 25 mole % of 2,2,4,4-tetramethyl-1,3-cyclobutanediol residues; and
   ii) 75 to 86 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is 0.50 to 0.75 dL/g as determined in 60/40 (wt/wt) phenol/tetrachloroethane at a concentration of 0.5 g/100 ml at 25° C.

One embodiment of the present invention provides a thermoplastic article having one or more decorative materials embedded therein comprising: at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms;
(b) a glycol component comprising:
  i) 14 to 25 mole % of 2,2,4,4-tetramethyl-1,3-cyclobutanediol residues; and
  ii) 75 to 86 mole % of 1,4-cyclohexanedimethanol residues; and
(c) residues from at least one branching agent;

wherein the total mole % of said dicarboxylic acid component is 100 mole %, and the total mole % of said glycol component is 100 mole %; and wherein the inherent viscosity of said polyester is 0.5 to 1.2 dL/g as determined in 60/40 (wt/wt) phenol/tetrachloroethane at a concentration of 0.5 g/100 ml at 25° C.

One embodiment of the present invention provides a A thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 17 to 23 mole % of 2,2,4,4-tetramethyl-1,3-cyclobutanediol residues; and
    ii) 77 to 83 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.60 to less than 0.72 dL/g as determined in 60/40 (wt/wt) phenol/tetrachloroethane at a concentration of 0.5 g/100 ml at 25° C.;

wherein the glass transition temperature of said polyester is from 95 to 115° C.

One embodiment of the present invention provides a A thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 14 to 25 mole % of 2,2,4,4-tetramethyl-1,3-cyclobutanediol residues;
    ii) 75 to 86 mole % of 1,4-cyclohexanedimethanol residues, and
    iii) 0.1 to less than 10 mole % of ethylene glycol residues;

wherein the total mole % of said dicarboxylic acid component is 100 mole %, and the total mole % of said glycol component is 100 mole %;

wherein the inherent viscosity of said polyester is from 0.60 to 0.72 dL/g as determined in 60/40 (wt/wt) phenol/tetrachloroethane at a concentration of 0.5 g/100 ml at 25° C.; and wherein the glass transition temperature of said polyester is from 95 to 115° C.

One embodiment of the present invention provides a A thermoplastic article having one or more decorative materials embedded therein comprising: at least one polyester which comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 17 to 23 mole % of 2,2,4,4-tetramethyl-1,3-cyclobutanediol residues;
    (ii) 77 to 82.99 mole % of 1,4-cyclohexanedimethanol residues, and
    (iii) 0.01 to less than 15 mole % of ethylene glycol residues;

wherein the total mole % of said dicarboxylic acid component is 100 mole %, and the total mole % of said glycol component is 100 mole %;

wherein the inherent viscosity of said polyester is from 0.35 to 0.75 dL/g as determined in 60/40 (wt/wt) phenol/tetrachloroethane at a concentration of 0.5 g/100 ml at 25° C.

One embodiment of the present invention provides a thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 14 to 25 mole % of 2,2,4,4-tetramethyl-1,3-cyclobutanediol residues; and
    ii) 75 to 86 mole % of 1,4-cyclohexanedimethanol residues;

wherein the total mole % of said dicarboxylic acid component is 100 mole %, and the total mole % of said glycol component is 100 mole %;

wherein the inherent viscosity of said polyester is 0.75 dL/g or less as determined in 60/40 (wt/wt) phenol/tetrachloroethane at a concentration of 0.5 g/100 ml at 25° C.; and wherein the glass transition temperature of said polyester is from 95 to 115° C.

One embodiment of the present invention provides a thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and (b) a glycol component comprising:
  i) 14 to 25 mole % of 2,2,4,4-tetramethyl-1,3-cyclobutanediol residues; and
  ii) 75 to 86 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is 0.5 to 1.2 dL/g as determined in 60/40 (wt/wt) phenol/tetrachloroethane at a concentration of 0.5 g/100 ml at 25° C.

One embodiment of the present invention provides a thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 14 to 25 mole % of 2,2,4,4-tetramethyl-1,3-cyclobutanediol residues; and
    ii) 75 to 86 mole % of 1,4-cyclohexanedimethanol residues;

wherein the total mole % of said dicarboxylic acid component is 100 mole %, and the total mole % of said glycol component is 100 mole %;

wherein the inherent viscosity of said polyester is 0.35 to 0.75 dL/g as determined in 60/40 (wt/wt) phenol/tetrachloroethane at a concentration of 0.5 g/100 ml at 25° C.; and wherein the glass transition temperature of said polyester is from 95 to 115° C.

One embodiment of the present invention provides a thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 40 to 65 mole % of 2,2,4,4-tetramethyl-1,3-cyclobutanediol residues; and
    ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.5 to 0.68 dL/g as determined in 60/40 (wt/wt) phenol/tetrachloroethane at a concentration of 0.5 g/100 ml at 25° C.

One embodiment of the present invention provides a thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 40 to 65 mole % of 2,2,4,4-tetramethyl-1,3-cyclobutanediol residues; and
    ii) 35 to 60 mole % of 1,4-cyclohexanedimethanol residues;

wherein the total mole % of said dicarboxylic acid component is 100 mole %, and the total mole % of said glycol component is 100 mole %;

wherein the inherent viscosity of said polyester is 0.68 dL/g or less as determined in 60/40 (wt/wt) phenol/tetrachloroethane at a concentration of 0.5 g/100 ml at 25° C.; and optionally, wherein one or more branching agents is added prior to or during the polymerization of said polyester.

One embodiment of the present invention provides a thermoplastic article having one or more decorative materials embedded therein comprising: at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 40 to 65 mole % of 2,2,4,4-tetramethyl-1,3-cyclobutanediol residues; and
    ii) 35 to 60 mole % of 1,4-cyclohexanedimethanol residues, and
  (c) residues of at least one branching agent;

wherein the total mole % of said dicarboxylic acid component is 100 mole %, and the total mole % of said glycol component is 100 mole %; and wherein the inherent viscosity of said polyester is from 0.5 to 1.2 dL/g as determined in 60/40 (wt/wt) phenol/tetrachloroethane at a concentration of 0.5 g/100 ml at 25° C.

One embodiment of the present invention provides a thermoplastic article having one or more decorative materials embedded therein comprising:
at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 40 to 65 mole % of 2,2,4,4-tetramethyl-1,3-cyclobutanediol residues; and
    ii) 35 to 60 mole % of 1,4-cyclohexanedimethanol residues, wherein the total mole % of said dicarboxylic acid component is 100 mole %, and the total mole % of said glycol component is 100 mole %; and wherein the inherent viscosity of said polyester is from 0.5 to 1.2 dL/g as determined in 60/40 (wt/wt) phenol/tetrachloroethane at a concentration of 0.5 g/100 ml at 25° C.

One embodiment of the present invention provides a thermoplastic article having one or more decorative materials embedded therein comprising: at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 65 mole % of 2,2,4,4-tetramethyl-1,3-cyclobutanediol; and
  ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 110 to 160° C.

One embodiment of the present invention provides a thermoplastic article having one or more decorative materials embedded therein comprising: at least one polyester which comprises:
(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 65 mole % of 2,2,4,4-tetramethyl-1,3-cyclobutanediol; and
  ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 110 to 160° C.

One embodiment of the present invention provides a A thermoplastic article having one or more decorative materials embedded therein comprising: at least one polyester which comprises:
(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 65 mole % of 2,2,4,4-tetramethyl-1,3-cyclobutanediol; and
  ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 110 to 150° C.

One embodiment of the present invention provides a thermoplastic article having one or more decorative materials embedded therein comprising:
(I) at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 40 to 65 mole % of 2,2,4,4-tetramethyl-1,3-cyclobutanediol; and
    ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 120 to 160° C.

One embodiment of the present invention provides a thermoplastic article having one or more decorative materials embedded therein comprising: at least one polyester which comprises:
(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 65 mole % of 2,2,4,4-tetramethyl-1,3-cyclobutanediol; and
  ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 120 to 135° C.

One embodiment of the present invention provides a thermoplastic article having one or more decorative materials embedded therein comprising: at least one polyester which comprises:
(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 65 mole % of 2,2,4,4-tetramethyl-1,3-cyclobutanediol; and
  ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 130 to 145° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol; and
   ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 0.75 dL/g as determined in 60/40 (wt/wt) phenol/tetrachloroethane at a concentration of 0.5 g/100 ml at 25° C.; and wherein said polyester has a Tg of 110 to 160° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol; and
   ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 0.75 dL/g as determined in 60/40 (wt/wt) phenol/tetrachloroethane at a concentration of 0.5 g/100 ml at 25° C.; and wherein said polyester has a Tg of 110 to 150° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol; and
   ii) 35 to 60 mole % of 1,4-cyclohexanedimethanol;

wherein the total mole % of said dicarboxylic acid component is 100 mole %, and the total mole % of said glycol component is 100 mole %; and wherein said inherent viscosity of said polyester is from 0.50 to 0.75 dL/g as determined in 60/40 (wt/wt) phenol/tetrachloroethane at a concentration of 0.5 g/100 ml at 25° C.; and wherein said polyester has a Tg of 120 to 160° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol; and
   ii) 35 to 60 mole % of 1,4-cyclohexanedimethanol;

wherein said total mole % of said dicarboxylic acid component is 100 mole %, and said total mole % of said glycol component is 100 mole %; and wherein the inherent viscosity of said polyester is from 0.50 to 0.75 dL/g as determined in 60/40 (wt/wt) phenol/tetrachloroethane at a concentration of 0.5 g/100 ml at 25° C.; and wherein said polyester has a Tg of 120 to 150° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol; and
   ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 0.75 dL/g as determined in 60/40 (wt/wt) phenol/tetrachloroethane at a concentration of 0.5 g/100 ml at 25° C.; and wherein said polyester has a Tg of 120 to 135° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol; and
   ii) 35 to 60 mole % of 1,4-cyclohexanedimethanol;

wherein the total mole % of said dicarboxylic acid component is 100 mole %, and the total mole % of said glycol component is 100 mole %; and wherein the inherent viscosity of said polyester is from 0.50 to 0.75 dL/g as determined in 60/40 (wt/wt) phenol/tetrachloroethane at a concentration of 0.5 g/100 ml at 25° C.; and wherein said polyester has a Tg of 130 to 145° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 40 to 65 mole % of 2,2,4,4-tetramethyl-1,3-cyclobutanediol residues; and
  - ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 0.72 dL/g as determined in 60/40 (wt/wt) phenol/tetrachloroethane at a concentration of 0.5 g/100 ml at 25° C.; and wherein said polyester has a Tg of 110 to 160° C.

One embodiment of the present invention provides a thermoplastic article having one or more decorative materials embedded therein comprising: at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 40 to 65 mole % of 2,2,4,4-tetramethyl-1,3-cyclobutanediol residues; and
  - ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 0.68 dL/g as determined in 60/40 (wt/wt) phenol/tetrachloroethane at a concentration of 0.5 g/100 ml at 25° C.; and wherein said polyester has a Tg of 110 to 160° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 40 to 65 mole % of 2,2,4,4-tetramethyl-1,3-cyclobutanediol residues; and
  - ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to less than 0.68 dL/g as determined in 60/40 (wt/wt) phenol/tetrachloroethane at a concentration of 0.5 g/100 ml at 25° C.; and wherein said polyester has a Tg of 110 to 160° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 1 to 99 mole % of 2,2,4,4-tetramethyl-1,3-cyclobutanediol residues; and
  - ii) 1 to 99 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to less than 0.70 dL/g as determined in 60/40 (wt/wt) phenol/tetrachloroethane at a concentration of 0.5 g/100 ml at 25° C.; and wherein said polyester has a Tg from 110 to 200° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 40 to 80 mole % of 2,2,4,4-tetramethyl-1,3-cyclobutanediol residues; and
  - ii) 20 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 1.2 dL/g as determined in 60/40 (wt/wt) phenol/tetrachloroethane at a concentration of 0.5 g/100 ml at 25° C.; and wherein said polyester has a Tg from 110 to 200° C.

One embodiment of the invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 40 to 65 mole % of 2,2,4,4-tetramethyl-1,3-cyclobutanediol residues; and
  - ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.; and wherein said polyester has a Tg from 110 to 200° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 64.9 mole % of 2,2,4,4-tetramethyl-1,3-cyclobutanediol residues;
   ii) 35 to 59.99 mole % of 1,4-cyclohexanedimethanol residues, and
   iii) 0.01 to less than 15 mole % ethylene glycol;

wherein the total mole % of said dicarboxylic acid component is 100 mole %, and the total mole % of said glycol component is 100 mole %; and wherein the inherent viscosity of said polyester is from 0.35 to 0.75 dL/g or less as determined in 60/40 (wt/wt) phenol/tetrachloroethane at a concentration of 0.5 g/100 ml at 25° C.; wherein said polyester has a Tg from 110 to 200° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 55 mole % of 2,2,4,4-tetramethyl-1,3-cyclobutanediol residues; and
   ii) 45 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.; wherein said polyester has a Tg from 110 to 200° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 45 to 55 mole % of 2,2,4,4-tetramethyl-1,3-cyclobutanediol residues; and
   ii) 45 to 55 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.; wherein said polyester has a Tg of 110 to 200° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol residues; and
   ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.;

wherein said polyester has a Tg from 110 to 200° C. and optionally, wherein one or more branching agents is added prior to or during the polymerization of said polyester.

One embodiment of the present invention provides a thermoplastic article having one or more decorative materials embedded therein comprising: at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 1 to 99 mole % of 2,2,4,4-tetramethyl-1,3-cyclobutanediol residues; and
   ii) 1 to 99 mole % of 1,4-cyclohexanedimethanol residues; and
(c) residues of at least one branching agent;

wherein the total mole % of said dicarboxylic acid component is 100 mole %, and the total mole % of said glycol component is 100 mole %; and wherein the inherent viscosity of said polyester is from 0.35 to 1.2 dL/g as determined in 60/40 (wt/wt)phenol/tetrachloroethane at a concentration of 0.5 g/100 ml at 25° C.; wherein said polyester has a Tg from 110 to 200° C.

One embodiment of the present invention provides a thermoplastic article having one or more decorative materials embedded therein comprising:

at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol residues; and
   ii) 35 to 60 mole % of 1,4-cyclohexanedimethanol residues; and
(c) residues of at least one branching agent;

wherein the total mole % of said dicarboxylic acid component is 100 mole %, and the total mole % of said glycol component is 100 mole %; and wherein the inherent viscosity of said polyester is from 0.35 to 1.2 dL/g as determined in 60/40 (wt/wt)phenol/tetrachloroethane at a concentration of 0.5 g/100 ml at 25° C.; wherein said polyester has a Tg from 110 to 200° C.

One embodiment of the present invention provides a thermoplastic article having one or more decorative materials embedded therein comprising:
at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol residues; and
   ii) 35 to 60 mole % of 1,4-cyclohexanedimethanol residues; and
(c) residues of at least one branching agent;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt)phenol/tetrachloroethane at a concentration of 0.5 g/100 ml at 25° C.; wherein said polyester has a Tg from 110 to 200° C.

One embodiment of the present invention provides a thermoplastic article having one or more decorative materials embedded therein comprising:
at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 1 to 99 mole % of 2,2,4,4-tetramethyl-1,3-cyclobutanediol residues; and
   ii) 1 to 99 mole % of 1,4-cyclohexanedimethanol residues, wherein the total mole % of said dicarboxylic acid component is 100 mole %, and the total mole % of said glycol component is 100 mole %; and wle;.5qherein the inherent viscosity of said polyester is from 0.35 to 1.2 dL/g as determined in 60/40 (wt/wt)phenol/tetrachloroethane at a concentration of 0.5 g/100 ml at 25° C.;

wherein said polyester has a Tg from 110 to 200° C.

One embodiment of the present invention provides a thermoplastic article having one or more decorative materials embedded therein comprising:
at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol residues; and
   ii) 35 to 60 mole % of 1,4-cyclohexanedimethanol residues, wherein the total mole % of said dicarboxylic acid component is 100 mole %, and the total mole % of said glycol component is 100 mole %; and wherein the inherent viscosity of said polyester is from 0.35 to 1.2 dL/g as determined in 60/40 (wt/wt)phenol/tetrachloroethane at a concentration of 0.5 g/100 ml at 25° C.;

wherein said polyester has a Tg from 110 to 200° C.

One embodiment of the present invention provides a thermoplastic article having one or more decorative materials embedded therein comprising:
at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol residues; and
   ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt)phenol/tetrachloroethane at a concentration of 0.5 g/100 ml at 25° C.;

wherein said polyester has a Tg from 110 to 200° C.

One embodiment of the present invention provides a thermoplastic article having one or more decorative materials embedded therein comprising:
at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 40 to 65 mole % of 2,2,4,4-tetramethyl-1,3-cyclobutanediol residues; and
   ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.; and wherein said polyester has a Tg from 110 to 160° C.

One embodiment of the present invention provides a thermoplastic article having one or more decorative materials embedded therein comprising:
at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 40 to 65 mole % of 2,2,4,4-tetramethyl-1,3-cyclobutanediol residues; and
    ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.; and wherein said polyester has a Tg from 120 to 135° C.

One embodiment of the present invention provides a thermoplastic article having one or more decorative materials embedded therein comprising:
at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 40 to 65 mole % of 2,2,4,4-tetramethyl-1,3-cyclobutanediol residues; and
    ii) 35 to 60 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.; and wherein said polyester has a Tg from 130 to 145° C.

One embodiment of the present invention provides a thermoplastic article having one or more decorative materials embedded therein comprising:
at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 1 to 99 mole % of 2,2,4,4-tetramethyl-1,3-cyclobutanediol residues; and
    ii) 1 to 99 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 0.75 dL/g as determined in 60/40 (wt/wt) phenol/tetrachloroethane at a concentration of 0.5 g/100 ml at 25° C.; and wherein said polyester has a Tg from greater than 148° C. up to 200° C.

One embodiment of the present invention provides a thermoplastic article having one or more decorative materials embedded therein comprising:
at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 1 to 99 mole % of 2,2,4,4-tetramethyl-1,3-cyclobutanediol residues; and
    ii) 1 to 99 mole % of 1,4-cyclohexanedimethanol residues, wherein the total mole % of said dicarboxylic acid component is 100 mole %, and the total mole % of said glycol component is 100 mole %; and wherein the inherent viscosity of said polyester is from 0.35 to 1.2 dL/g as determined in 60/40 (wt/wt) phenol/tetrachloroethane at a concentration of 0.5 g/100 ml at 25° C.; and wherein said polyester has a Tg from 127° C. to 200° C.

One embodiment of the present invention provides a thermoplastic article having one or more decorative materials embedded therein comprising:
at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 1 to 80 mole % of 2,2,4,4-tetramethyl-1,3-cyclobutanediol residues; and
    ii) 20 to 99 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 1.2 dL/g as determined in 60/40 (wt/wt) phenol/tetrachloroethane at a concentration of 0.5 g/100 ml at 25° C.; and wherein said polyester has a Tg of greater than 124° C. to 200° C.

One embodiment of the present invention provides a thermoplastic article having one or more decorative materials embedded therein comprising:
at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and (b) a glycol component comprising:
   i) greater than 50 up to 99 mole % of 2,2,4,4-tetramethyl-1,3-cyclobutanediol residues; and
   ii) 1 to less than 50 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 1.2 dL/g as determined in 60/40 (wt/wt) phenol/tetrachloroethane at a concentration of 0.5 g/100 ml at 25° C.; and wherein said polyester has a Tg from 110° C. to 200° C.

One embodiment of the present invention provides a thermoplastic article having one or more decorative materials embedded therein comprising:
at least one polyester which comprises:
   (a) a dicarboxylic acid component comprising:
      i) 70 to 100 mole % of terephthalic acid residues;
      ii) 0 to 30 mole % of aromatic dicarboxylic acid residues having up to 20 carbon atoms; and
      iii) 0 to 10 mole % of aliphatic dicarboxylic acid residues having up to 16 carbon atoms; and
   (b) a glycol component comprising:
      i) greater than 50 up to 80 mole % of 2,2,4,4-tetramethyl-1,3-cyclobutanediol residues; and
      ii) 20 to less than 50 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.35 to 01.2 dL/g as determined in 60/40 (wt/wt) phenol/tetrachloroethane at a concentration of 0.5 g/100 ml at 25° C.; and wherein said polyester has a Tg from 110° C. to 200° C.

One embodiment of the present invention provides a thermoplastic article having one or more decorative materials embedded therein comprising:
at least one polyester which comprises:
   (a) a dicarboxylic acid component comprising:
      i) 70 to 100 mole % of terephthalic acid residues;
      ii) 0 to 30 mole % of aromatic dicarboxylic acid residues having up to 20 carbon atoms; and
      iii) 0 to 10 mole % of aliphatic dicarboxylic acid residues having up to 16 carbon atoms; and
   (b) a glycol component comprising:
      i) 1 to 99 mole % of 2,2,4,4-tetramethyl-1,3-cyclobutanediol residues; and
      ii) 1 to 99 mole % of 1,4-cyclohexanedimethanol residues; and wherein the total mole % of said dicarboxylic acid component is 100 mole %, the total mole % of said glycol component is 100 mole %; and wherein the inherent viscosity of said polyester is greater than 0.76 up to 1.2 dL/g as determined in 60/40 (wt/wt) phenol/tetrachloroethane at a concentration of 0.5 g/100 ml at 25° C.; and wherein said polyester has a Tg from 110° C. to 200° C.

One embodiment of the present invention provides a thermoplastic article having one or more decorative materials embedded therein comprising:
at least one polyester which comprises:
   (a) a dicarboxylic acid component comprising:
      i) 70 to 100 mole % of terephthalic acid residues;
      ii) 0 to 30 mole % of aromatic dicarboxylic acid residues having up to 20 carbon atoms; and
      iii) 0 to 10 mole % of aliphatic dicarboxylic acid residues having up to 16 carbon atoms; and
   (b) a glycol component comprising:
      i) 1 to 99 mole % of 2,2,4,4-tetramethyl-1,3-cyclobutanediol residues; and
      ii) 1 to 99 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is 0.10 to less than 1.0 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:
at least one polyester which comprises:
   (a) a dicarboxylic acid component comprising:
      i) 70 to 100 mole % of terephthalic acid residues;
      ii) 0 to 30 mole % of aromatic dicarboxylic acid residues having up to 20 carbon atoms; and
      iii) 0 to 10 mole % of aliphatic dicarboxylic acid residues having up to 16 carbon atoms; and
   (b) a glycol component comprising:
      i) 1 to 99 mole % of 2,2,4,4-tetramethyl-1,3-cyclobutanediol residues; and
      ii) 1 to 99 mole % of 1,4-cyclohexanedimethanol residues, wherein the total mole % of said dicarboxylic acid component is 100 mole %, and the total mole % of said glycol component is 100 mole %; and wherein the inherent viscosity of said polyester is 0.35 to less than 1.0 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:
at least one polyester which comprises:
   (a) a dicarboxylic acid component comprising:
      i) 70 to 100 mole % of terephthalic acid residues;
      ii) 0 to 30 mole % of aromatic dicarboxylic acid residues having up to 20 carbon atoms; and
      iii) 0 to 10 mole % of aliphatic dicarboxylic acid residues having up to 16 carbon atoms; and
   (b) a glycol component comprising:
      i) 5 to less than 50 mole % of 2,2,4,4-tetramethyl-1,3-cyclobutanediol residues; and
      ii) greater than 50 to 95 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 10 to 30 mole % of 2,2,4,4-tetramethyl-1,3-cyclobutanediol residues; and
  - ii) 70 to 90 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 15 to 25 mole % of 2,2,4,4-tetramethyl-1,3-cyclobutanediol residues; and
  - ii) 75 to 85 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 5 to less than 50 mole % of 2,2,4,4-tetramethyl-1,3-cyclobutanediol residues; and
  - ii) greater than 50 to 95 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and wherein said polyester has a Tg of 95 to 115° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 10 to 30 mole % of 2,2,4,4-tetramethyl-1,3-cyclobutanediol residues; and
  - ii) 70 to 90 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and
wherein said polyester has a Tg of 95 to 115° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 15 to 25 mole % of 2,2,4,4-tetramethyl-1,3-cyclobutanediol residues; and
  - ii) 75 to 85 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to 1.2 dL/g as determined in 60/40 (wt/wt) phenol/tetrachloroethane at a concentration of 0.5 g/100 ml at 25° C.; and
wherein said polyester has a Tg of 95 to 115° C.

One embodiment of the present invention provides a thermoplastic article having one or more decorative materials embedded therein comprising:

at least one polyester which comprises:
- (a) a dicarboxylic acid component comprising:
  - i) 70 to 100 mole % of terephthalic acid residues;
  - ii) 0 to 30 mole % of aromatic dicarboxylic acid residues having up to 20 carbon atoms; and
  - iii) 0 to 10 mole % of aliphatic dicarboxylic acid residues having up to 16 carbon atoms; and
- (b) a glycol component comprising:
  - i) 5 to less than 50 mole % of 2,2,4,4-tetramethyl-1,3-cyclobutanediol residues; and
  - ii) greater than 50 to 95 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to less than 0.75 dL/g as determined in 60/40 (wt/wt) phenol/ tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:

at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 10 to 30 mole % of 2,2,4,4-tetramethyl-1,3-cyclobutanediol residues; and
 ii) 70 to 90 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to less than 0.75 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 15 to 25 mole % of 2,2,4,4-tetramethyl-1,3-cyclobutanediol residues; and
 ii) 75 to 85 mole % of 1,4-cyclohexanedimethanol residues;
wherein the total mole % of said dicarboxylic acid component is 100 mole %, and the total mole % of said glycol component is 100 mole %; and wherein the inherent viscosity of said polyester is from 0.50 to less than 0.75 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:

at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 5 to less than 50 mole % of 2,2,4,4-tetramethyl-1,3-cyclobutanediol residues; and
 ii) greater than 50 to 95 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to less than 0.75 dL/g as determined in 60/40 (wt/wt) phenol/tetrachloroethane at a concentration of 0.5 g/100 ml at 25° C.; and wherein said polyester has a Tg of 95 to 115° C.

One embodiment of the present invention provides a thermoplastic article having one or more decorative materials embedded therein comprising:

at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 10 to 30 mole % of 2,2,4,4-tetramethyl-1,3-cyclobutanediol residues; and
 ii) 70 to 90 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to less than 0.75 dL/g as determined in 60/40 (wt/wt) phenol/tetrachloroethane at a concentration of 0.5 g/100 ml at 25° C.; and wherein said polyester has a Tg of 95 to 115° C.

One embodiment of the present invention provides a thermoplastic article having one or more decorative materials embedded therein comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 15 to 25 mole % of 2,2,4,4-tetramethyl-1,3-cyclobutanediol residues; and
 ii) 75 to 85 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.50 to less than 0.75 dL/g as determined in 60/40 (wt/wt) phenol/tetrachloroethane at a concentration of 0.5 g/100 ml at 25° C.; and wherein said polyester has a Tg of 95 to 115° C.

One embodiment of the present invention provides a thermoplastic article having one or more decorative materials embedded therein comprising:

at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 15 to 25 mole % of 2,2,4,4-tetramethyl-1,3-cyclobutanediol residues; and
 ii) 75 to 85 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is from 0.60 to 0.72 dL/g as determined in 60/40 (wt/wt) phenol/tetrachloroethane at a concentration of 0.5 g/100 ml at 25° C.; and wherein said polyester has a Tg of 95 to 115° C.

One embodiment of the present invention provides a thermoplastic article having one or more decorative materials embedded therein comprising:

at least one polyester which comprises:
 (a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
 (b) a glycol component comprising:
  i) 1 to 99 mole % of 2,2,4,4-tetramethyl-1,3-cyclobutanediol residues; and
  ii) 1 to 98.99 mole % of 1,4-cyclohexanedimethanol residues,
  iii) 0.01 to less than 15 mole % ethylene glycol;

wherein the total mole % of said dicarboxylic acid component is 100 mole %, and the total mole % of said glycol component is 100 mole %; and wherein the inherent viscosity of said polyester is 0.35 to 1.2 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:

at least one polyester which comprises:
 (a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
 (b) a glycol component comprising:
  i) 1 to 99 mole % of 2,2,4,4-tetramethyl-1,3-cyclobutanediol residues; and
  ii) 1 to 99 mole % of 1,4-cyclohexanedimethanol residues;

wherein the total mole % of said dicarboxylic acid component is 100 mole %, and the total mole % of said glycol component is 100 mole %; and wherein the inherent viscosity of said polyester is 0.35 to 1.2 dL/g as determined in 60/40 (wt/wt) phenol/tetrachloroethane at a concentration of 0.5 g/100 ml at 25° C.; and wherein said polyester has a Tg of 85 to 120° C.; and optionally, wherein one or more branching agents is added prior to or during the polymerization of the polyester.

One embodiment of the present invention provides a thermoplastic article having one or more decorative materials embedded therein comprising:

at least one polyester which comprises:
 (a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms;
 (b) a glycol component comprising:
  i) 1 to 99 mole % of 2,2,4,4-tetramethyl-1,3-cyclobutanediol residues; and
  ii) 1 to 99 mole % of 1,4-cyclohexanedimethanol residues; and
 (c) residues from at least one branching agent;

wherein the total mole % of said dicarboxylic acid component is 100 mole %, and the total mole % of said glycol component is 100 mole %; and wherein the inherent viscosity of said polyester is 0.35 to 1.2 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a thermoplastic article having one or more decorative materials embedded therein comprising:

at least one polyester which comprises:
 (a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
 (b) a glycol component comprising:
  i) 1 to 99 mole % of 2,2,4,4-tetramethyl-1,3-cyclobutanediol residues; and
  ii) 1 to 99 mole % of 1,4-cyclohexanedimethanol residues; and at least one thermal stabilizer or reaction products thereof;

wherein the total mole % of said dicarboxylic acid component is 100 mole %, and the total mole % of said glycol component is 100 mole %; and wherein the inherent viscosity of said polyester is 0.35 to 1.2 dL/g as determined in 60/40 (wt/wt) phenol/tetrachloroethane at a concentration of 0.5 g/100 ml at 25° C.; and wherein said polyester has a Tg of 85 to 120° C.

One embodiment of the present invention provides a solid surface prepared from polyesters laminated onto an image layer comprising:
 (a) an outer layer comprising any of the articles described above;
 (b) a polymeric film having a top side and a bottom side, wherein an image is printed on one of said sides and said film is joined to said outer layer such that said image can be seen through said outer layer; and
 (c) a backing layer comprising a polymer selected from the group consisting of polyvinyl chloride and polyester, said backing layer having a side joined to said polymeric film opposite said outer layer; wherein said outer layer and said backing layer are thermally compatible.

One embodiment of the present invention provides any of thermoplastic articles described above further having a high-relief, moled or embossed surface obtained by contacting a laminate comprising a first sheet material and a second sheet material with heat and pressure using a heated element which results in simultaneous bonding of the sheet material and the production of a decorative texture or design on the surface of at least one one of the sheets.

One embodiment of the present invention provide a thermoplastic laminated article comprising:
(a) a first thermoplastic layer selected from any of the thermoplastic articles described above and having first and second surfaces;
(b) a second thermoplastic layer selected from the group consisting of polyethylene and polypropylene and having a third surface disposed toward said first surface; and
(c) a bonding agent disposed between said first and third surfaces for securing said first thermoplastic layer and said second thermoplastic layer.

One embodiment of the present invention provide a thermoplastic laminated article comprising:
(a) a first thermoplastic layer having a first and second surfaces;
(b) a second thermoplastic layer having a third surface disposed toward sad first surface; and
(c) a bonding agent disposed between said first and third surfaces for securing said first thermoplastic layer and said second thermoplastic layer, wherein said first thermoplastic layer comprises any of the thermoplastic articles described above and said second thermoplastic layer is a polyolefinic material selected from polyethylene and polypropylene.

One embodiment of the present invention provides a thermoplastic article having one or more decorative materials embedded therein obtained by applying heat and pressure to a laminate comprising, in order, (1) an upper sheet material, (2) a decorative material, and (30 a lower sheet material; wherein the upper and lower sheet materials are formed from any of the thermoplastic articles described above.

One embodiment of the present invention provides a synthetic laminate structure comprising:
(a) an outer layer comprising any of the thermoplastic articles described above;
(b) a printed or colored film layer having opposed surfaces wherein at least one of the surfaces is colored or has an image printed thereon;
(c) a backing layer disposed adjacent the film layer comprising a polymer selected from the group consisting of polyvinyl chloride and a copolyester; and
(d) a laminating enhancer layer comprising a polyurethane disposed between the outer layer and the film layer providing a bond between the layers which is characterized by a substantial absence of visible air pockets or adhesion discontinuities.

One embodiment of the present invention provides a solid surface prepared from copolyesters laminated onto an image layer comprising:
(a) an outer layer comprising any of the thermoplastic articles described above;
(b) a polymeric film having a top side and a bottom side, wherein an image is printed on one of said sides and said film is joined to said outer layer such that said image can be seen through said outer layer; and
(c) a backing layer comprising a polymer selected from the group consisting of polyvinyl chloride and polyester, said backing layer having a side joined to said polymeric film opposite said outer layer; wherein said outer layer and said backing layer are thermally compatible.

In one aspect, the polyesters useful in the invention contain less than 15 mole % ethylene glycol residues.

In one aspect, the polyesters useful in the invention contain no ethylene glycol residues.

In one aspect the polyester compositions useful in the invention contain at least one thermal stabilizer or reaction products thereof.

In one aspect, the polyesters useful in the invention contain no residues of at least one branching agent, or alternatively, at least one branching agent is added either prior to or during polymerization of the polyester.

In one aspect, the polyesters useful in the invention contain branching agent without regard to the method or sequence in which it is added.

In one aspect, the polyesters useful in the invention contain is made from no 1,3-propanediol, or, 1,4-butanediol, either singly or in combination. In other aspects, 1,3-propanediol or 1,4-butanediol, either singly or in combination, may be used in the making of present in the polyesters of this invention.

In one aspect of the invention, the mole % of cis-2,2,4,4-tetramethyl-1,3-cyclobutanediol useful in certain polyesters useful in this invention is greater than 50 mole % or greater than 55 mole % of cis-2,2,4,4-tetramethyl-1,3-cyclobutanediol or greater than 70 mole % of cis-2,2,4,4-tetramethyl-1,3-cyclobutanediol; wherein the total mole percentage of cis-2,2,4,4-tetramethyl-1,3-cyclobutanediol and trans-2,2,4,4-tetramethyl-1,3-cyclobutanediol is equal to a total of 100 mole %.

In one aspect, certain polyesters useful in the invention are amorphous or semicrystalline. In one aspect, certain polyesters useful in the invention can have a relatively low crystallinity. Certain polyesters useful in the invention can thus have a substantially amorphous morphology, meaning that the polyesters comprise substantially unordered regions of polymer.

DETAILED DESCRIPTION OF THE INVENTION

Figure 1:
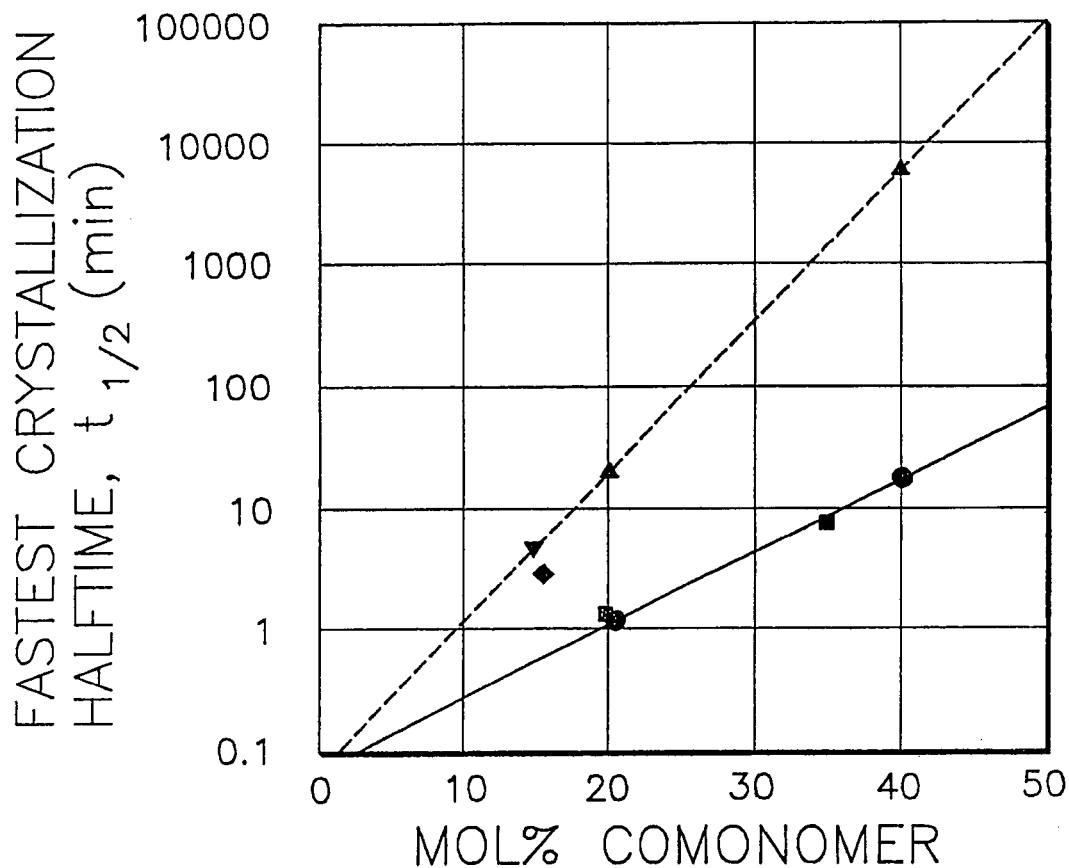
FIG. 1 is a graph showing the effect of comonomer on the fastest crystallization half-times of modified PCT copolyesters.

The present invention may be understood more readily by reference to the following detailed description of certain embodiments of the invention and the working examples.

It is believed that thermoplastic articles comprising the polyester(s) having the composition(s) described herein can have a combination of one or more physical properties such as high impact strengths, high glass transition temperatures, chemical resistance, hydrolytic stability, low ductile-to-brittle transition temperatures, good color and good clarity, low densities, and long crystallization half-times, and good processability thereby easily permitting them to be formed. In some of the embodiments of the invention, the advantageously superior combination of the properties of good impact strength, heat resistance, chemical resistance, density and/or the combination of the properties of good impact strength, heat resistance, and processability and/or the combination of all four of the described properties, have never before been believed to be present in thermoplastic articles, such as sheet(s), comprising the polyester compositions which comprise the polyester(s) as disclosed herein. The polyesters used in the polyester compositions useful in making these thermoplastic articles of the invention are believed to have a unique combination of at least two of high impact strengths, high glass transition temperature ($T_g$), low ductileto-brittle transition temperatures, good color and clarity, low densities, and long crystallization half-times, which allow them to be easily formed into articles. Such polyesters and/or polyester compositions useful in the invention, and sheet(s) and/or film(s) formed therefrom may be thermoformed without having to pre-dry the sheet(s) and/or film(s).

The term "polyester", as used herein, is intended to include "copolyesters" and is understood to mean a synthetic polymer prepared by the reaction of one or more difunctional carboxylic acids with one or more difunctional hydroxyl compounds. Typically the difunctional carboxylic acid can be a dicarboxylic acid and the difunctional hydroxyl compound can be a dihydric alcohol such as, for example, glycols and diols. Alternatively, the difunctional carboxylic acid may be a hydroxy carboxylic acid such as, for example, p-hydroxybenzoic acid, and the difunctional hydroxyl compound may be an aromatic nucleus bearing 2 hydroxyl substituents such as, for example, hydroquinone. The term "residue", as used herein, means any organic structure incorporated into a polymer through a polycondensation and/or an esterification reaction from the corresponding monomer. The term "repeating unit", as used herein, means an organic structure having a dicarboxylic acid residue and a diol residue bonded through a carbonyloxy group. Thus, for example, the dicarboxylic acid residues may be derived from a dicarboxylic acid monomer or its associated acid halides, esters, salts, anhydrides, or mixtures thereof. As used herein, therefore, the term dicarboxylic acid is intended to include dicarboxylic acids and any derivative of a dicarboxylic acid, including its associated acid halides, esters, half-esters, salts, half-salts, anhydrides, mixed anhydrides, or mixtures thereof, useful in a reaction process with a diol to make polyester. As used herein, the term "terephthalic acid" is intended to include terephthalic acid itself as well as any derivative of terephthalic acid, including its associated acid halides, esters, half-esters, salts, half-salts, anhydrides, mixed anhydrides, or mixtures thereof useful in a reaction process with a diol to make polyester.

As used herein the term "decorative material", which may be natural or synthetic, includes, but is not limited to, metallic wire, rods or bars; natural fibers, glass fibers, mineral fibers, fabric, papers; printed layers, wood, stone, photographic images, wood chips, grasses, vegetation, thatch, bamboo, tree or bush branches or stems, will reed leaves, beans, flowers, flower petals, wheat, grains, and crushed glass. The term "decorative" means ornamental; or serving an esthetic rather than a useful purpose; or serving to make something look more attractive by adding nonfunctional embellishments. The term "embedded" refers to any decorative materials or objects that are intended to be, or have already been, embedded in a decorative laminate panel, such as any organic and inorganic materials.

In one embodiment, terephthalic acid may be used as the starting material. In another embodiment, dimethyl terephthalate may be used as the starting material. In another embodiment, mixtures of terephthalic acid and dimethyl terephthalate may be used as the starting material.

The polyesters used in the present invention typically can be prepared from dicarboxylic acids and diols which react in substantially equal proportions and are incorporated into the polyester polymer as their corresponding residues. The polyesters of the present invention, therefore, can contain substantially equal molar proportions of acid residues (100 mole %) and diol residues (100 mole %) such that the total moles of repeating units is equal to 100 mole %. The mole percentages provided in the present disclosure, therefore, may be based on the total moles of acid residues, the total moles of diol residues, or the total moles of repeating units. For example, a polyester containing 30 mole % isophthalic acid, based on the total acid residues, means the polyester contains 30 mole % isophthalic acid residues out of a total of 100 mole % acid residues. Thus, there are 30 moles of isophthalic acid residues among every 100 moles of acid residues. In another example, a polyester containing 30 mole % 2,2,4,4-tetramethyl-1,3-cyclobutanediol, based on the total diol residues, means the polyester contains 30 mole % 2,2,4,4-tetramethyl-1,3-cyclobutanediol residues out of a total of 100 mole % diol residues. Thus, there are 30 moles of 2,2,4,4-tetramethyl-1,3-cyclobutanediol residues among every 100 moles of diol residues.

In other aspects of the invention, the Tg of the polyesters useful in the thermoplastic articles of the invention can be at least one of the following ranges: 110 to 200° C.; 110 to 190° C.; 110 to 180° C.; 110 to 170° C.; 110 to 160° C.; 110 to 155° C.; 110 to 150° C.; 110 to 145° C.; 110 to 140° C.; 110 to 138° C.; 110 to 135° C.; 110 to 130° C.; 110 to 125° C.; 110 to 120° C.; 110 to 115° C.; 115 to 200° C.; 115 to 190° C.; 115 to 180° C.; 115 to 170° C.; 115 to 160° C.; 115 to 155° C.; 115 to 150° C.; 115 to 145° C.; 115 to 140° C.; 115 to 138° C.; 115 to 135° C.; 110 to 130° C.; 115 to 125° C.; 115 to 120° C.; 120 to 200° C.; 120 to 190° C.; 120 to 180° C.; 120 to 170° C.; 120 to 160° C.; 120 to 155° C.; 120 to 150° C.; 120 to 145° C.; 120 to 140° C.; 120 to 138° C.; 120 to 135° C.; 120 to 130° C.; 125 to 200° C.; 125 to 190° C.; 125 to 180° C.; 125 to 170° C.; 125 to 160° C.; 125 to 155° C.; 125 to 150° C.; 125 to 145° C.; 125 to 140° C.; 125 to 138° C.; 125 to 135° C.; 127 to 200° C.; 127 to 190° C.; 127 to 180° C.; 127 to 170 ° C.; 127 to 160° C.; 127 to 150° C.; 127 to 145° C.; 127 to 140° C.; 127 to 138° C.; 127 to 135° C.; 130 to 200° C.; 130 to 190° C.; 130 to 180° C.; 130 to 170° C.; 130 to 160° C.; 130 to 155° C.; 130 to 150° C.; 130 to 145° C.; 130 to 140° C.; 130 to 138° C.; 130 to 135° C.; 135 to 200° C.; 135 to 190° C.; 135 to 180° C.; 135 to 170° C.; 135 to 160° C.; 135 to 155° C.; 135 to 150° C.; 135 to 145° C.; 135 to 140° C.; 140 to 200° C.; 140 to 190° C.; 140 to 180 ° C.; 140 to 170° C.; 140 to 160° C.; 140 to 155° C.; 140 to 150° C.; 140 to 145 ° C.; 148 to 200° C.; 148 to 190° C.; 148 to 180° C.; 148 to 170° C.; 148 to 160° C.; 148 to 155° C.; 148 to 150° C.; 150 to 200° C.; 150 to 190° C.; 150 to 180° C.; 150 to 170° C.; 150 to 160; 155 to 190° C.; 155 to 180° C.; 155 to 170° C.; and 155 to 165° C.

In other aspects of the invention, the glycol component for the polyesters useful in the thermoplastic articles of the invention include, but are not limited to, at least one of the following combinations of ranges: greater than 20 to 99 mole % 2,2,4,4-tetramethyl-1,3-cyclobutanediol and 1 to less than 80 mole % 1,4-cyclohexanedimethanol; greater than 20 to 95 mole % 2,2,4,4-tetramethyl-1,3-cyclobutanediol and 5 to less than 80 mole % 1,4-cyclohexanedimethanol; greater than 20 to 90 mole % 2,2,4,4-tetramethyl-1,3-cyclobutanediol and 10 to less than 80 mole % 1,4-cyclohexanedimethanol; greater than 20 to 85 mole % 2,2,4,4-tetramethyl-1,3-cyclobutanediol and 15 to less than 80 mole % 1,4-cyclohexanedimethanol; greater than 20 to 80 mole % 2,2,4,4-tetramethyl-1,3-cyclobutanediol and 20 to less than 80 mole % 1,4-cyclohexanedimethanol, greater than 20 to 75 mole % 2,2,4,4-tetramethyl-1,3-cyclobutanediol and 25 to less than 80 mole % 1,4-cyclohexanedimethanol; greater than 20 to 70 mole % 2,2,4,4-tetramethyl-1,3-cyclobutanediol and 30 to less than 80 mole % 1,4-cyclohexanedimethanol; greater than 20 to 65 mole % 2,2,4,4-tetramethyl-1,3-cyclobutanediol and 35 to less than 80 mole % 1,4-cyclohexanedimethanol; greater than 20 to 60 mole % 2,2,4,4-tetramethyl-1,3-cyclobutanediol and 40 to less than mole % 1,4-cyclohexanedimethanol; greater than 20 to 55 mole % 2,2,4,4-tetramethyl-1,3-cyclobutanediol and 45 to less than 80 mole %

1,4-cyclohexanedimethanol; greater than 20 to 50 mole % 2,2,4,4-tetramethyl-1,3-cyclobutanediol and 50 to less than 80 mole % 1,4-cyclohexanedimethanol; greater than 20 to 45 mole % 2,2,4,4-tetramethyl-1,3-cyclobutanediol and 55 to less than 80 mole % 1,4-cyclohexanedimethanol; greater than 20 to 40 mole % 2,2,4,4-tetramethyl-1,3-cyclobutanediol and 60 to less than 80 mole % 1,4-cyclohexanedimethanol; greater than 20 to 35 mole % 2,2,4,4-tetramethyl-1,3-cyclobutanediol and 65 to less than 80 mole % 1,4-cyclohexanedimethanol; greater than 20 to 30 mole % 2,2,4,4-tetramethyl-1,3-cyclobutanediol and 70 to less than 80 mole % 1,4-cyclohexanedimethanol; greater than 20 to 25 mole % 2,2,4,4-tetramethyl-1,3-cyclobutanediol and 75 to less than 80 mole % 1,4-cyclohexanedimethanol.

In other aspects of the invention, the glycol component for the polyesters useful in the thermoplastic articles of the invention include, but are not limited to, at least one of the following combinations of ranges: 21 to 99 mole % 2,2,4,4-tetramethyl-1,3-cyclobutanediol and 1 to 79 mole % 1,4-cyclohexanedimethanol; 21 to 95 mole % 2,2,4,4-tetramethyl-1,3-cyclobutanediol and 5 to 79 mole % 1,4-cyclohexanedimethanol; 21 to 90 mole % 2,2,4,4-tetramethyl-1,3-cyclobutanediol and 10 to 79 mole % 1,4-cyclohexanedimethanol; 21 to 85 mole % 2,2,4,4-tetramethyl-1,3-cyclobutanediol and 15 to 79 mole % 1,4-cyclohexanedimethanol; 21 to 79 mole % 2,2,4,4-tetramethyl-1,3-cyclobutanediol and 21 to 79 mole % 1,4-cyclohexanedimethanol, 21 to 75 mole % 2,2,4,4-tetramethyl-1,3-cyclobutanediol and 25 to 79 mole % 1,4-cyclohexanedimethanol; 21 to 70 mole % 2,2,4,4-tetramethyl-1,3-cyclobutanediol and 30 to 79 mole % 1,4-cyclohexanedimethanol; 21 to 65 mole % 2,2,4,4-tetramethyl-1,3-cyclobutanediol and 35 to 79 mole % 1,4-cyclohexanedimethanol; 21 to 60 mole % 2,2,4,4-tetramethyl-1,3-cyclobutanediol and 40 to 79 mole % 1,4-cyclohexanedimethanol; 21 to 55 mole % 2,2,4,4-tetramethyl-1,3-cyclobutanediol and 45 to 79 mole % 1,4-cyclohexanedimethanol; 21 to 50 mole % 2,2,4,4-tetramethyl-1,3-cyclobutanediol and 50 to 79 mole % 1,4-cyclohexanedimethanol; 21 to 45 mole % 2,2,4,4-tetramethyl-1,3-cyclobutanediol and 55 to 79 mole % 1,4-cyclohexanedimethanol; 21 to 40 mole % 2,2,4,4-tetramethyl-1,3-cyclobutanediol and 60 to 79 mole % 1,4-cyclohexanedimethanol; 21 to 35 mole % 2,2,4,4-tetramethyl-1,3-cyclobutanediol and 65 to 79 mole % 1,4-cyclohexanedimethanol; 21 to 30 mole % 2,2,4,4-tetramethyl-1,3-cyclobutanediol and 70 to 79 mole % 1,4-cyclohexanedimethanol; and 21 to 25 mole % 2,2,4,4-tetramethyl-1,3-cyclobutanediol and 75 to 79 mole % 1,4-cyclohexanedimethanol.

In other aspects of the invention, the glycol component for the polyesters useful in the thermoplastic articles of the invention include, but are not limited to, at least one of the following combinations of ranges: 25 to 99 mole % 2,2,4,4-tetramethyl-1,3-cyclobutanediol and 1 to 75 mole % 1,4-cyclohexanedimethanol; 25 to 90 mole % 2,2,4,4-tetramethyl-1,3-cyclobutanediol and 10 to 75 mole % 1,4-cyclohexanedimethanol; 25 to 85 mole % 2,2,4,4-tetramethyl-1,3-cyclobutanediol and 15 to 75 mole % 1,4-cyclohexanedimethanol; 25 to 80 mole % 2,2,4,4-tetramethyl-1,3-cyclobutanediol and 20 to 75 mole % 1,4-cyclohexanedimethanol, 25 to 75 mole % 2,2,4,4-tetramethyl-1,3-cyclobutanediol and 25 to 75 mole % 1,4-cyclohexanedimethanol; 25 to 70 mole % 2,2,4,4-tetramethyl-1,3-cyclobutanediol and 30 to 75 mole % 1,4-cyclohexanedimethanol; 25 to 65 mole % 2,2,4,4-tetramethyl-1,3-cyclobutanediol and 35 to 75 mole % 1,4-cyclohexanedimethanol; 25 to 60 mole % 2,2,4,4-tetramethyl-1,3-cyclobutanediol and 40 to 75 mole % 1,4-cyclohexanedimethanol; 25 to 55 mole % 2,2,4,4-tetramethyl-1,3-cyclobutanediol and 45 to 75 mole % 1,4-cyclohexanedimethanol; 25 to 50 mole % 2,2,4,4-tetramethyl-1,3-cyclobutanediol and 50 to 75 mole % 1,4-cyclohexanedimethanol; 25 to 45 mole % 2,2,4,4-tetramethyl-1,3-cyclobutanediol and 55 to 75 mole % 1,4-cyclohexanedimethanol; 25 to 40 mole % 2,2,4,4-tetramethyl-1,3-cyclobutanediol and 60 to 75 mole % 1,4-cyclohexanedimethanol; 25 to 35 mole % 2,2,4,4-tetramethyl-1,3-cyclobutanediol and 65 to 75 mole % 1,4-cyclohexanedimethanol; 25 to 30 mole % 2,2,4,4-tetramethyl-1,3-cyclobutanediol and 70 to 75 mole % 1,4-cyclohexanedimethanol; and 25 to 25 mole % 2,2,4,4-tetramethyl-1,3-cyclobutanediol and 75 to 75 mole % 1,4-cyclohexanedimethanol.

In other aspects of the invention, the glycol component for the polyesters useful in the thermoplastic articles of the invention includes, but are not limited to, the lower limit of 2,2,4,4-tetramethyl-1,3-cyclobutanediol of greater than mole 21 mole %, or about 25 mole %, or about 30 mole %, or about 35 mole %, or about 40 mole %, or about 45 mole %, or about 50 mole %, or about 55 mole %, or about 60 mole %, or about 65 mole %, or about 70 mole %, or about 75 mole %, or about 80 mole %, or about 85 mole %, or about 90 mole %, or about 95 mole %, or about 100 mole %. In other aspects of the invention, the glycol component for the polyesters useful in the thermoplastic articles of the invention includes, but are not limited to, the upper limit of 2,2,4,4-tetramethyl-1,3-cyclobutanediol of about 25 mole %, or about 30 mole %, or about 35 mole %, or about 40 mole %, or about 45 mole %, or about 50 mole %, or about 55 mole %, or about 60 mole %, or about 65 mole %, or about 70 mole %, or about 75 mole %, or about 80 mole %, or about 85 mole %, or about 90 mole %, or about 95 mole %, or about 100 mole %. Any value of a lower limit of 2,2,4,4-tetramenthyl-1,3-cyclobutanediol may be combined with any value for the upper limit for 2,2,4,4-tetramenthyl-1,3-cyclobutanediol.

In other aspects of the invention, the glycol component for the polyesters useful in the thermoplastic articles of the invention include, but are not limited to, at least one of the following combinations of ranges: 35 to 80 mole % 2,2,4,4-tetramethyl-1,3-cyclobutanediol and 20 to 65 mole % 1,4-cyclohexanedimethanol; 37 to 80 mole % 2,2,4,4-tetramethyl-1,3-cyclobutanediol and 20 to 63 mole % 1,4-cyclohexanedimethanol; 40 to 80 mole % 2,2,4,4-tetramethyl-1,3-cyclobutanediol and 20 to 60 mole % 1,4-cyclohexanedimethanol; 45 to 80 mole % 2,2,4,4-tetramethyl-1,3-cyclobutanediol and 20 to 55 mole % 1,4-cyclohexanedimethanol; 50 to 80 mole % 2,2,4,4-tetramethyl-1,3-cyclobutanediol and 20 to 50 mole % 1,4-cyclohexanedimethanol; greater than 50 to 80 mole % 2,2,4,4-tetramethyl-1,3-cyclobutanediol and 20 to less than 50 mole % 1,4-cyclohexanedimethanol; 55 to 80 mole % 2,2,4,4-tetramethyl-1,3-cyclobutanediol and 20 to 45 mole % 1,4-cyclohexanedimethanol; 60 to 80 mole % 2,2,4,4-tetramethyl-1,3-cyclobutanediol and 20 to 40 mole % 1,4-cyclohexanedimethanol; 65 to 80 mole % 2,2,4,4-tetramethyl-1,3-cyclobutanediol and 20 to 35 mole % 1,4-cyclohexanedimethanol; 70 to 80 mole % 2,2,4,4-tetramethyl-1,3-cyclobutanediol and 20 to 30 mole % 1,4-cyclohexanedimethanol; 40 to 75 mole % 2,2,4,4-tetramethyl-1,3-cyclobutanediol and 25 to 60 mole % 1,4-cyclohexanedimethanol; 45 to 75 mole % 2,2,4,4-tetramethyl-1,3-cyclobutanediol and 25 to 55 mole % 1,4-cyclohexanedimethanol; 50 to 75 mole % 2,2,4,4- tetramethyl-1,3-cyclobutanediol and 25 to 50 mole % 1,4-cyclohexanedimethanol; 55 to 75 mole % 2,2,4,4-tetramethyl-1,3-cyclobutanediol and 25 to 45 mole % 1,4-cyclohexanedimethanol; 60 to 75 mole % 2,2,4,4-tetramethyl-1,3-cyclobutanediol and 25 to 40 mole % 1,4-cyclohexanedimethanol; 65 to 75 mole % 2,2,4,4-tetramethyl-1,3-cyclobutanediol and 25 to 35 mole % 1,4-cyclohexanedimethanol; 40 to 70 mole % 2,2,4,4-tetramethyl-1,3-cyclobutanediol and 30 to 60 mole % 1,4-cyclohexanedimethanol; 45 to 70 mole % 2,2,4,4-tetramethyl-1,3-cyclobutanediol and 30 to 55 mole % 1,4-cyclohexanedimethanol; 50 to 70 mole % 2,2,4,4-tetramethyl-1,3-cyclobutanediol and 30 to 50 mole % 1,4-cyclohexanedimethanol; greater than 50 to 99 mole % 2,2,4,4-tetramethyl-1,3-cyclobutanediol and 1 to less than 50 mole % 1,4-cyclohexanedimethanol; greater than 50 to 80 mole % 2,2,4,4-tetramethyl-1,3-cyclobutanediol and 20 to less than 50 mole % 1,4-cyclohexanedimethanol; greater than 50 to 75 mole % 2,2,4,4-tetramethyl-1,3-cyclobutanediol and 25 to less than 50 mole % 1,4-cyclohexanedimethanol; greater than 50 to 70 mole % 2,2,4,4-tetramethyl-1,3-cyclobutanediol and 30 to less than 50 mole % 1,4-cyclohexanedimethanol; 55 to 70 mole % 2,2,4,4-tetramethyl-1,3-cyclobutanediol and 30 to 45 mole % 1,4-cyclohexanedimethanol; 60 to 70 mole % 2,2,4,4-tetramethyl-1,3-cyclobutanediol and 30 to 40 mole % 1,4-cyclohexanedimethanol; 40 to 65 mole % 2,2,4,4-tetramethyl-1,3-cyclobutanediol and 35 to 60 mole % 1,4-cyclohexanedimethanol; 40 to 55 mole % 2,2,4,4-tetramethyl-1,3-cyclobutanediol and 45 to 60 mole % 1,4-cyclohexanedimethanol; 40 to less than 45 mole % 2,2,4,4-tetramethyl-1,3-cyclobutanediol and greater than 55 to 60 mole % 1,4-cyclohexanedimethanol; 45 to 65 mole % 2,2,4,4-tetramethyl-1,3-cyclobutanediol and 35 to 55 mole % 1,4-cyclohexanedimethanol; greater than 50 to 65 mole % 2,2,4,4-tetramethyl-1,3-cyclobutanediol and 35 to less than 50 mole % 1,4-cyclohexanedimethanol.; 50 to 65 mole % 2,2,4,4-tetramethyl-1,3-cyclobutanediol and 35 to 50 mole % 1,4-cyclohexanedimethanol; 55 to 65 mole % 2,2,4,4-tetramethyl-1,3-cyclobutanediol and 35 to 45 mole % 1,4-cyclohexanedimethanol; 40 to 60 mole % 2,2,4,4-tetramethyl-1,3-cyclobutanediol and 40 to 60 mole % 1,4-cyclohexanedimethanol; 45 to 60 mole % 2,2,4,4-tetramethyl-1,3-cyclobutanediol and 40 to 55 mole % 1,4-cyclohexanedimethanol; 45 to 55 mole % 2,2,4,4-tetramethyl-1,3-cyclobutanediol and 45 to 55 mole % 1,4-cyclohexanedimethanol; greater than 45 to 55 mole % 2,2,4,4-tetramethyl-1,3-cyclobutanediol; 45 to less than 55 mole % 1,4-cyclohexanedimethanol; and 46 to 55 mole % 2,2,4,4-tetramethyl-1,3-cyclobutanediol and 45 to 54 mole % 1,4-cyclohexanedimethanol; and 46 to 65 mole % 2,2,4,4-tetramethyl-1,3-cyclobutanediol and 35 to 54 mole % 1,4-cyclohexanedimethanol.:

The polyesters useful in the polyester compositions of the thermoformed films and/or sheet(s) of the invention may be made from include 1,3-propanediol, or 1,4-butanediol, or mixtures thereof. It is contemplated that compositions of the invention made from 1,3-propanediol, 1,4-butanediol, or mixtures thereof can possess at least one of the Tg ranges described herein, at least one of the inherent viscosity ranges described herein, and/or at least one of the glycol or diacid ranges described herein. In addition or in the alternative, the polyesters made from 1,3-propanediol or 1,4-butanediol or mixtures thereof may also be made from 1,4-cyclohexanedimethanol in at least one of the following amounts: from 0.1 to less than 80 mole %; from 0.1 to 70 mole %; from 0.1 to 60 mole %; from 0.1 to 50 mole %; from 0.1 to 40 mole %; from 0.1 to 35 mole %; from 0.1 to 30 mole %; from 0.1 to 25 mole %; from 0.1 to 20 mole %; from 0.1 to 15 mole %; from 0.1 to 10 mole %; from 0.1 to 5 mole %; from 1 to less than 80 mole %; from 1 to 70 mole %; from 1 to 60 mole %; from 1 to 50 mole %; from 1 to 40 mole %; from 1 to 35 mole %; from 1 to 30 mole %; from 1 to 25 mole %; from 1 to 20 mole %; from 1 to 15 mole %; from 1 to 10 mole %; from 1 to 5 mole %; from 5 to less than 80 mole %; 5 to 70 mole %; from 5 to 60 mole %; from 5 to 50 mole %; from 5 to 40 mole %; from 5 to 35 mole %; from 5 to 30 mole %; from 5 to 25 mole %; from 5 to 20 mole %; and from 5 to 15 mole %; from 5 to 10 mole %; from 10 to less than 80 mole %; from 10 to 70 mole %; from 10 to 60 mole %; from 10 to 50 mole %; from 10 to 40 mole %; from 10 to 35 mole %; from 10 to 30 mole %; from 10 to 25 mole %; from 10 to 20 mole %; from 10 to 15 mole %; from 20 to less than 80 mole %; from 20 to 70 mole %; from 20 to 60 mole %; from 20 to 50 mole %; from 20 to 40 mole %; from 20 to 35 mole %; from 20 to 30 mole %; and from 20 to 25 mole %.

For embodiments of the invention, the polyesters useful in the invention may exhibit at least one of the following inherent viscosities as determined in 60/40 (wt/wt) phenol/tetrachloroethane at a concentration of 0.5 g/100 ml at 25° C.: 0.50 to 1.2 dL/g; 0.50 to 1.1 dL/g; 0.50 to 1 dug; 0.50 to less than 1 dL/g; 0.50 to 0.98 dL/g; 0.50 to 0.95 dL/g; 0.50 to 0.90 dL/g; 0.50 to 0.85 dL/g; 0.50 to 0.80 dL/g; 0.50 to 0.75 dL/g; 0.50 to less than 0.75 dL/g; 0.50 to 0.72 dL/g; 0.50 to 0.70 dL/g; 0.50 to less than 0.70 dL/g; 0.50 to 0.68 dL/g; 0.50 to less than 0.68 dL/g; 0.50 to 0.65 dL/g; 0.55 to 1.2 dL/g; 0.55 to 1.1 dL/g; 0.55 to 1 dL/g; 0.55 to less than 1 dL/g; 0.55 to 0.98 dL/g; 0.55 to 0.95 dL/g; 0.55 to 0.90 dL/g; 0.55 to 0.85 dL/g; 0.55 to 0.80 dL/g; 0.55 to 0.75 dL/g; 0.55 to less than 0.75 dL/g; 0.55 to 0.72 dL/g; 0.55 to 0.70 dL/g; 0.55 to less than 0.70 dL/g; 0.55 to 0.68 dL/g; 0.55 to less than 0.68 dL/g; 0.55 to 0.65 dL/g; 0.58 to 1.2 dL/g; 0.58 to 1.1 dL/g; 0.58 to 1 dL/g; 0.58 to less than 1 dL/g; 0.58 to 0.98 dL/g; 0.58 to 0.95 dL/g; 0.58 to 0.90 dL/g; 0.58 to 0.85 dL/g; 0.58 to 0.80 dL/g; 0.58 to 0.75 dL/g; 0.58 to less than 0.75 dL/g; 0.58 to 0.72 dL/g; 0.58 to 0.70 dL/g; 0.58 to less than 0.70 dL/g; 0.58 to 0.68 dL/g; 0.58 to less than 0.68 dL/g; 0.58 to 0.65 dL/g; 0.60 to 1.2 dug; 0.60 to 1.1 dL/g; 0.60 to 1 dL/g; 0.60 to less than 1 dL/g; 0.60 to 0.98 dL/g; 0.60 to 0.95 dug; 0.60 to 0.90 dL/g; 0.60 to 0.85 dL/g; 0.60 to 0.80 dL/g; 0.60 to 0.75 dL/g; 0.60 to less than 0.75 dL/g; 0.60 to 0.72 dL/g; 0.60 to 0.70 dL/g; 0.60 to less than 0.70 dL/g; 0.60 to 0.68 dL/g; 0.60 to less than 0.68 dL/g; 0.60 to 0.65 dL/g; 0.65 to 1.2 dL/g; 0.65 to 1.1 dL/g; 0.65 to 1 dL/g; 0.65 to less than 1 dL/g; 0.65 to 0.98 dL/g; 0.65 to 0.95 dL/g; 0.65 to 0.90 dL/g; 0.65 to 0.85 dL/g; 0.65 to 0.80 dL/g; 0.65 to 0.75 dL/g; 0.65 to less than 0.75 dL/g; 0.65 to 0.72 dL/g; 0.65 to 0.70 dL/g; 0.65 to less than 0.70 dL/g; 0.68 to 1.2 dL/g; 0.68 to 1.1 dL/g; 0.68 to 1 dL/g; 0.68 to less than 1 dL/g; 0.68 to 0.98 dL/g; 0.68 to 0.95 dL/g; 0.68 to 0.90 dL/g; 0.68 to 0.85 dL/g; 0.68 to 0.80 dL/g; 0.68 to 0.75 dL/g; 0.68 to less than 0.75 dL/g; 0.68 to 0.72 dL/g; greater than 0.76 dug to 1.2 dL/g; greater than 0.76 dug to 1.1 dL/g; greater than 0.76 dug to 1 dL/g; greater than 0.76 dug to less than 1 dL/g; greater than 0.76 dL/g to 0.98dL/g; greater than 0.76 dug to 0.95 dL/g; greater than 0.76 dL/g to 0.90 dL/g; greater than 0.80 dL/g to 1.2 dL/g; greater than 0.80 dL/g to 1.1 dL/g; greater than 0.80 dL/g to 1 dug; greater than 0.80 dL/g to less than 1 dL/g; greater than 0.80 dL/g to 1.2 dL/g; greater than 0.80 dL/g to 0.98dL/g; greater than 0.80 dL/g to 0.95 dL/g; greater than 0.80 dL/g to 0.90 dL/g.

It is contemplated that compositions useful in the thermoplastic articles of the invention can possess at least one of the inherent viscosity ranges described herein and at least one of the monomer ranges for the compositions described herein unless otherwise stated. It is also contemplated that compositions useful in the thermoplastic articles of the invention can posses at least one of the Tg ranges described herein and at least one of the monomer ranges for the compositions described herein unless otherwise stated. It is also contemplated that compositions useful in the thermoplastic articles of the invention can posses at least one of the inherent viscosity ranges described herein, at least one of the Tg ranges described herein, and at least one of the monomer ranges for the compositions described herein unless otherwise stated.

For the desired polyester, the molar ratio of cis/trans 2,2,4,4-tetramethyl-1,3-cyclobutanediol can vary from the pure form of each or mixtures thereof. In certain embodiments, the molar percentages for cis and/or trans 2,2,4,4,-tetramethyl-1,3-cyclobutanediol are greater than 50 mole % cis and less than 50 mole % trans; or greater than 55 mole % cis and up to 45 mole % trans; or 30 to 70 mole % cis and 70 to 30 % trans; or 40 to 60 mole % cis and 60 to 40 mole % trans; or 50 to 70 mole % trans and 50 to 30 % cis; or 50 to 70 mole % cis and 50 to 30 % trans; or 60 to 70 mole % cis and 30 to 40 mole % trans; or greater than 70 mole cis and up to 30 mole % trans; wherein the total sum of the mole percentages for cis- and trans-2,2,4,4-tetramethyl-1,3-cyclobutanediol is equal to 100 mole %. The molar ratio of cis/trans 1,4-cyclohexandimethanol can vary within the range of about 50/50 to 0/100, such as between 40/60 to 20/80.

Terephthalic acid or an ester thereof, such as, for example, dimethyl terephthalate, makes up the dicarboxylic acid component used to form the present polyester at a concentration of at least 70 mole %, such as at least 80 mole %, at least 90 mole % at least 95 mole %, at least 99 mole %, or 100 mole. Polyesters with higher amounts of terephthalic acid can possess higher impact strength properties. The terms "terephthalic acid" and "dimethyl terephthalate" are used interchangeably herein. In one embodiment, dimethyl terephthalate is part or all of the dicarboxylic acid component of the polyesters useful in the present invention. In all embodiments, ranges of from 70 to 100 mole %; or 80 to 100 mole %; or 90 to 100 mole %; or 99 to 100 mole %; or 100 mole % terephthalic acid and/or dimethyl terephthalate may be used.

In addition to terephthalic acid, the dicarboxylic acid component of the polyester useful in the invention can comprise up to 20 mole %, such as up to 10 mole %, up to 5 mole %, or up to 1 mole % of one or more modifying aromatic dicarboxylic acids. Certain embodiments can also contain 0.01 or more mole %, such as 0.1 or more mole %, 1 or more mole %, 5 or more mole %, or 10 or more mole % of one or more modifying aromatic dicarboxylic acids. Yet another embodiment contains 0 mole % modifying aromatic dicarboxylic acids. Thus, if present, it is contemplated that the amount of one or more modifying aromatic dicarboxylic acids can range from any of these preceding endpoint values including, for example, from 0.01 to 20 mole % and from 0.1 to 10 mole %. Modifying aromatic dicarboxylic acids which may be used in the present invention are those having up to 20 carbon atoms, and which are linear, para-oriented, or symmetrical. Examples of modifying aromatic dicarboxylic acids which may be used in this invention include, but are not limited to, isophthalic acid, 4,4'-biphenyldicarboxylic acid, 1,4-, 1,5-, 2,6-, 2,7-naphthalenedicarboxylic acid, and trans-4,4'-stilbenedicarboxylic acid, and esters thereof. In one embodiment, isophthalic acid is the modifying aromatic dicarboxylic acid.

The carboxylic acid component of the polyesters useful in the invention can be further modified with up to about 10 mole %, such as up to 5 mole % or up to 1 mole % of one or more of one or more aliphatic dicarboxylic acid containing 2-16 carbon atoms, such as, for example, malonic, succinic, glutaric, adipic, pimelic, suberic, azelaic and dodecanedioic dicarboxylic acids. Certain embodiments can also contain greater than 0.01 mole %, such as greater than 0.1 mole %, greater than 1 mole %, or greater than 5 mole % of one or more modifying aliphatic dicarboxylic acids. Yet another embodiment contains 0 mole % aliphatic dicarboxylic acids. Thus, if present, it is contemplated that the amount of one or more modifying aliphatic dicarboxylic acids can range from any of these preceding endpoint values including, for example, from 0.01 to 10 mole % and from 0.1 to 10 mole %. The total mole % of the dicarboxylic acid component is 100 mole %.

Esters of terephthalic acid and the other modifying dicarboxylic acids or their corresponding esters and/or salts may be used instead of the dicarboxylic acids. Suitable examples of dicarboxylic acid esters include, but are not limited to, the dimethyl, dipropyl, diisopropyl, dibutyl, and diphenyl esters.

The 1,4-cyclohexanedimethanol may be cis, trans, or a mixture thereof, for example, about a cis/trans ratio of 60:40 to 40:60. In another embodiment, the trans-1,4-cyclohexanedimethanol is present in the amount of 60 to 80 mole %.

The glycol component of the polyester portion of the polyester compositions useful in the invention can contain 25 mole % or less of one or more modifying glycols which are not 2,2,4,4-tetramethyl-1,3-cyclobutanediol or 1,4-cyclohexanedimethanol; in one embodiment, the polyesters useful in the invention may contain less than 15 mole % of one or more modifying glycols. In another embodiment, the polyesters useful in the invention can contain 10 mole % or less of one or more modifying glycols. In another embodiment, the polyesters useful in the invention can contain 5 mole % or less of one or more modifying glycols. In another embodiment, the polyesters useful in the invention can contain 3 mole % or less of one or more modifying glycols. In another embodiment, the polyesters useful in the invention can contain 0 mole % of one or more modifying glycols. Certain embodiments can also contain 0.01 or more mole %, such as 0.1 or more mole %, 1 or more mole %, 5 or more mole %, or 10 or more mole % of one or more modifying glycols. Thus, if present, it is contemplated that the amount of one or more modifying glycols can range from any of these preceding endpoint values including, for example, from 0.01 to 15 mole % and from 0.1 to 10 mole %.

Modifying glycols useful in the polyesters useful in the invention refer to diols other than 2,2,4,4-tetramethyl-1,3-cyclobutanediol and 1,4-cyclohexanedinethanol and may contain 2 to 16 carbon atoms. Examples of suitable modifying glycols include, but are not limited to, ethylene glycol, 1,2-propanediol, 1,3-propanediol, neopentyl glycol, 1,4-butanediol, 1,5-pentanediol, 1,6-hexanediol, p-xylene glycol or mixtures thereof. In one embodiment, the modifying glycol is ethylene glycol. In other embodiments, the modifying glycols are 1,3-propanediol and 1,4-butanediol. In another embodiment, ethylene glycol is excluded as a modifying diol. In another embodiment, 1,3-propanediol and 1,4-butanediol are excluded as modifying diols. In another embodiment, 2,2-dimethyl-1,3-propanediol is excluded as a modifying diol.

The polyesters and/or the polycarbonates useful in the invention can comprise from 0 to 10 weight percent (wt %), for example, from 0.01 to 5 weight percent, from 0.01 to 1 weight percent, from 0.05 to 5 weight percent, from 0.05 to 1 weight percent, or from 0.1 to 0.7 weight percent, based on the total weight of the polyester and/or polycarbonate, respectively, of one or more residues of a branching monomer, also referred to herein as a branching agent, having 3 or more carboxyl substituents, hydroxyl substituents, or a combination thereof. In certain embodiments, the branching monomer or agent may be added prior to and/or during and/or after the polymerization of the polyester. The polyester(s) useful in the invention can thus be linear or branched. The polycarbonate can also be linear or branched. In certain embodiments, the branching monomer or agent may be added prior to and/or during and/or after the polymerization of the polycarbonate.

The invention relates to a thermoplastic article having a decorative material embedded therein obtained by applying heat and pressure to one or more laminates wherein at least one of said laminates comprises, in order, (1) at least one upper sheet material, (2) at least one decorative material and (3) at least one lower sheet material; wherein the upper and lower sheet materials are formed from a miscible polyester/aromatic polycarbonate blend comprising:

(a) 1 to 99 weight % of a polyester, comprising
(1) a dicarboxylic acid component comprising
   i) from about 70 to 100 mole % of terephthalic acid residues;
   ii) 0 to about 30 mole % of an aromatic dicarboxylic residues having up to 20 carbon atoms; and
   iii) 0 to about 10 mole % of an aliphatic dicarboxylic acid residues having up to 16 carbon atoms; and
(2) a glycol component comprising:
   i) greater than 20 to 99 mole % of 2,2,4,4-tetramethyl-1,3-cyclobutanediol residues; and
   ii) about 1 to less than 80 mole % of 1,4-cyclohexanedimethanol residues,
   wherein the total mole % of the dicarboxylic acid component is 100 mole %, and
the total mole % of the glycol component is 100 mole %; and wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.
(b) 99 to 1 weight % of an aromatic polycarbonate;

wherein the total combined weight percentage of polyester and polycarbonate in the polyester/polycarbonate blend equals 100 weight %.

A preferred blend composition is 50-90 weight % by weight of the polyester and 50-10 weight % by weight of the aromatic polycarbonate. An even more preferred composition is 60-80 weight % polyester and 40-20 weight % by weight aromatic polycarbonate.

Polyesters suitable in certain embodiments of the present invention are polyesters having repeating unit of the Formula I:

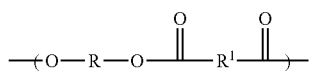

Formula I wherein R is the residue of 1,4 cyclohexanedimethanol or a mixture of 1,4 cyclohexanedimethanol and at least one aryl, alkane or cycloalkane containing diol having 2 to 20 carbon atoms or chemical equivalent thereof; and wherein $R^1$ is the decarboxylated residue derived from an aryl, aliphatic, or cycloalkane containing diacid of 3 to 20 carbon atoms or chemical equivalent thereof. Examples of the diol portion, R, are ethylene glycol, 1,2-propylene glycol, 1,3-propanediol, 1,4-butanediol, 1,5-pentanediol, 1,6-hexanediol, 1,2- or 1,3-cyclohexanedimethanol, neopentyl glycol, and 2,2,4,4 tetramethyl-1,3-cyclobutanediol. The preferred second glycol is ethylene glycol. Examples of the diacid portion, $R^1$, are malonic, succinic, glutaric, adipic, pimelic, suberic, azelaic, sebacic, dodecanedioic, 1,4-, 1,5-, and 2,6-decahydronaphthalenedicarboxylic acid, and cis- or trans-1,4-cyclohexanedicarboxylic acid. Examples of useful aromatic dicarboxylic acids are terephthalic acid, isophthalic acid, 4,4'-biphenyldicarboxylic, trans 3,3'-and trans 4,4 stilbenedicarboxylic acid, 4,4'-dibenzyldicarboxylic acid, 1,4-, 1,5'-, 2,3-, 2,6, and 2,7-naphthalenedicarboxylic acid. Chemical equivalents of these diacids include esters, alkyl esters, dialkyl esters, diaryl esters, anhydrides, salts, acid chlorides, acid bromides, and the like and are included within the scope of this invention. The preferred dicarboxylic acids are terephthalic and isophthalic acid or mixtures thereof. The preferred chemical equivalent comprises dialkyl esters of terephthalic and isophthalic acid. Mixtures of any of these acids or equivalents can be used.

Conventional polycondensation processes, well known in the art, are used to prepare the polyesters of the present invention. These include direct condensation of the acid(s) with the diol(s) or by ester interchange using lower alkyl esters. The inherent viscosity of the polyesters of the present invention may range from about 0.4 to 1.0 dl/g at 25° C. in a solvent consisting of 60% by weight phenol and 40% by weight tetrachloroethane.

The polymerization reaction may be carried out in the presence of one or more conventional polymerization catalysts. Typical catalysts or catalyst systems for polyester condensation are well known in the art. Suitable catalysts are disclosed, for example, in U.S. Pat. Nos. 4,025,492, 4,136,089, 4,176,224, 4,238,593, and 4,208,527, the disclosures of which are herein incorporated by reference. Further, R. E. Wilfong, Journal of Polymer Science, 54, 385, (1961) describes typical catalysts, which are useful in polyester condensation reactions. Preferred catalyst systems include Ti, Ti/P, Mn/Ti/Co/P, Mn/Ti/P, Zn/Ti/Co/P, Zn/Al, and Li/Al. When cobalt is not used in the polycondensation, copolymerizable toners may be incorporated into the copolyesters to control the color of these copolyesters so that they are suitable for the intended applications where color may be an important property. In addition to the catalysts and toners, other conventional additives, such as antioxidants, dyes, etc., may be used in the copolyesterifications in typical amounts.

One or more branching agents may also be useful in making the polyesters formed within the context of the invention. The branching agent can be one which provides branching in the acid unit portion of the polyester, or in the glycol unit portion, or it can be a hybrid. Some of these branching agents have already been described herein. However, illustrative of such branching agents are polyfunctional acids, polyfunctional glycols and acid/glycol hybrids. Examples of multifunctional acids and multifunctional alcohols include tri or tetracarboxylic acids, such as trimesic acid, trimellitic acid, citric acid, tartaric acid, 3-hydroxyglutaric acid and pyromellitic acid and lower alkyl esters thereof and the like, and tetrols such as pentaerythritol. Also triols such as trimethylolpropane or dihydroxy carboxylic acids and hydroxydicarboxylic acids and derivatives, such as dimethyl hydroxy terephthalate, and the like are useful within the context of this invention. Trimellitic anhydride is a preferred branching agent. In one embodiment, the branching monomer residues comprise about 0.1 to about 0.7 mole percent of one or more residues of: trimellitic anhydride, pyromellitic dianhydride, glycerol, sorbitol, 1,2,6-hexanetriol, pentaerythritol, trimethylolethane, or trimesic acid. The branching monomer may be added to the polyester reaction mixture or blended with the polyester in the form of a concentrate as described, for example, in U.S. Pat. Nos. 5,654,347 and 5,696,176, the disclosure regarding branching monomers which is incorporated herein by reference. The branching agents may be used either to branch the polyester itself or to branch the polyester/polycarbonate blend of the invention.

Glass transition temperature (Tg) was determined using a TA DSC 2920 from Thermal Analyst Instrument at a scan rate of 20° C./min.

Because of the long crystallization half-times (e.g., greater than 5 minutes) at 170° C. exhibited by certain polyesters useful in the present invention, it is possible to produce the thermoplastic articles of the invention. Certain polyesters useful in the invention are "amorphous" which is defined herein as having a crystallization half-time of greater than 5 minutes at 170° C. In one embodiment, of the invention, the crystallization half-times are greater than 1,000 minutes at 170° C.

In another embodiment of the invention, the crystallization half-times of the polyesters useful in the invention are greater than 10,000 minutes at 170° C. The crystallization half time of the polyester, as used herein, may be measured using methods well-known to persons of skill in the art. The crystallization half time of the polyester, $t_{1/2}$, was determined by measuring the light transmission of a sample via a laser and photo detector as a function of time on a temperature controlled hot stage. This measurement was done by exposing the polymers to a temperature, $T_{max}$, and then cooling it to the desired temperature. The sample was then held at the desired temperature by a hot stage while transmission measurements were made as a function of time. Initially, the sample was visually clear with high light transmission and became opaque as the sample crystallizes. The crystallization half-time is the time at which the light transmission was halfway between the initial transmission and the final transmission. $T_{max}$ is defined as the temperature required to melt the crystalline domains of the sample (if crystalline domains are present). The sample is heated to Tmax to condition the sample prior to crystallization half time measurement. The absolute Tmax temperature is different for each composition. For example PCT would need to be heated to some temperature greater than 290 C to melt the crystalline domains.

As shown in Table 1 and FIG. 1 of the Examples, 2,2,4,4-tetramethyl-1,3-cyclobutanediol is more effective than other comonomers such ethylene glycol and isophthalic acid at increasing the crystallization half-time, i.e., the time required for a polymer to reach half of its maximum crystallinity. By decreasing the crystallization rate of PCT, i.e. increasing the crystallization half-time, amorphous articles based on modified PCT may be fabricated by methods known in the art such as extrusion, injection molding, and the like. As shown in Table 1, these materials can exhibit higher glass transition temperatures and lower densities than other modified PCT copolyesters.

The polyesters can exhibit an improvement in toughness combined with processability for some of the embodiments of the invention. Specifically, it is unexpected that lowering the inherent viscosity slightly of the polyesters useful in the invention results in a more processable melt viscosity while retaining good physical properties of the polyesters such as toughness and heat resistance.

Figure 2:
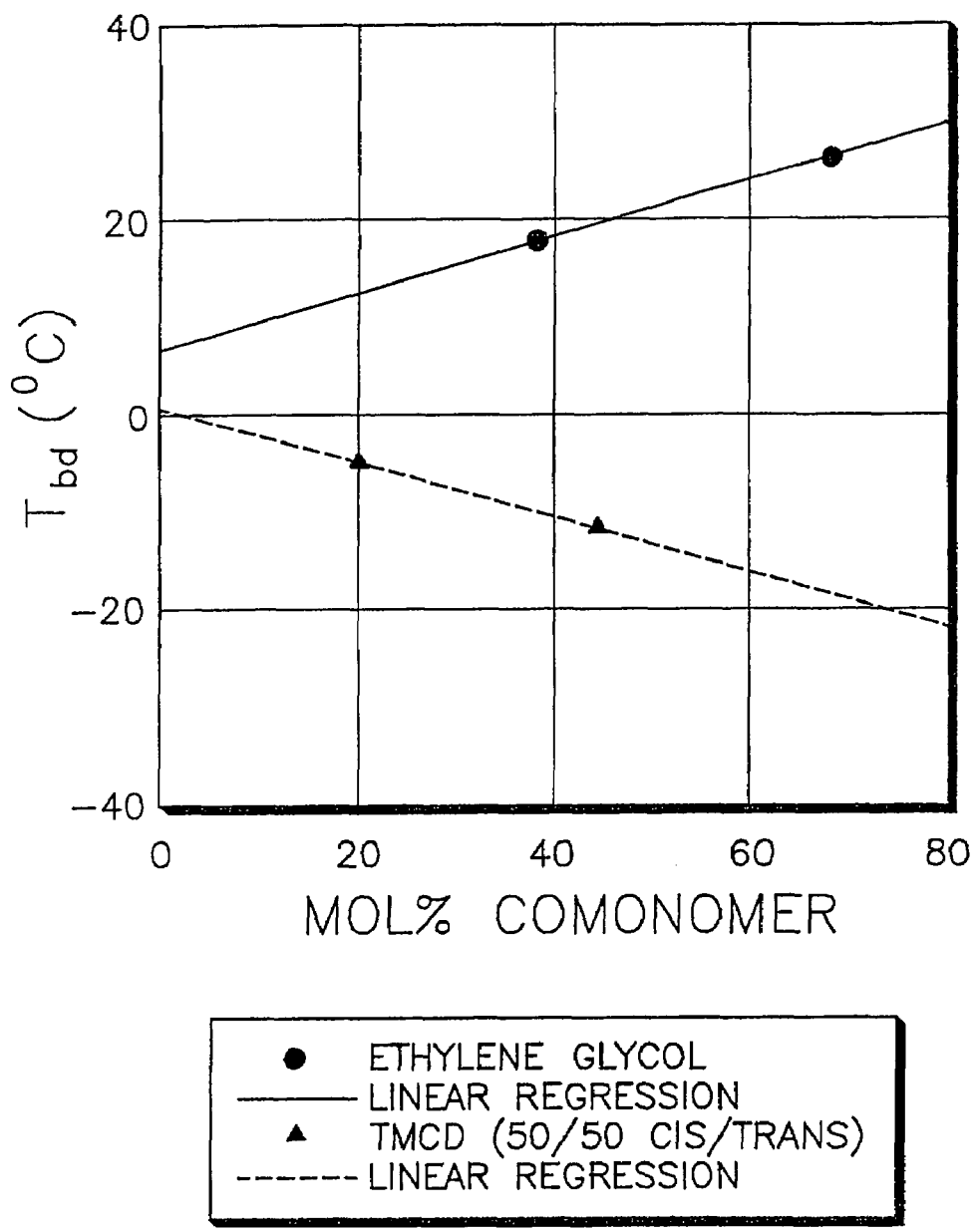
FIG. 2 is a graph showing the effect of comonomer on the brittle-to-ductile transition temperature ($T_{bd}$) in a notched Izod test (ASTM D256, ⅛-in thick, 10-mil notch).

It is known that increasing the content of 1,4-cyclohexanedimethanol in a copolyester based on terephthalic acid, ethylene glycol, and 1,4-cyclohexanedimethanol improves toughness as determined by the brittle-to-ductile transition temperature in a notched Izod test as measured by ASTM D256. This toughness improvement, by lowering of the brittle-to-ductile transition temperature with 1,4-cyclohexanedimethanol, is believed to occur due to the flexibility and conformational behavior of 1,4-cyclohexanedimethanol in the copolyester. Incorporating 2,2,4,4-tetramethyl-1,3-cyclobutanediol into PCT continues to improve toughness, by lowering the brittle-to-ductile transition temperature, as shown in Table 2 and FIG. 2 of the Examples. This is unexpected given the rigidity of 2,2,4,4-tetramethyl-1,3-cyclobutanediol.

Certain polyesters useful I the invention have a melt viscosity of less than about 30,000 poise such as less than about 20,000 poise, as measure at 1 radian/second on a rotary melt rheometer at 290° C.

In one embodiment, the polyesters useful in this invention can be visually clear. The term "visually clear" is defined herein as an appreciable absence of at least one of cloudiness, haziness, and/or muddiness, when inspected visually. When the polyesters are blended with polycarbonate, including bisphenol A polycarbonates, the blends can be visually clear in one aspect of the invention.

In other embodiments, the polyesters useful in the invention may have a yellowness index (ASTM D-1925) of less than about 50 or less than about 20.

The thermoplastic articles of the invention may be formed without the need to dry the sheet(s) and/or film(s). Even without the drying the thermoplastic articles prior to forming, the presence of "blisters" or air bubble forming in the thermoplastic article is avoided.

The present polyesters possess one or more of the following properties. These properties include a notched Izod strength of at least 3 ft-lb/in at 23° C. with a 10-mil notch in a ⅛-inch thick bar determined according to ASTM D256; in one embodiment, the polyesters useful in the invention exhibit a notched Izod impact strength of at least 10 ft-lb/in at 23° C. with a 10-mil notch in a ⅛-inch thick bar determined according to ASTM D256; in one embodiment, the polyesters useful in the invention exhibit a notched Izod impact strength of at least 11 ft-lb/in at 23° C. with a 10-mil notch in a ⅛-inch thick bar determined according to ASTM D256; in one embodiment, the polyesters useful in the invention exhibit a notched Izod impact strength of at least 12 ft-lb/in at 23° C. with a 10-mil notch in a ⅛-inch thick bar determined according to ASTM D256; in one embodiment, the polyesters useful in the invention exhibit a notched Izod impact strength of at least 13 ft-lb/in at 23° C. with a 10-mil notch in a ⅛-inch thick bar determined according to ASTM D256; in one embodiment, the polyesters useful in the invention exhibit a notched Izod impact strength of greater than 13 ft-lb/in at 23° C. with a 10-mil notch in a ⅛-inch thick bar determined according to ASTM D256; in one embodiment, the polyesters useful in the invention exhibit a notched Izod impact strength of at least 15 ft-lb/in at 23° C. with a 10-mil notch in a ⅛-inch thick bar determined according to ASTM D256; in one embodiment, the polyesters useful in the invention exhibit a notched Izod impact strength of at least 16 ft-lb/in at 23° C. with a 10-mil notch in a ⅛-inch thick bar determined according to ASTM D256. In one embodiment, the polyesters useful in the invention exhibit a notched Izod impact strength of at least 3 ft-lb/in at 23° C. with a 10-mil notch in a ¼-inch thick bar determined according to ASTM D256.

In another embodiment, certain polyesters useful in the invention exhibit an increase in notched Izod impact strength when measured at 0° C. of at least 3% or at least 5% or at least 10% or at least 15% as compared to the notched Izod impact strength when measured at −5° C. with a 10-mil notch in a ⅛-inch thick bar determined according to ASTM D256. In addition, certain other polyesters also exhibit a retention of notched Izod impact strength within plus or minus 5% when measured at 0° C. through 30° C. with a 10-mil notch in a ⅛-inch thick bar determined according to ASTM D256.

In one embodiment, polyesters of this invention exhibit superior notched toughness in thick sections. Notched Izod impact strength, as described in ASTM D256, is a common method of measuring toughness. When tested by the Izod method, polymers can exhibit either a complete break failure mode, where the test specimen breaks into two distinct parts, or a partial or no break failure mode, where the test specimen remains as one part. The complete break failure mode is associated with low energy failure. The partial and no break failure modes are associated with high energy failure. A typical thickness used to measure Izod toughness is ⅛". At this thickness, very few polymers are believed to exhibit a partial or no break failure mode, polycarbonate being one notable example. When the thickness of the test specimen is increased to ¼", however, no commercial amorphous materials exhibit a partial or no break failure mode. In one embodiment, compositions of the present example exhibit a no break failure mode when tested in Izod using a ¼" thick specimen.

In yet another embodiment, certain polyesters useful in the invention exhibit a retention in notched Izod impact strength with a loss of no more than 70% when measured at 23° C. with a 10-mil notch in a ¼-inch thick bar determined according to ASTM D256 as compared to notched Izod impact strength for the same polyester when measured at the same temperature with a 10-mil notch in a ⅛-inch thick bar determined according to ASTM D256.

In one embodiment, the polyesters useful in the invention exhibit a ductile-to-brittle transition temperature of less than 0° C. based on a 10-mil notch in a ⅛-inch thick bar as defined by ASTM D256.

In one embodiment, the polyesters useful in the invention exhibit a density of <1.20 g/ml at 23° C.; and in another embodiment, a density of <1.18 g/ml at 23° C.

In one embodiment, the polyesters useful in the invention, when toner is not present, have color values L*, a* and b* were determined using a Hunter Lab Ultrascan Spectra Colorimeter manufactured by Hunter Associates Lab Inc., Reston, Va. The colors determinations are taken at random locations on the sample and averaged. They are determined by the L*a*b* color system of the CIE (International Commission on Illumination) (translated), wherein L* represents the lightness coordinate, a* represents the red/green coordinate, and b* represents the yellow/blue coordinate. In certain embodiments, the b* values for the polyesters useful in the invention can be from 0 to less than 10 and the L* values can be from 50 to 90. In other embodiments, the b* values for the polyesters useful in the invention can be present in one of the following ranges: from 0 to 9; 0 to 8; 0 to 7; 0 to 6; 0 to 5; 0 to 4; 0 to 3; 0 to 2; 1 to 10; 1 to 9; 1 to 8; 1 to 7; 1 to 6; 1 to 5; 1 to 4; 1 to 3; and 1 to 2. In other embodiments, the L* value for the polyesters useful in the invention can be present in one of the following ranges: 50 to 60; 50 to 70; 50 to 80; 50 to 90; 60 to 70; 60 to 80; 60 to 90; 70 to 80; 79 to 90.

The polyester portion of the polyester composition useful in the invention can be made by processes known from the literature such as, for example, by processes in homogenous solution, by transesterification processes in the melt, and by two phase interfacial processes. Suitable methods include the steps of reacting one or more dicarboxylic acids with one or more glycols at a temperature of about 100° C. to 315° C. at a pressure of about 0.1 to 760 mm Hg for a time sufficient to form a polyester. See U.S. Pat. No. 3,772,405 for methods of producing polyesters, the disclosure of such methods which is incorporated herein by reference.

In another aspect, the invention relates to thermoplastic articles comprising a polyester produced by a process comprising:
(I) heating a mixture comprising the monomers useful in any of the polyesters in the invention in the presence of a catalyst at a temperature of about to 240° C. for a time sufficient to produce an initial polyester;
(II) heating the initial polyester of step (I) at a temperature of 240 to 320° C. for about 1 to 4 hours; and
(III) removing any unreacted glycols.

Suitable catalysts for use in this process include organozinc or tin compounds. The use of this type of catalyst is well known in the art. Examples of catalysts useful in the present invention include, but are not limited to, zinc acetate, butyltin tris-2-ethylhexanoate, dibutyltin diacetate, and dibutyltin oxide. Other catalysts may include those based on titanium, zinc, manganese, lithium, germanium, and cobalt. Catalyst amounts typically range from about 10 ppm to about 500 ppm based on the catalyst metal. The process can be carried out in a batch or continuous process.

Typically, step (I) is carried out until about 50% by weight or more of the 2,2,4,4-tetramethyl-1,3-cyclobutanediol has been reacted. Step (I) maybe carried out under pressure, ranging from atmospheric pressure to 100 psig. The term "reaction product" as used in connection with any of the catalysts useful in the invention refers to any product of a polycondensation and/or esterification reaction with the catalyst and any of the monomers used in making the polyester as well as the product of a polycondensation or esterification reaction between the catalyst and any other type of additive.

Typically, Step (II) and Step (III) can be conducted at the same time. These steps can be carried out by methods known in the art such as by placing the reaction mixture under a pressure ranging, from 0.002 psig to atmospheric pressure, or by blowing hot nitrogen gas over the mixture.

The invention further relates to a polyester product made by the process described above.

The invention further relates to a polymer blend. The blend comprises:
(a) from about 5 to 95 wt % of the polyesters described above; and
(b) from about 5 to 95 wt % of a polymeric component.

Suitable examples of the polymeric component include, but are not limited to, NYLON 6,6® from DuPont; poly (ether-imides) such as ULTEM® (a poly(ether-imide) from General Electric); polyphenylene oxides such as poly(2,6-dimethylphenylene oxide) or poly(phenylene oxide)/polystyrene blends such as NORYL 1000® (a blend of poly(2,6-dimethylphenylene oxide) and polystyrene resins from General Electric); other polyesters; polyphenylene sulfides; polyphenylene sulfide/sulfones; poly(ester-carbonates); polycarbonates such as LEXAN® (a polycarbonate from General Electric); polysulfones; polysulfone ethers; and poly (ether-ketones) of aromatic dihydroxy compounds. The blends can be prepared by conventional processing techniques known in the art, such as melt blending or solution blending. In one embodiment, it is preferred that polycarbonate is not present in the polyester composition. If polycarbonate is used in a blend in the polyester compositions useful in the invention, the blends would be expected to be visually clear. However, the polyester compositions useful in the invention contemplate the excluding of polycarbonate from the polyester compositions.

Polycarbonates useful in this invention comprise the divalent residue of dihydric phenols bonded through a carbonate linkage and are represented by structural formulae II and III.

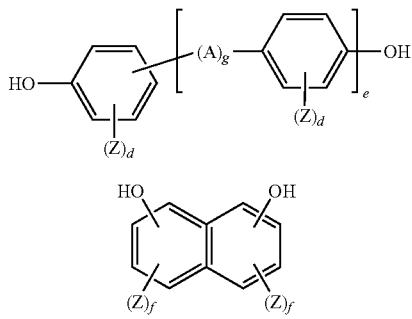

Formula II

Formula III wherein:

A denotes an alkylene group with 1 to 8 carbon atoms; an alkylidene group with 2 to 8 carbon atoms; a cycloalkylene group with 5 to 15 carbon atoms; a cycloalkylidene group with 5 to 15 carbon atoms; a carbonyl group; an oxygen atom; a sulfur atom; —SO— or —SO$_2$; or a radical conforming to e and g both denote the number 0 to 1; Z denotes F, Cl, Br or $C_{1-4}$.alkyl; and if several Z radicals are substituents in one aryl radical, they may be identical or different from one another; d denotes an integer of from 0 to 4; and f denotes an integer of from 0 to 3.

By the term "alkylene" is meant a bivalent saturated aliphatic radical wherein the two valences are on different carbon atoms, e.g., ethylene,; 1,3-propylene; 1,2-propylene; 1,4-butylene; 1,3-butylene; 1,2- butylene, amylene, isoamylene, etc. By the term "alkylidene" is meant a bivalent radical wherein the two valences are on the same carbon atoms, e.g., ethylidene, propylidene, isopropylidine, butylidene, isobutylidene, amylidene, isoamylidene, 3,5,5,-trimethylhexylidene. Examples of "cycloalkylene" are cyclopropylene, cyclobutylene, and cyclohexylene. Examples of "cycloalkylidene" are cyclopropylidene, cyclobutylidene, and cyclohexylidene. Examples of $C_{1-4}$.alkyl are methyl, ethyl, propyl, isopropyl, butyl, and isobutyl.

The dihydric phenols employed are known, and the reactive groups are thought to be the phenolic hydroxyl groups. Typical of some of the dihydric phenols employed are bisphenols such as 2,2-bis-(4-hydroxyphenyl)-propane (bisphenol A), 3,3,5-trimethyl-1,1-bis(4-hydroxyphenyl)-cyclohexane, 2,4-bis-(4-hydroxyphenyl)-2-methyl-butane, 1,1-bis-(4-hydroxyphenyl)-cyclohexane, alpha, alpha'-bis-(4-hydroxyphenyl)-p-diisopropylbenzene, 2,2-bis-(3-methyl4-hydroxyphenyl)-propane, 2,2-bis-(3-chloro-4-hydroxyphenyl)propane, bis-(3,5-dimethyl4-hydroxyphenyl)-methane, 2,2-bis-(3,5-dimethyl-4-hydroxyphenyl)-propane, bis-(3,5-dimethyl-4-hydroxyphenyl )-sulfide, bis-(3,5dimethyl-4-hydroxyphenyl)-sulfoxide, bis-(3,5-dimethyl-4-hydroxyphenyl )-sulfone, dihydroxy-benzophenone, 2,4-bis-(3,5-dimethyl-4-hydroxyphenyl)-cyclohexane, alpha, alpha'-bis-(3,5-dimethyl-4-hydroxyphenyl)-p-diisopropylbenzene and 4,4'-sulfonyl diphenol. Other dihydric phenols might include hydroquinone, resorcinol, bis-(hydroxyphenyl)-alkanes, bis-(hydroxyphenyl)ethers, bis-(hydroxyphenyl)-ketones, bis-(hydroxyphenyl)-sulfoxides, bis-(hydroxyphenyl)-sulfides, bis-(hydroxyphenyl)-sulfones, and alpha, alpha.-bis-(hydroxyphenyl)diisopropylbenzenes, as well as their nuclear-alkylated compounds. These and further suitable dihydric phenols are described, for example, in U.S. Pat. Nos. 2,991,273; 2,999,835; 2,999,846; 3,028,365; 3,148,172; 3,153,008; 3,271,367; 4,982,014; 5,010,162 all incorporated herein by reference. The polycarbonates of the invention may entail in their structure, units derived from one or more of the suitable bisphenols. The most preferred dihydric phenol is 2,2-bis-(4-hydroxyphenyl)-propane (bisphenol A).

The carbonate precursors are typically a carbonyl halide, a diarylcarbonate, or a bishaloformate. The carbonyl halides include, for example, carbonyl bromide, carbonyl chloride, and mixtures thereof. The bishaloformates include the bishaloformates of dihydric phenols such as bischloroformates of 2,2-bis(4-hydroxyphenyl)-propane, hydroquinone, and the like, or bishaloformates of glycol, and the like. While all of the above carbonate precursors are useful, carbonyl chloride, also known as phosgene, and diphenyl carbonate are preferred.

The aromatic polycarbonates can be manufactured by any processes such as by reacting a dihydric phenol with a carbonate precursor, such as phosgene, a haloformate or carbonate ester in melt or solution. Suitable processes are disclosed in U.S. Pat. Nos. 2,991,273; 2,999,846; 3,028,365; 3,153,008; 4,123,436; all of which are incorporated herein by reference. Polycarbonates useful in the invention may be prepared according to other known procedures, for example, by reacting the dihydroxyaromatic compound with a carbonate precursor such as phosgene, a haloformate or a carbonate ester, a molecular weight regulator, an acid acceptor and a catalyst. Methods for preparing polycarbonates are known in the art and are described, for example, in U.S. Pat. No. 4,452,933, whose disclosure regarding preparation of polycarbonates is hereby incorporated by reference herein.

Examples of suitable carbonate precursors include, but are not limited to, carbonyl bromide, carbonyl chloride, or mixtures thereof; diphenyl carbonate; a di(halophenyl)carbonate, e.g., di(trichlorophenyl) carbonate, di(tribromophenyl) carbonate, and the like; di(alkylphenyl)carbonate, e.g., di(tolyl) carbonate; di(naphthyl)carbonate; di(chloronaphthyl)carbonate, or mixtures thereof; and bis-haloformates of dihydric phenols.

Examples of suitable molecular weight regulators include, but are not limited to, phenol, cyclohexanol, methanol, alkylated phenols, such as octylphenol, para-tertiary-butyl-phenol, and the like. In one embodiment, the molecular weight regulator is phenol or an alkylated phenol.

The acid acceptor may be either an organic or an inorganic acid acceptor. A suitable organic acid acceptor is a tertiary amine and includes such materials as pyridine, triethylamine, dimethylaniline, tributylamine, and the like. The inorganic acid acceptor can be either a hydroxide, a carbonate, a bicarbonate, or a phosphate of an alkali or alkaline earth metal.

The catalysts that can be used are those that typically aid the polymerization of the monomer with phosgene. Suitable catalysts include, but are not limited to, tertiary amines such as triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethyl ammonium chloride, tetra-methyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

The polycarbonates useful in the polyester compositions which are useful in the invention also may be copolyestercarbonates such as those described in U.S. Pat. Nos. 3,169,121; 3,207,814; 4,194,038; 4,156,069; 4,430,484, 4,465,820, and 4,981,898, the disclosure regarding copolyestercarbonates from each of them is incorporated by reference herein.

Copolyestercarbonates useful in this invention can be available commercially or can be prepared by known methods in the art. For example, they are typically obtained by the reaction of at least one dihydroxyaromatic compound with a mixture of phosgene and at least one dicarboxylic acid chloride, especially isophthaloyl chloride, terephthaloyl chloride, or both.

In addition, the polyester compositions and the polymer blend compositions useful in the thermoformed film(s) and/or sheet(s) of this invention may also contain from 0.1 to 25% by weight of the overall composition common additives such as colorants, mold release agents, flame retardants, plasticizers, nucleating agents, stabilizers, including but not limited to, UV stabilizers, thermal stabilizers, fillers, and impact modifiers. Residues of such additives are also contemplated as part of the polyester composition.

Examples of typical commercially available impact modifiers well known in the art and useful in this invention include, but are not limited to, ethylene/propylene terpolymers, styrene-based block copolymeric impact modifiers, and various acrylic core/shell type impact modifiers.

Thermal stabilizers are compounds known to be effective in stabilizing polyesters during melt processing including but not limited to phosphoric acid, phosphorous acid, phosphonic acid, phosphinic acid, phosphonous acid, and various esters and salts thereof. The esters can be alkyl, branched alkyl, substituted alkyl, difunctional alkyl, alkyl ethers, aryl, and substituted aryl. The number of ester groups present in the particular phosphorus compound can vary from zero up to the maximum allowable based on the number of hydroxyl groups present on the phosphorus compound used. In one embodiment, triphenyl phosphate is particularly effective as a thermal stabilizer. The term "reaction product" as used in connection with the thermal stabilizers of the invention refers to any product of a polycondensation and/or esterification reaction between the thermal stabilizer and any of the monomers used in making the polyester as well as the product of a polycondensation or esterification reaction between the catalyst and any other type of additive.

The polycarbonates of this invention have a weight average molecular weight, as determined by gel permeation chromatography, of about 10,000 to 200,000, preferably 15,000 to 80,000 and their melt flow index, per ASTM D-1238 at 300° C. is about 1 to 65 g/10 min, preferably about 2 to 30 g/10 min. The polycarbonates may be branched or unbranched. It is contemplated that the polycarbonate may have various known end groups. These resins are known and are readily available in commerce.

One or more branching agents may also be used in making the polycarbonates of the invention. Branching agents, such as tri- and tetrafunctional phenols and carbonic acids, as well as bisphenols with carbonic acid side chains are typically used. An example might include 1,4-bis(4',4"-dihydroxytriphenylmethyl)benzene, and trisphenol TC. Nitrogen-containing branching agents are also used. Examples might include: cyanic chloride and 3,3-bis(4-hydroxyphenyl)-2-oxo-2,3-dihydroindole. Polymer miscibility is defined herein as a polymer forming a single phase.

While a preferred embodiment of the invention is the "sandwich" embodiment described herein consisting of upper sheet material (1), decorative layer (2) and lower sheet material (3), it is also within the scope of this invention that multiple "sandwiches" can be present with the "sandwiches" simply being replicated. It is further within the scope of this invention that the multiple "sandwiches" embodiment shares one layer in common, namely, layers (1) or (3), i.e., such as a laminate consisting of the following layers, in order: sheet material, decorative layer, sheet material, decorative layer, sheet material, etc.

Optionally, an adhesive layer may be used between the upper sheet material (1) and the decorative layer (2) and/or between the lower sheet material (3) and the decorative layer (2). In the multilaminate embodiments, an adhesive layer can also be applied between laminates. The adhesive layer can comprise any adhesive known in the art. Specific examples within the scope of this invention are polyurethane, modified polyethylenes, sulfopolyesters, epoxy coatings all of which are known in the art. Sulfopolyesters useful as adhesives in the practice of this invention can be either linear or branched. Preferred sulfopolyesters have a glass transition temperature (denoted as Tg) between −25° C. and +90° C. More preferred sulfopolyesters have a Tg between 0° C. and +65° C. Even more preferred sulfopolyesters have a Tg between +5° C. and +55° C. Useful sulfopolyesters and their methods of preparation are described in U.S. Pat. Nos. 3,546,008; 3,734,874; 4,233,196; 4,946,932; 5,543,488; 5,552,495; 5,290,631; 5,646,237; 5,709,940; and 6,162,890. Alternatively, water dispersible phosphopolyesters, such as those described in U.S. Pat. No. 4,111,846 can be used advantageously but these polymers suffer from a lack of hydrolytic stability in aqueous systems and are, therefore, less desirable for practical use.

In addition to the preferred Tg ranges delineated above, useful sulfopolyesters have an inherent viscosity (a measure of molecular weight) of a least 0.1 and preferably at least 0.2 and more preferably at least 0.3 as measured in a 60/40 parts by weight solution of phenol/tetrachloroethane at 25° C. and a concentration of about 0.25 grams of polymer in 100 mL of solvent. For branched sulfopolyesters, such as those described in U.S. Pat. No. 5,543,488, preferred compositions have a number-average-molecular weight (Mn) of at least 4000 Daltons.

The polyester/polycarbonate blends of this invention maybe made by conventional melt processing techniques. For examples, pellets of the polyester may be mixed with pellets of the polycarbonate and subsequently melt blended on either a single or twin screw extruder to form a homogenous mixture.

The miscible blend compositions of the invention may contain impact modifiers, UV stabilizers, stabilizers, nucleating agents, extenders, flame retarding agents, reinforcing agents, fillers, antistatic agents, mold release agents, colorants, antioxidants, extrusion aids, slip agents, release agents, carbon black, and other pigments, and the like all and mixtures thereof which are known in the art for their utility in polyester/polycarbonate blends. In particular, the use of phosphorous based stabilizers for further color reductions, if needed, is well known in the art.

The second component of the thermoplastic articles of the present invention comprises a decorative material, which may be natural or synthetic. The decorative material may include, but is not limited to, metallic wire, rods or bars; natural fibers, glass fibers, mineral fibers, fabric, papers; printed layers, wood, stone, photographic images, wood chips, grasses, vegetation, thatch, bamboo, tree or bush branches or stems, will reed leaves, beans, flowers, flower petals, wheat, grains, crushed glass.

For instance, fabric may be used as a decorative material to be encapsulated. The fabric may display images or decorative designs that have been produced, e.g., by weaving or knitting techniques, in the fabric. The fabrics, which may be used in producing the articles of the present invention, comprise textile fibers, i.e., fibers of natural-occurring, semisynthetic or synthetic polymeric materials. For example, the fabrics may be prepared from cotton, wool, silk, rayon (regenerated cellulose), polyester such as poly(ethylene terephthalate), synthetic polyamides such as nylon 66 and nylon 6, synthetic polyolefins such as polyethylene and polypropylene, acrylic, modacrylic and cellulose acetate fibers. The melting point of the textile fibers should be sufficiently high to avoid any degradation or distortion of the fabric during the manufacture or processing of the articles of this invention. The fabric may be woven, spun-bonded, knitted, or prepared by other processes well known in the textile trade and may be uncolored, e.g., white, or colored by conventional dyeing and printing techniques. Alternatively, the fabrics may be produced from dyed yarn or from filaments and yarn derived from mass colored polymers. Normally, the fabrics present within the thermoplastic articles of the present invention are substantially continuous and constitute a distinct layer. One embodiment of our invention, therefore, is a novel laminate article comprising, in order, (1) a layer of a miscible polyester/polycarbonate blend, (2) a fabric layer composed or made of textile fibers, and (3) a second layer of a miscible polyester/polycarbonate blend as described hereinabove.

As another example, the second component (decorative component) of the thermoplastic articles of the present invention may comprise metallic wire, rod or bar. The metal wire may be formed by a variety of techniques to produce metal mesh fabric, screens, or open mesh having high transparency. The metal wire, rod or bar may be woven, welded, knitted, or fabricated by means of other processes well known in the metal wire fabrication trade. The metallic wire, rod and bar may be of various colors such as black, gray, green, blue, etc. The metallic element can be composed of different metallic materials such copper, aluminum, stainless steel, steel, galvanized steel, titanium, etc. or combinations thereof. The metallic component of the thermoplastic articles may be prepared from wire filaments, rods and bars having various cross-sectional areas and geometries, e.g., generally circular, oval or relatively flat. The thickness or diameter of the wire, rod and bar may range from about 0.001 to 19 mm (0.00004 to 0.75 inch) depending upon the end use of the thermoplastic article. However, for most of the articles of the present invention the thickness or diameter the wire, rod and bar will be in the range of about 0.0254 to 5.08 mm (0.001 to 0.20 inch). One embodiment of our invention, therefore, is a novel laminate article comprising, in order, (1) a layer of a miscible polyester/polycarbonate blend, (2) a metal wire mesh, and (3) a second layer of a miscible polyester/polycarbonate blend is described hereinabove.

Still further, the decorative component may be decorative or printed papers, colored films, films printed with an image or picture, and the like.

The thermoplastic articles of our invention can be used in the manufacture of decorative walls, partitions, and glazing applications. The thermoplastic articles are thermoformable according to methods known in the art of thermoforming.

The upper and lower sheet materials used in the manufacture of the thermoplastic articles of the present invention may be the same or different. For example, the upper and lower sheet materials may be produced from different miscible polyester/polycarbonate blends (as defined herein) or miscible compositions that contain different additives, e.g., pigment additives that alter the transparency of the miscible polyester/polycarbonate sheeting.

The sheet material used in the preparation of the thermoplastic articles of our invention may be transparent, translucent, or one layer may be opaque, depending on the particular aesthetic effect desired. The upper and lower sheet materials may differ in degree of transparency or translucency and also in color. When the upper and lower sheet materials are produced from different miscible polyester/polycarbonate blends, the miscible polyester/polycarbonate blends must be thermally compatible. As used herein, the term "thermal compatibility" means that when layers of the sheet materials are bonded together under conditions of elevated temperature and pressure, the layers undergo approximately equal thermal expansion or contraction such that the solid surface is substantially planar.

The thickness of the sheet materials used in the preparation of the thermoplastic articles is not an important feature of the present invention and depends upon a number of factors such as functionality, weight, cost and the like. The sheet material from which the upper (or outer) layer or surface is formed generally has a thickness in the range of about 0.76 to 6.4 mm (0.03-0.25 inch), preferably in the range of about 1.6 to 3.2 mm (0.063-0.126 inch). The sheet material from which the lower (or backing) layer or surface is formed typically has a thickness in the range of about 0.76 to 6.4 mm (0.03-0.25 inch), preferably about 3.2 mm (0.126 inch).

The thermoplastic article of the present invention may be produced by subjecting the laminate to temperatures and pressures sufficient to cause the upper and lower sheet materials to bond (or fuse) to each other. However, temperatures which cause decomposition, distortion, or other undesirable effects in the finished article or sheet material, should be avoided. Avoidance of such extreme temperatures is an advantage of the miscible polyester/polycarbonate sheet materials of the present invention compared to the use of neat polycarbonate sheet. Normally, the bonding temperatures are in the range of about 90 to 300° C. (194 to 572° F.), preferably in the range of about 129 to 260° C. (265 to 500° F.). The pressures utilized in the bonding or laminating of the sandwich preferably are in the range of about 0.65 to 3.45 MPa (about 95 to 500 pounds per square inch-psi). The optimal temperature for bonding the thermoplastic articles will vary depending, for example, on the particular miscible copolyester/polycarbonate blend employed and the thickness of the sheet materials used, and may be determined by those skilled in the art. The sandwich or laminate is held at the appropriate temperature and pressure for about 4 to 24 minutes, or until such time as a bond is formed between the upper and lower sheet materials. After 4 to 24 minutes, the bonded/fused thermoplastic article is allowed to cool under pressures from about 0.69 to 2.4 MPa (about 100 to 350 psi), preferably about 1.4 MPa (200 psi), until it cools below the glass transition temperature of the miscible polyester/polycarbonate blend sheet material(s). During the bonding process, the miscible polyester/polycarbonate blend sheet materials may be bonded or fused to each other without the use of an adhesive. The lamination process may utilize adhesives or coupling agents on the fabric to enhance the adhesion of the thermoplastic sheet materials to the decorative material.

The miscible polyester/polycarbonate blends constituting the sheet materials used in the manufacture of the articles and sheeting of the present invention may not be as hard or scratch resistant as may be necessary or desired for certain end uses. For example, an end use in which the exterior surface of the thermoplastic article may be subjected to scratching or abrasion, i.e., in a privacy partition, may require the application of an abrasion-resistant coating to one or both of the exterior surfaces. For example, films consisting of fluorinated hydrocarbons, poly(perfluoroethylene) such as TEDLAR from duPont Chemical Company or oriented poly(ethylene terephthalate) such as MYLAR from duPont Chemical Company may be used to improve both chemical and abrasion resistance. The abrasion resistant film typically has a thickness in the range of about 0.025 to 0.254 mm (0.001-0.01 inch), preferably about 0.051 to 0.178 mm (0.002-0.007 inch), and most preferably about 0.076 mm (0.003 inch). However, abrasion resistant film thinner or thicker than these ranges may be used since the thickness of such film is limited only by the equipment available cost and functionality considerations. An adhesive optionally may be used between the miscible copolyester/polycarbonate blend and the abrasion resistant film.

Alternatively, an abrasion resistant coating may be applied to a plastic film and then the film bearing the abrasion resistant coating may be laminated to one or both sides of the article or sheeting of the present invention. The film may be selected from a number of thermoplastic materials compatible with the lamination process such as poly(vinyl chloride), PETG copolyester, poly(ethylene terephthalate), poly(methyl methacrylate), polycarbonate, miscible polyester/polycarbonate blends, and the like. PETG is defined herein as a polyester comprising, terephthalic acid, ethylene glycol and 1,4-cyclohexanedimethanol. Preferably, PETG comprises from 80 to 100 mole % terephthalic acid, 20 to 60 mole % 1,4-cyclohexanedimethanol and 80 to 40 mole % ethylene glycol based on the mole percentages for diacids totaling 100 mole % and the mole percentages for diols totaling 100 mole %.

The film thickness may range from 0.0025-0.381 mm (0.001-0.015 inch) with a thickness of 0.0762-0.203 mm (0.003-0.008) being most preferred. The coating may be selected from a number of commercially-available materials such as polyurethanes, fluorinated polyurethanes and silicones which are cured by heat or they may be selected from materials that are cured by ultraviolet (UV) or electron beam (EB) radiation. Such UV/EB cured materials fall under the general class of acrylates and modified acrylates that contain fluorine, silicone, epoxy, polyester, polyether or caprolactone residues or functional groups. The particular coating material selected will depend primarily on the degree of abrasion resistance required. Application of the liquid, heat- or UV/EB-curable precursor of the abrasion resistant coating may be carried out according to conventional procedures and usually is accomplished on a roll coating machine. The thickness of the coating applied to a film generally is 0.0076-0.051 mm (0.0003-0.002 inch) with thickness of about 0.0127 mm (0.0005 inch) being most preferred.

These coatings may be applied in a manner similar to the application of paints. The coatings exist either as predominantly undiluted material with very little volatile content or as solvent- or water-based materials. In addition to being applied to a film that can be laminated to the structure as part of the process, they may be applied directly to the finished product. Application may be carried out by a variety of techniques such as roll, paint, spray, mist, dip and the like.

The thermoplastic article or laminate, based on the miscible polyester/polycarbonate blend, can be subsequently shaped and thermoformed into a variety of useful products. As an illustrative example, the thermoplastic article can be thermoformed or otherwise shaped into sliding glass doors, shower doors, entrance doors, privacy partitions, multi-paned windows, and tabletops and other furniture pieces. Depending on the nature of the decorative material, the thermoplastic articles of this invention may be formed, heat draped, or molded. In addition, the articles of the present invention have an appealing appearance with low density to facilitate transport and installation of building materials produced there from.

The invention further relates to methods of forming the polyesters into thermoformed film(s) and/or sheet(s) described herein. The methods of forming the polyesters into such thermoformed film(s) and/or sheet(s) are well generally known in the art. Examples of thermoformed sheet(s) include but are not limited to baby thermoformed sheet(s); water thermoformed sheet(s); commercial water thermoformed sheet(s); beverage thermoformed sheet(s) which include but are not limited to two liter thermoformed sheet(s), 20 ounce thermoformed sheet(s), 16.9 ounce thermoformed sheet(s); medical thermoformed sheet(s); and thermoformed sheet(s) comprising at least one handle. These thermoformed sheet(s) include but not limited to injection blow molded thermoformed sheet(s), injection stretch blow molded thermoformed sheet(s), extrusion blow molded thermoformed sheet(s), and extrusion stretch blow molded thermoformed sheet(s). Methods of making thermoformed sheet(s) include but are not limited to extrusion blow molding, extrusion stretch blow molding, injection blow molding, and injection stretch blow molding.

This invention can be further illustrated by the following examples of preferred embodiments thereof, although it will be understood that these examples are included merely for purposes of illustration and are not intended to limit the scope of the invention unless otherwise specifically indicated. The starting materials are commercially available unless otherwise indicated. Unless indicated otherwise, parts are parts by weight, temperature is in degrees C. or is at room temperature, and pressure is at or near atmospheric.

EXAMPLES

The inherent viscosity of the polyesters was determined in 60/40 (wt/wt) phenol/tetrachloroethane at a concentration of 0.5 g/100 ml at 25° C.

Unless stated otherwise, the glass transition temperature ($T_g$) was determined using a TA DSC 2920 instrument from Thermal Analyst Instruments at a scan rate of 20° C./min according to ASTM D3418.

The glycol content and the cis/trans ratio of the compositions were determined by proton nuclear magnetic resonance (NMR) spectroscopy. All NMR spectra were recorded on a JEOL Eclipse Plus 600 MHz nuclear magnetic resonance spectrometer using either chloroform-trifluoroacetic acid (70-30 volume/volume) for polymers or, for oligomeric samples, 60/40(wt/wt) phenol/tetrachloroethane with deuterated chloroform added for lock. Peak assignments for 2,2,4,4-tetramethyl-1,3-cyclobutanediol resonances were made by comparison to model mono- and dibenzoate esters of 2,2,4,4-tetramethyl-1,3-cyclobutanediol. These model compounds closely approximate the resonance positions found in the polymers and oligomers.

The crystallization half-time, t½, was determined by measuring the light transmission of a sample via a laser and photo detector as a function of time on a temperature controlled hot stage. This measurement was done by exposing the polymers to a temperature, $T_{max}$, and then cooling it to the desired temperature. The sample was then held at the desired temperature by a hot stage while transmission measurements were made as a function of time. Initially, the sample was visually clear with high light transmission and became opaque as the sample crystallized. The crystallization half-time was recorded as the time at which the light transmission was halfway between the initial transmission and the final transmission. $T_{max}$ is defined as the temperature required to melt the crystalline domains of the sample (if crystalline domains are present). The $T_{max}$ reported in the examples below represents the temperature at which each sample was heated to condition the sample prior to crystallization half time measurement. The $T_{max}$ temperature is dependant on composition and is typically different for each polyester. For example, PCT may need to be heated to some temperature greater than 290° C. to melt the crystalline domains.

Density was determined using a gradient density column at 23° C.

The melt viscosity reported herein was measured by using a Rheometrics Dynamic Analyzer (RDA II). The melt viscosity was measured as a function of shear rate, at frequencies ranging from 1 to 400 rad/sec, at the temperatures reported. The zero shear melt viscosity ($\eta_o$) is the melt viscosity at zero shear rate estimated by extrapolating the data by known models in the art. This step is automatically performed by the Rheometrics Dynamic Analyzer (RDA II) software.

The polymers were dried at a temperature ranging from 80 to 100° C. in a vacuum oven for 24 hours and injection molded on a Boy 22S molding machine to give ⅛×½×5-inch and ¼×½×5-inch flexure bars. These bars were cut to a length of 2.5 inch and notched down the ½ inch width with a 10-mil notch in accordance with ASTM D256. The average Izod impact strength at 23° C. was determined from measurements on 5 specimens.

In addition, 5 specimens were tested at various temperatures using 5° C. increments in order to determine the brittle-to-ductile transition temperature. The brittle-to-ductile transition temperature is defined as the temperature at which 50% of the specimens fail in a brittle manner as denoted by ASTM D256.

Color values reported herein were determined using a Hunter Lab Ultrascan Spectra Colorimeter manufactured by Hunter Associates Lab Inc., Reston, Va. The color determinations were averages of values measured on either pellets of the polyesters or plaques or other items injection molded or extruded from them. They were determined by the L*a*b* color system of the CIE (International Commission on Illumination) (translated), wherein L* represents the lightness coordinate, a* represents the red/green coordinate, and b* represents the yellow/blue coordinate.

In addition, 10-mil films were compression molded using a Carver press at 240° C.

Unless otherwise specified, the cis/trans ratio of the 1,4 cyclohexanedimethanol used in the following examples was approximately 30/70, and could range from 35/65 to 25/75. Unless otherwise specified, the cis/trans ratio of the 2,2,4,4-tetramethyl-1,3-cyclobutanediol used in the following examples was approximately 50/50.

The following abbreviations apply throughout the working examples and figures:

| | |
|---|---|
| TPA | Terephthalic acid |
| DMT | Dimethyl therephthalate |
| TMCD | 2,2,4,4-tetramethyl-1,3-cyclobutanediol |
| CHDM | 1,4-cyclohexanedimethanol |
| IV | Inherent viscosity |
| $\eta_o$ | Zero shear melt viscosity |
| $T_g$ | Glass transition temperature |
| $T_{bd}$ | Brittle-to-ductile transition temperature |
| $T_{max}$ | Conditioning temperature for crystallization half time measurements |

Example 1

This example illustrates that 2,2,4,4-tetramethyl-1,3-cyclobutanediol is more effective at reducing the crystallization rate of PCT than ethylene glycol or isophthalic acid. In addition, this example illustrates the benefits of 2,2,4,4-tetramethyl-1,3-cyclobutanediol on the glass transition temperature and density.

A variety of copolyesters were prepared as described below. These copolyesters were all made with 200 ppm dibutyl tin oxide as the catalyst in order to minimize the effect of catalyst type and concentration on nucleation during crystallization studies. The cis/trans ratio of the 1,4-cyclohexanedimethanol was 31/69 while the cis/trans ratio of the 2,2,4,4-tetramethyl-1,3-cyclobutanediol is reported in Table 1.

For purposes of this example, the samples had sufficiently similar inherent viscosities thereby effectively eliminating this as a variable in the crystallization rate measurements.

Crystallization half-time measurements from the melt were made at temperatures from 140 to 200° C. at 10° C. increments and are reported in Table 1. The fastest crystallization half-time for each sample was taken as the minimum value of crystallization half-time as a function of temperature, typically occurring around 170 to 180° C. The fastest crystallization half-times for the samples are plotted in FIG. 1 as a function of mole % comonomer modification to PCT.

The data shows that 2,2,4,4-tetramethyl-1,3-cyclobutanediol is more effective than ethylene glycol and isophthalic acid at decreasing the crystallization rate (i.e., increasing the crystallization half-time). In addition, 2,2,4,4-tetramethyl-1,3-cyclobutanediol increases $T_g$ and lowers density.

TABLE 1

| | | | | | | Crystallization Half-times (min) | | | | | | |
|---|---|---|---|---|---|---|---|---|---|---|---|---|
| Example | Comonomer (mol %)[1] | IV (dl/g) | Density (g/ml) | $T_g$ (° C.) | $T_{max}$ (° C.) | at 140° C. (min) | at 150° C. (min) | at 160° C. (min) | at 170° C. (min) | at 180° C. (min) | at 190° C. (min) | at 200° C. (min) |
| 1A | 20.2% A[2] | 0.630 | 1.198 | 87.5 | 290 | 2.7 | 2.1 | 1.3 | 1.2 | 0.9 | 1.1 | 1.5 |
| 1B | 19.8% B | 0.713 | 1.219 | 87.7 | 290 | 2.3 | 2.5 | 1.7 | 1.4 | 1.3 | 1.4 | 1.7 |
| 1C | 20.0% C | 0.731 | 1.188 | 100.5 | 290 | >180 | >60 | 35.0 | 23.3 | 21.7 | 23.3 | 25.2 |
| 1D | 40.2% A[2] | 0.674 | 1.198 | 81.2 | 260 | 18.7 | 20.0 | 21.3 | 25.0 | 34.0 | 59.9 | 96.1 |
| 1E | 34.5% B | 0.644 | 1.234 | 82.1 | 260 | 8.5 | 8.2 | 7.3 | 7.3 | 8.3 | 10.0 | 11.4 |
| 1F | 40.1% C | 0.653 | 1.172 | 122.0 | 260 | >10 days | >5 days | >5 days | 19204 | >5 days | >5 days | >5 days |

TABLE 1-continued

| | | | | | | Crystallization Half-times (min) | | | | | | |
|---|---|---|---|---|---|---|---|---|---|---|---|---|
| Example | Comonomer (mol %)[1] | IV (dl/g) | Density (g/ml) | $T_g$ (° C.) | $T_{max}$ (° C.) | at 140° C. (min) | at 150° C. (min) | at 160° C. (min) | at 170° C. (min) | at 180° C. (min) | at 190° C. (min) | at 200° C. (min) |
| 1G | 14.3% D | 0.646[3] | 1.188 | 103.0 | 290 | 55.0 | 28.8 | 11.6 | 6.8 | 4.8 | 5.0 | 5.5 |
| 1H | 15.0% E | 0.728[4] | 1.189 | 99.0 | 290 | 25.4 | 17.1 | 8.1 | 5.9 | 4.3 | 2.7 | 5.1 |

[1]The balance of the diol component of the polyesters in Table 1 is 1,4-cyclohexanedimethanol; and the balance of the dicarboxylic acid component of the polyesters in Table 1 is dimethyl terephthalate; if the dicarboxylic acid is not described, it is 100 mole % dimethyl terephthalate.
[2]100 mole % 1,4-cyclohexanedimethanol.
[3]A film was pressed from the ground polyester of Example 1G at 240° C. The resulting film had an inherent viscosity value of 0.575 dL/g.
[4]A film was pressed from the ground polyester of Example 1H at 240° C. The resulting film had an inherent viscosity value of 0.0.652 dL/g.
where:
A is Isophthalic Acid
B is Ethylene Glycol
C is 2,2,4,4-Tetramethyl-1,3-cyclobutanediol (approx. 50/50 cis/trans)
D is 2,2,4,4-Tetramethyl-1,3-cyclobutanediol (98/2 cis/trans)
E is 2,2,4,4-Tetramethyl-1,3-cyclobutanediol (5/95 cis/trans)

As shown in Table 1 and FIG. 1, 2,2,4,4-tetramethyl-1,3-cyclobutanediol is more effective than other comonomers, such ethylene glycol and isophthalic acid, at increasing the crystallization half-time, i.e., the time required for a polymer to reach half of its maximum crystallinity. By decreasing the crystallization rate of PCT (increasing the crystallization half-time), amorphous articles based on 2,2,4,4-tetramethyl-1,3-cyclobutanediol-modified PCT as described herein may be fabricated by methods known in the art. As shown in Table 1, these materials can exhibit higher glass transition temperatures and lower densities than other modified PCT copolyesters.

Preparation of the polyesters shown on Table 1 is described below.

Example 1A

This example illustrates the preparation of a copolyester with a target composition of 80 mol% dimethyl terephthalate residues, 20 mol % dimethyl isophthalate residues, and 100 mol% 1,4-cyclohexanedimethanol residues (28/72 cis/trans).

A mixture of 56.63 g of dimethyl terephthalate, 55.2 g of 1,4-cyclohexanedimethanol, 14.16 g of dimethyl isophthalate, and 0.0419 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 5 minutes and then the temperature was gradually increased to 290° C. over 30 minutes. The reaction mixture was held at 290° C. for 60 minutes and then vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 87.5° C. and an inherent viscosity of 0.63 dl/g. NMR analysis showed that the polymer was composed of 100 mol % 1,4-cyclohexanedimethanol residues and 20.2 mol % dimethyl isophthalate residues.

Example 1B

This example illustrates the preparation of a copolyester with a target composition of 100 mol % dimethyl terephthalate residues, 20 mol % ethylene glycol residues, and 80 mol % 1,4-cyclohexanedimethanol residues (32/68 cis/trans).

A mixture of 77.68 g of dimethyl terephthalate, 50.77 g of 1,4-cyclohexanedimethanol, 27.81 g of ethylene glycol, and 0.0433 g of dibutyl tin oxide was placed in a 500-milliliter flask equipped with an inlet for nitrogen, a metal stirrer, and a short distillation column. The flask was placed in a Wood's metal bath already heated to 200° C. The stirring speed was set to 200 RPM throughout the experiment. The contents of the flask were heated at 200° C. for 60 minutes and then the temperature was gradually increased to 210° C. over 5 minutes. The reaction mixture was held at 210° C. for 120 minutes and then heated up to 280° C. in 30 minutes. Once at 280° C., vacuum was gradually applied over the next 5 minutes until the pressure inside the flask reached 100 mm of Hg. The pressure inside the flask was further reduced to 0.3 mm of Hg over the next 10 minutes. A pressure of 0.3 mm of Hg was maintained for a total time of 90 minutes to remove excess unreacted diols. A high melt viscosity, visually clear and colorless polymer was obtained with a glass transition temperature of 87.7° C. and an inherent viscosity of 0.71 dl/g. NMR analysis showed that the polymer was composed of 19.8 mol % ethylene glycol residues.

Example 1C

This example illustrates the preparation of a copolyester with a target composition of 100 mol % dimethyl terephthalate residues, 20 mol % 2,2,4,4-tetramethyl-1,3-cyclobutanediol residues, and 80 mol % 1,4-cyclohexanedimethanol residues (31/69 cis/trans).

A mixture of 77.68 g of dimethyl terephthalate, 48.46 g of 1,4-cyclohexanedimethanol, 17.86 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. This polyester was prepared in a manner similar to that described in Example 1A. A high melt viscosity, visually clear and colorless polymer was obtained with a glass transition temperature of 100.5° C. and an inherent viscosity of 0.73 dl/g. NMR analysis showed that the polymer was composed of 80.5 mol % 1,4-cyclohexanedimethanol residues and 19.5 mol % 2,2,4,4-tetramethyl-1,3-cyclobutanediol residues.

Example 1D

This example illustrates the preparation of a copolyester with a target composition of 100 mol % dimethyl terephthalate residues, 40 mol % dimethyl isophthalate residues, and 100 mol % 1,4-cyclohexanedimethanol residues (28/72 cis/trans).

A mixture of 42.83 g of dimethyl terephthalate, 55.26 g of 1,4-cyclohexanedimethanol, 28.45 g of dimethyl isophthalate, and 0.0419 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 5 minutes and then the temperature was gradually increased to 290° C. over 30 minutes. The reaction mixture was held at 290° C. for 60 minutes and then vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 81.2° C. and an inherent viscosity of 0.67 dl/g. NMR analysis showed that the polymer was composed of 100 mol % 1,4-cyclohexanedimethanol residues and 40.2 mol % dimethyl isophthalate residues.

Example 1E

This example illustrates the preparation of a copolyester with a target composition of 100 mol % dimethyl terephthalate residues, 40 mol % ethylene glycol residues, and 60 mol % 1,4-cyclohexanedimethanol residues (31/69 cis/trans).

A mixture of 81.3 g of dimethyl terephthalate, 42.85 g of 1,4-cyclohexanedimethanol, 34.44 g of ethylene glycol, and 0.0419 g of dibutyl tin oxide was placed in a 500-milliliter flask equipped with an inlet for nitrogen, a metal stirrer, and a short distillation column. The flask was placed in a Wood's metal bath already heated to 200° C. The stirring speed was set to 200 RPM throughout the experiment. The contents of the flask were heated at 200° C. for 60 minutes and then the temperature was gradually increased to 210° C. over 5 minutes. The reaction mixture was held at 210° C. for 120 minutes and then heated up to 280° C. in 30 minutes. Once at 280° C., vacuum was gradually applied over the next 5 minutes until the pressure inside the flask reached 100 mm of Hg. The pressure inside the flask was further reduced to 0.3 mm of Hg over the next 10 minutes. A pressure of 0.3 mm of Hg was maintained for a total time of 90 minutes to remove excess unreacted diols. A high melt viscosity, visually clear and colorless polymer was obtained with a glass transition temperature of 82.1° C. and an inherent viscosity of 0.64 dl/g. NMR analysis showed that the polymer was composed of 34.5 mol % ethylene glycol residues.

Example 1F

This example illustrates the preparation of a copolyester with a target composition of 100 mol % dimethyl terephthalate residues, 40 mol % 2,2,4,4-tetramethyl-1,3-cyclobutanediol residues, and 60 mol % 1,4-cyclohexanedimethanol residues (31/69 cis/trans).

A mixture of 77.4 g of dimethyl terephthalate, 36.9 g of 1,4-cyclohexanedimethanol, 32.5 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 122° C. and an inherent viscosity of 0.65 dl/g. NMR analysis showed that the polymer was composed of 59.9 mol % 1,4-cyclohexanedimethanol residues and 40.1 mol % 2,2,4,4-tetramethyl-1,3-cyclobutaned iol residues.

Example 1G

This example illustrates the preparation of a copolyester with a target composition of 100 mol % dimethyl terephthalate residues, 20 mol % 2,2,4,4-tetramethyl-1,3-cyclobutanediol residues (98/2 cis/trans), and 80 mol % 1,4-cyclohexanedimethanol residues (31/69 cis/trans).

A mixture of 77.68 g of dimethyl terephthalate, 48.46 g of 1,4-cyclohexanedimethanol, 20.77 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes until the pressure inside the flask reached 100 mm of Hg and the stirring speed was also reduced to 100 RPM. The pressure inside the flask was further reduced to 0.3 mm of Hg over the next 5 minutes and the stirring speed was reduced to 50 RPM. A pressure of 0.3 mm of Hg was maintained for a total time of 60 minutes to remove excess unreacted diols. A high melt viscosity, visually clear and colorless polymer was obtained with a glass transition temperature of 103° C. and an inherent viscosity of 0.65 dl/g. NMR analysis showed that the polymer was composed of 85.7 mol % 1,4-cyclohexanedimethanol residues and 14.3 mol % 2,2,4,4-tetramethyl-1,3-cyclobutanediol residues.

Example 1H

This example illustrates the preparation of a copolyester with a target composition of 100 mol % dimethyl terephthalate residues, 20 mol % 2,2,4,4-tetramethyl-1,3-cyclobutanediol residues (5/95 cis/trans), and 80 mol % 1,4-cyclohexanedimethanol residues (31/69 cis/trans).

A mixture of 77.68 g of dimethyl terephthalate, 48.46 g of 1,4-cyclohexanedimethanol, 20.77 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM at the beginning of the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes with a set point of 100 mm of Hg and the stirring speed was also reduced to 100 RPM. The pressure inside the flask was further reduced to a set point of 0.3 mm of Hg over the next 5 minutes and the stirring speed was reduced to 50 RPM. This pressure was maintained for a total time of 60 minutes to remove excess unreacted diols. It was noted that the vacuum system failed to reach the set point mentioned above, but produced enough vacuum to produce a high melt viscosity, visually clear and colorless polymer with a glass transition temperature of 99° C. and an inherent viscosity of 0.73 dl/g. NMR analysis showed that the polymer was composed of 85 mol % 1,4-cyclohexanedimethanol residues and 15 mol % 2,2,4,4-tetramethyl-1,3-cyclobutanediol residues.

Example 2

This example illustrates that 2,2,4,4-tetramethyl-1,3-cyclobutanediol improves the toughness of PCT-based copolyesters (polyesters containing terephthalic acid and 1,4-cyclohexanedimethanol).

Copolyesters based on 2,2,4,4-tetramethyl-1,3-cyclobutanediol were prepared as described below. The cis/trans ratio of the 1,4-cyclohexanedimethanol was approximately 31/69 for all samples. Copolyesters based on ethylene glycol and 1,4-cyclohexanedimethanol were commercial polyesters. The copolyester of Example 2A (Eastar PCTG 5445) was obtained from Eastman Chemical Co. The copolyester of Example 2B was obtained from Eastman Chemical Co. under the trade name Spectar. Example 2C and Example 2D were prepared on a pilot plant scale (each a 15-lb batch) following an adaptation of the procedure described in Example 1A and having the inherent viscosities and glass transition temperatures described in Table 2 below. Example 2C was prepared with a target tin amount of 300 ppm (Dibutyltin Oxide). The final product contained 295 ppm tin. The color values for the polyester of Example 2C were L*=77.11; a*=−1.50; and b*=5.79. Example 2D was prepared with a target tin amount of 300ppm (Dibutyltin Oxide). The final product contained 307 ppm tin. The color values for the polyester of Example 2D were L*=66.72; a*=−1.22; and b*=16.28.

Materials were injection molded into bars and subsequently notched for Izod testing. The notched Izod impact strengths were obtained as a function of temperature and are also reported in Table 2.

For a given sample, the Izod impact strength undergoes a major transition in a short temperature span. For instance, the Izod impact strength of a copolyester based on 38 mol % ethylene glycol undergoes this transition between 15 and 20° C. This transition temperature is associated with a change in failure mode; brittle/low energy failures at lower temperatures and ductile/high energy failures at higher temperatures. The transition temperature is denoted as the brittle-to-ductile transition temperature, $T_{bd}$, and is a measure of toughness. $T_{bd}$ is reported in Table 2 and plotted against mol % comonomer in FIG. 2.

The data shows that adding 2,2,4,4-tetramethyl-1,3-cyclobutanediol to PCT lowers $T_{bd}$ and improves the toughness, as compared to ethylene glycol, which increases $T_{bd}$ of PCT.

TABLE 2

| | | | | | Notched Izod Impact Energy (ft-lb/in) | | | | | | | | | | |
|---|---|---|---|---|---|---|---|---|---|---|---|---|---|---|---|
| Example | Comonomer (mol %)[1] | IV (dl/g) | $T_g$ (° C.) | $T_{bd}$ (° C.) | at −20° C. | at −15° C. | at −10° C. | at −5° C. | at 0° C. | at 5° C. | at 10° C. | at 15° C. | at 20° C. | at 25° C. | at 30° C. |
| 2A | 38.0% B | 0.68 | 86 | 18 | NA | NA | NA | 1.5 | NA | NA | 1.5 | 1.5 | 32 | 32 | NA |
| 2B | 69.0% B | 0.69 | 82 | 26 | NA | NA | NA | NA | NA | NA | 2.1 | NA | 2.4 | 13.7 | 28.7 |
| 2C | 22.0% C | 0.66 | 106 | −5 | 1.5 | NA | 12 | 23 | 23 | NA | 23 | NA | NA | NA | NA |
| 2D | 42.8% C | 0.60 | 133 | −12 | 2.5 | 2.5 | 11 | NA | 14 | NA | NA | NA | NA | NA | NA |

[1]The balance of the glycol component of the polyesters in the Table is 1,4-cyclohexanedimethanol. All polymers were prepared from 100 mole % dimethyl terephthalate.
NA = Not available.
where:
B is Ethylene glycol
C is 2,2,4,4-Tetramethyl-1,3-cyclobutanediol (50/50 cis/trans)

Example 3

This example illustrates that 2,2,4,4-tetramethyl-1,3-cyclobutanediol can improve the toughness of PCT-based copolyesters(polyesters containing terephthalic acid and 1,4-cyclohexanedimethanol). Polyesters prepared in this example comprise from 15 to 25 mol % of 2,2,4,4-tetramethyl-1,3-cyclobutanediol residues.

Copolyesters based on dimethyl terephthalate, 2,2,4,4-tetramethyl-1,3-cyclobutanediol, and 1,4-cyclohexanedimethanol were prepared as described below, having the composition and properties shown on Table 3. The balance up to 100 mol % of the diol component of the polyesters in Table 3 was 1,4-cyclohexanedimethanol (31/69 cis/trans).

Materials were injection molded into both 3.2mm and 6.4mm thick bars and subsequently notched for Izod impact testing. The notched Izod impact strengths were obtained at 23° C. and are reported in Table 3. Density, Tg, and crystallization halftime were measured on the molded bars. Melt viscosity was measured on pellets at 290° C.

TABLE 3

Compilation of various properties for certain polyesters useful in the invention

| Example | TMCD mole % | % cis TMCD | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt at 170° C. (min) | Melt Viscosity at 1 rad/sec at 290° C. (Poise) |
|---|---|---|---|---|---|---|---|---|---|---|
| A | 15 | 48.8 | 0.736 | 0.707 | 1069 | 878 | 1.184 | 104 | 15 | 5649 |
| B | 18 | NA | 0.728 | 0.715 | 980 | 1039 | 1.183 | 108 | 22 | 6621 |
| C | 20 | NA | 0.706 | 0.696 | 1006 | 1130 | 1.182 | 106 | 52 | 6321 |
| D | 22 | NA | 0.732 | 0.703 | 959 | 988 | 1.178 | 108 | 63 | 7161 |
| E | 21 | NA | 0.715 | 0.692 | 932 | 482 | 1.179 | 110 | 56 | 6162 |
| F | 24 | NA | 0.708 | 0.677 | 976 | 812 | 1.180 | 109 | 58 | 6282 |
| G | 23 | NA | 0.650 | 0.610 | 647 | 270 | 1.182 | 107 | 46 | 3172 |
| H | 23 | 47.9 | 0.590 | 0.549 | 769 | 274 | 1.181 | 106 | 47 | 1736 |
| I | 23 | 48.1 | 0.531 | 0.516 | 696 | 352 | 1.182 | 105 | 19 | 1292 |
| J | 23 | 47.8 | 0.364 | NA | NA | NA | NA | 98 | NA | 167 |

NA = Not available.

Example 3A 21.24 lb (49.71 gram-mol) dimethyl terephthalate, 14.34 lb (45.21 gram-mol) 1,4-cyclohexanedimethanol, and 4.58 lb (14.44 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and at a pressure of 20 psig. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg until the power draw to the agitator no longer increased (70 minutes). The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.736 dL/g and a Tg of 104° C. NMR analysis showed that the polymer was composed of 85.4 mol % 1,4-cyclohexane-dimethanol residues and 14.6 mol % 2,2,4,4-tetramethyl-1,3-cyclobutanediol residues. The polymer had color values of: L*=78.20, a*=−1.62, and b*=6.23.

Example 3B to Example 3D

The polyesters described in Example 3B to Example 3D were prepared following a procedure similar to the one described for Example 3A. The composition and properties of these polyesters are shown in Table 3.

Example 3E 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg for 60 minutes. The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.715 dL/g and a Tg of 110° C. X-ray analysis showed that the polyester had 223 ppm tin. NMR analysis showed that the polymer was composed of 78.6 mol % 1,4-cyclohexane-dimethanol residues and 21.4 mol % 2,2,4,4-tetramethyl-1,3-cyclobutanediol residues. The polymer had color values of: L*=76.45, a*=−1.65, and b*=6.47.

Example 3F

The polyester described in Example 3F was prepared following a procedure similar to the one described for Example 3A. The composition and properties of this polyester are shown in Table 3.

Example 3H 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg for 12 minutes. The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.590 dL/g and a Tg of 106° C. NMR analysis showed that the polymer was composed of 77.1 mol % 1,4-cyclohexane-dimethanol residues and 22.9 mol % 2,2,4,4-tetramethyl-1,3-cyclobutanediol residues. The polymer had color values of: L*=83.27, a*=−1.34, and b*=5.08.

Example 3I 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to 4 mm of Hg. The reaction mixture was held at 290° C. and at a pressure of 4 mm of Hg for 30 minutes. The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.531 dL/g and a Tg of 105° C. NMR analysis showed that the polymer was composed of 76.9 mol % 1,4-cyclohexane-dimethanol residues and 23.1 mol % 2,2,4,4-tetramethyl-1,3-cyclobutanediol residues. The polymer had color values of: L*=80.42, a*=−1.28, and b*=5.13.

Example 3J 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to 4 mm of Hg. When the reaction mixture temperature was 290° C. and the pressure was 4 mm of Hg, the pressure of the pressure vessel was immediately increased to 1 atmosphere using nitrogen gas. The molten polymer was then extruded from the pressure vessel. The cooled, extruded polymer was ground to pass a 6-mm screen. The polymer had an inherent viscosity of 0.364 dL/g and a Tg of 98° C. NMR analysis showed that the polymer was composed of 77.5 mol % 1,4-cyclohexane-dimethanol residues and 22.5 mol % 2,2,4,4-tetramethyl-1,3-cyclobutanediol residues. The polymer had color values of: L*=77.20, a*=−1.47, and b*=4.62.

Example 4

This example illustrates that 2,2,4,4-tetramethyl-1,3-cyclobutanediol can improve the toughness of PCT-based copolyesters(polyesters containing terephthalic acid and 1,4-cyclohexanedimethanol). Polyesters prepared in this example fall comprise more than 25 to less than 40 mol % of 2,2,4,4-tetramethyl-1,3-cyclobutanediol residues.

Copolyesters based on dimethyl terephthalate, 2,2,4,4-tetramethyl-1,3-cyclobutanediol, and 1,4-cyclohexanedimethanol (31/69 cis/trans) were prepared as described below, having the composition and properties shown on Table 4. The balance up to 100 mol % of the diol component of the polyesters in Table 4 was 1,4-cyclohexanedimethanol (31/69 cis/trans).

Materials were injection molded into both 3.2mm and 6.4mm thick bars and subsequently notched for Izod impact testing. The notched Izod impact strengths were obtained at 23° C. and are reported in Table 4. Density, Tg, and crystallization halftime were measured on the molded bars. Melt viscosity was measured on pellets at 290° C.

TABLE 4

Compilation of various properties for certain polyesters useful in the invention

| Example | TMCD mole % | % cis TMCD | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt at 170° C. (min) | Melt Viscosity at 1 rad/sec at 290° C. (Poise) |
|---|---|---|---|---|---|---|---|---|---|---|
| A | 27 | 47.8 | 0.714 | 0.678 | 877 | 878 | 1.178 | 113 | 280 | 8312 |
| B | 31 | NA | 0.667 | 0.641 | 807 | 789 | 1.174 | 116 | 600 | 6592 |

NA = Not available.

Example 4A 21.24 lb (49.71 gram-mol) dimethyl terephthalate, 11.82 lb (37.28 gram-mol) 1,4-cyclohexanedimethanol, and 6.90 lb (21.77 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg until the power draw to the agitator no longer increased (50 minutes). The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.714 dL/g and a Tg of 113° C. NMR analysis showed that the polymer was composed of 73.3 mol % 1,4-cyclohexane-dimethanol residues and 26.7 mol % 2,2,4,4-tetramethyl-1,3-cyclobutanediol residues.

Example 4B

The polyester of Example 4B was prepared following a procedure similar to the one described for Example 4A. The composition and properties of this polyester are shown in Table 4.

Example 5

This example illustrates that 2,2,4,4-tetramethyl-1,3-cyclobutanediol can improve the toughness of PCT-based copolyesters(polyesters containing terephthalic acid and 1,4-cyclohexanedimethanol).

A copolyester based on dimethyl terephthalate, 2,2,4,4-tetramethyl-1,3-cyclobutanediol, and 1,4-cyclohexanedimethanol was prepared as described below, having the composition and properties shown on Table 5. The balance up to 100 mol % of the diol component of the polyesters in Table 5 was 1,4-cyclohexanedimethanol (31/69 cis/trans).

The polyester was injection molded into both 3.2 mm and 6.4 mm thick bars and subsequently notched for Izod impact testing. The notched Izod impact strengths were obtained at 23° C. and are reported in Table 5. Density, Tg, and crystallization halftime were measured on the molded bars. Melt viscosity was measured on pellets at 290° C.

TABLE 5

Compilation of various properties for certain polyesters useful in the invention

| Example | TMCD mole % | % cis TMCD | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt at 170° C. (min) | Melt Viscosity at 1 rad/sec at 290° C. (Poise) |
|---|---|---|---|---|---|---|---|---|---|---|
| A | 44 | 46.2 | 0.657 | 0.626 | 727 | 734 | 1.172 | 119 | NA | 9751 |

NA = Not available.

Example 5A 21.24 lb (49.71 gram-mol) dimethyl terephthalate, 8.84 lb (27.88 gram-mol) 1,4-cyclohexanedimethanol, and 10.08 lb (31.77 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. Then the agitator speed was decreased to 15 RPM, the temperature of the reaction mixture was then increased to 290° C. and the pressure was decreased to 2 mm of Hg. The reaction mixture was held at 290° C. and at a pressure of 2 mm of Hg until the power draw to the agitator no longer increased (80 minutes). The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.657 dL/g and a Tg of 119° C. NMR analysis showed that the polymer was composed of 56.3 mol % 1,4-cyclohexanedimethanol residues and 43.7 mol % 2,2,4,4-tetramethyl-1,3-cyclobutanediol residues. The polymer had color values of: L*=75.04, a*=−1.82, and b*=6.72.

Example 6—Comparative Example

This example shows data for comparative materials are shown in Table 6. The PC was Makrolon 2608 from Bayer, with a nominal composition of 100 mole % bisphenol A residues and 100 mole % diphenyl carbonate residues. Makrolon 2608 has a nominal melt flow rate of 20 grams/10 minutes measured at 300 C using a 1.2 kg weight. The PET was Eastar 9921 from Eastman Chemical Company, with a nominal composition of 100 mole % terephthalic acid, 3.5 mole % cyclohexanedimenthanol (CHDM) and 96.5 mole % ethylene glycol. The PETG was Eastar 6763 from Eastman Chemical Company, with a nominal composition of 100 mole % terephthalic acid, 31 mole % cyclohexanedimenthanol (CHDM) and 69 mole % ethylene glycol. The PCTG was Eastar DN001 from Eastman Chemical Company, with a nominal composition of 100 mole % terephthalic acid, 62 mole % cyclohexanedimenthanol (CHDM) and 38 mole % ethylene glycol. The PCTA was Eastar AN001 from Eastman Chemical Company, with a nominal composition of 65 mole % terephthalic acid, 35 mole % isophthalic acid and 100 mole % cyclohexanedimenthanol (CHDM). The Polysulfone was Udel 1700 from Solvay, with a nominal composition of 100 mole % bisphenol A residues and 100 mole % 4,4-dichlorosulfonyl sulfone residues. Udel 1700 has a nominal melt flow rate of 6.5 grams/10 minutes measured at 343 C using a 2.16 kg weight. The SAN was Lustran 31 from Lanxess, with a nominal composition of 76 weight % styrene and 24 weight % acrylonitrile. Lustran 31 has a nominal melt flow rate of 7.5 grams/10 minutes measured at 230 C using a 3.8 kg weight. The examples of the invention show improved toughness in 6.4 mm thickness bars compared to all of the other resins.

TABLE 6

Compilation of various properties for certain commercial polymers

| Example | Polymer name | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt (min) |
|---|---|---|---|---|---|---|---|---|
| A | PC | 12 MFR | NA | 929 | 108 | 1.20 | 146 | NA |
| B | PCTG | 0.73 | 0.696 | NB | 70 | 1.23 | 87 | 30 at 170° C. |
| C | PCTA | 0.72 | 0.702 | 98 | 59 | 1.20 | 87 | 15 at 150° C. |
| D | PETG | 0.75 | 0.692 | 83 | 59 | 1.27 | 80 | 2500 at 130° C. |
| E | PET | 0.76 | 0.726 | 45 | 48 | 1.33 | 78 | 1.5 at 170° C. |
| F | SAN | 7.5 MFR | NA | 21 | NA | 1.07 | ~110 | NA |
| G | PSU | 6.5 MFR | NA | 69 | NA | 1.24 | ~190 | NA |

NA = Not available

Example 7

This example illustrates the effect of the amount of 2,2,4,4-tetramethyl-1,3-cyclobutanediol used for the preparation of the polyesters of the invention on the glass transition temperature of the polyesters. Polyesters prepared in this example comprise from 15 to 25 mol % of 2,2,4,4-tetramethyl-1,3-cyclobutanediol residues.

Example 7A to Example 7G

Dimethyl terephthalate, 1,4-cyclohexanedimethanol, and 2,2,4,4-tetramethyl-1,3-cyclobutanediol were weighed into a 500-ml single neck round bottom flask. NMR analysis on the 2,2,4,4-tetramethyl-1,3-cyclobutanediol starting material showed a cis/trans ratio of 53/47. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 20 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

Example 7H to Example 7Q

These polyesters were prepared by carrying out the ester exchange and polycondensation reactions in separate stages. The ester exchange experiments were conducted in a continuous temperature rise (CTR) reactor. The CTR was a 3000 ml glass reactor equipped with a single shaft impeller blade agitator, covered with an electric heating mantle and fitted with a heated packed reflux condenser column. The reactor was charged with 777 g (4 moles) of dimethyl terephthalate, 230 g (1.6 moles) of 2,2,4,4-tetramethyl-1,3,-cyclobutanediol, 460.8 g (3.2 moles) of cyclohexane dimethanol and 1.12 g of butyltin tris-2-ethylhexanoate (such that there will be 200 ppm tin metal in the final polymer). The heating mantle was set manually to 100% output. The set points and data collection were facilitated by a Camile process control system. Once the reactants were melted, stirring was initiated and slowly increased to 250 rpm. The temperature of the reactor gradually increased with run time. The weight of methanol collected was recorded via balance. The reaction was stopped when methanol evolution stopped or at a pre-selected lower temperature of 260° C. The oligomer was discharged with a nitrogen purge and cooled to room temperature. The oligomer was frozen with liquid nitrogen and broken into pieces small enough to be weighed into a 500 ml round bottom flask.

In the polycondensation reactions, a 500 ml round bottom flask was charged with approximately 150 g of the oligomer prepared above. The flask was equipped with a stainless steel stirrer and polymer head. The glassware was set up on a half mole polymer rig and the Camile sequence was initiated. The stirrer was positioned one full turn from the flask bottom once the oligomer melted. The temperature/pressure/stir rate sequence controlled by the Camile software for each example is reported in the following tables.

Camile Sequence for Example 7H and Example 7I

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 290 | 6 | 25 |

Camile Sequence for Example 7N to Example 7Q

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 3 | 25 |
| 7 | 110 | 290 | 3 | 25 |

Camile Sequence for Example 7K and Example 7L

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 2 | 25 |
| 7 | 110 | 290 | 2 | 25 |

Camile Sequence for Example 7J and Example 7M

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 1 | 25 |
| 7 | 110 | 290 | 1 | 25 |

The resulting polymers were recovered from the flask, chopped using a hydraulic chopper, and ground to a 6 mm screen size. Samples of each ground polymer were submitted for inherent viscosity in 60/40 (wt/wt) phenol/tetrachloroethane at a concentration of 0.5 g/100 ml at 25° C., catalyst level (Sn) by x-ray fluorescence, and color (L*, a*, b*) by transmission spectroscopy. Polymer composition was obtained by $^1$H NMR. Samples were submitted for thermal stability and melt viscosity testing using a Rheometrics Mechanical Spectrometer (RMS 800).

Figure 3:
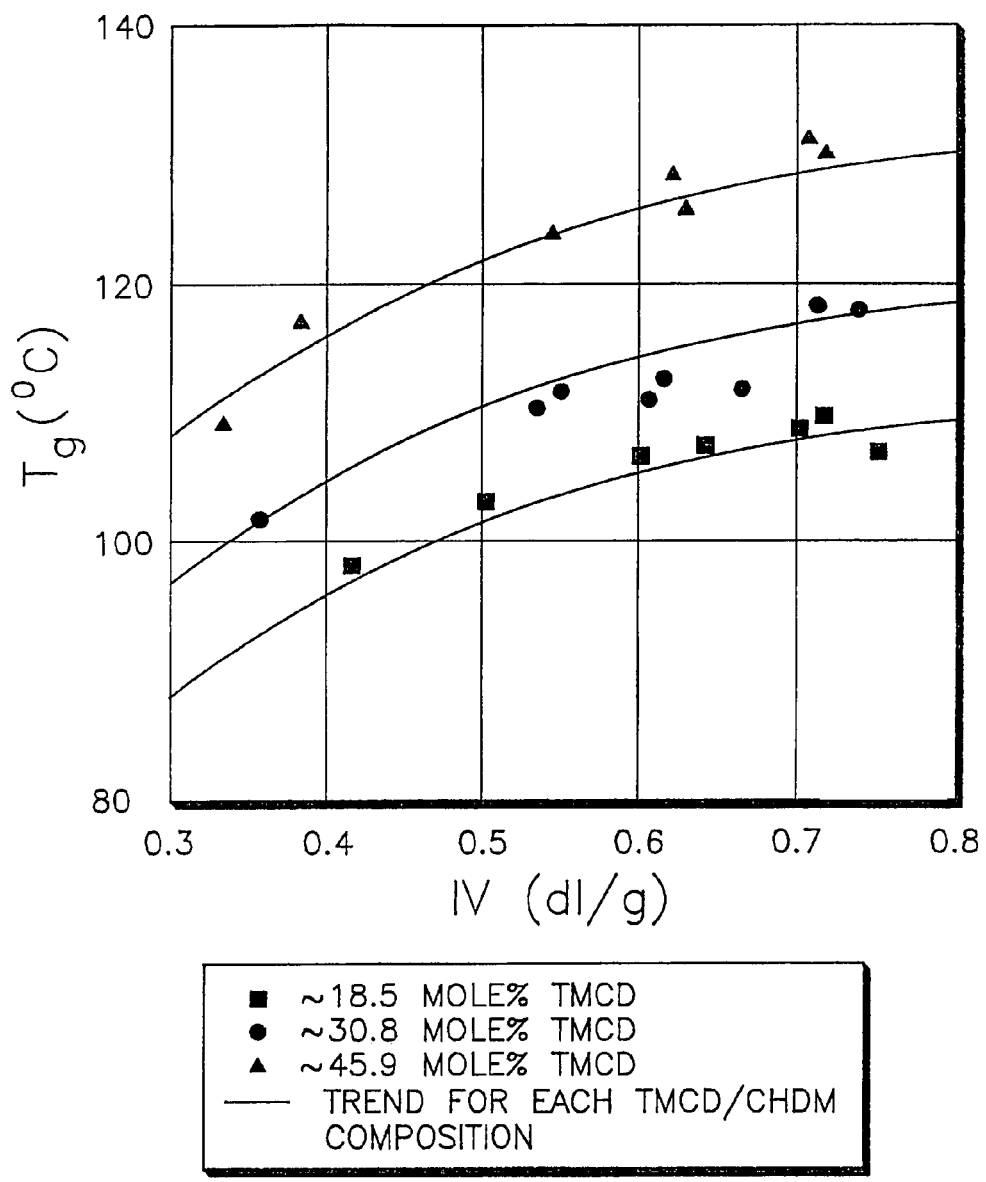
FIG. 3 is a graph showing the effect of 2,2,4,4-tetramethyl-1,3-cyclobutanediol composition on the glass transition temperature (Tg) of the copolyester.

The table below shows the experimental data for the polyesters of this example. The data shows that an increase in the level of 2,2,4,4-tetramethyl-1,3-cyclobutanediol raises the glass transition temperature in an almost linear fashion, for a constant inherent viscosity. FIG. 3 also shows the dependence of Tg on composition and inherent viscosity.

TABLE 7

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 20 | 51.4 | 0.72 | 109 | 11356 | 19503 | 5527 |
| B | 19.1 | 51.4 | 0.60 | 106 | 6891 | 3937 | 2051 |
| C | 19 | 53.2 | 0.64 | 107 | 8072 | 4745 | 2686 |
| D | 18.8 | 54.4 | 0.70 | 108 | 14937 | 8774 | 4610 |
| E | 17.8 | 52.4 | 0.50 | 103 | 3563 | 1225 | 883 |
| F | 17.5 | 51.9 | 0.75 | 107 | 21160 | 10877 | 5256 |
| G | 17.5 | 52 | 0.42 | 98 | NA | NA | NA |
| H | 22.8 | 53.5 | 0.69 | 109 | NA | NA | NA |
| I | 22.7 | 52.2 | 0.68 | 108 | NA | NA | NA |
| J | 23.4 | 52.4 | 0.73 | 111 | NA | NA | NA |
| K | 23.3 | 52.9 | 0.71 | 111 | NA | NA | NA |
| L | 23.3 | 52.4 | 0.74 | 112 | NA | NA | NA |
| M | 23.2 | 52.5 | 0.74 | 112 | NA | NA | NA |
| N | 23.1 | 52.5 | 0.71 | 111 | NA | NA | NA |
| O | 22.8 | 52.4 | 0.73 | 112 | NA | NA | NA |
| P | 22.7 | 53 | 0.69 | 112 | NA | NA | NA |
| Q | 22.7 | 52 | 0.70 | 111 | NA | NA | NA |

NA = Not available

Example 8

This example illustrates the effect of the amount of 2,2,4,4-tetramethyl-1,3-cyclobutanediol used for the preparation of the polyesters of the invention on the glass transition temperature of the polyesters. Polyesters prepared in this example fall comprise more than 25 to less than 40 mol % of 2,2,4,4-tetramethyl-1,3-cyclobutanediol residues.

Dimethyl terephthalate, 1,4-cyclohexanedimethanol, and 2,2,4,4-tetramethyl-1,3-cyclobutanediol were weighed into a 500-ml single neck round bottom flask. NMR analysis on the 2,2,4,4-tetramethyl-1,3-cyclobutanediol starting material showed a cis/trans ratio of 53/47. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 32 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

The table below shows the experimental data for the polyesters of this example. FIG. 3 also shows the dependence of Tg on composition and inherent viscosity. The data shows that an increase in the level of 2,2,4,4-tetramethyl-1,3-cyclobutanediol raises the glass transition temperature in an almost linear fashion, for a constant inherent viscosity.

TABLE 8

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 32.2 | 51.9 | 0.71 | 118 | 29685 | 16074 | 8522 |
| B | 31.6 | 51.5 | 0.55 | 112 | 5195 | 2899 | 2088 |
| C | 31.5 | 50.8 | 0.62 | 112 | 8192 | 4133 | 2258 |
| D | 30.7 | 50.7 | 0.54 | 111 | 4345 | 2434 | 1154 |
| E | 30.3 | 51.2 | 0.61 | 111 | 7929 | 4383 | 2261 |
| F | 30.0 | 51.4 | 0.74 | 117 | 31476 | 17864 | 8630 |
| G | 29.0 | 51.5 | 0.67 | 112 | 16322 | 8787 | 4355 |
| H | 31.1 | 51.4 | 0.35 | 102 | NA | NA | NA |

NA = Not available

Example 9

This example illustrates the effect of the amount of 2,2,4,4-tetramethyl-1,3-cyclobutanediol used for the preparation of the polyesters of the invention on the glass transition temperature of the polyesters. Polyesters prepared in this example comprise 2,2,4,4-tetramethyl-1,3-cyclobutanediol residues in an amount of 40 mol % or greater.

Examples A to C

These polyesters were prepared by carrying out the ester exchange and polycondensation reactions in separate stages. The ester exchange experiments were conducted in a continuous temperature rise (CTR) reactor. The CTR was a 3000 ml glass reactor equipped with a single shaft impeller blade agitator, covered with an electric heating mantle and fitted with a heated packed reflux condenser column. The reactor was charged with 777 g of dimethyl terephthalate, 375 g of 2,2,4,4-tetramethyl-1,3,-cyclobutanediol, 317 g of cyclohexane dimethanol and 1.12 g of butyltin tris-2-ethylhexanoate (such that there will be 200 ppm tin metal in the final polymer). The heating mantle was set manually to 100% output. The set points and data collection were facilitated by a Camile process control system. Once the reactants were melted, stirring was initiated and slowly increased to 250 rpm. The temperature of the reactor gradually increased with run time. The weight of methanol collected was recorded via balance. The reaction was stopped when methanol evolution stopped or at a pre-selected lower temperature of 260° C. The oligomer was discharged with a nitrogen purge and cooled to room temperature. The oligomer was frozen with liquid nitrogen and broken into pieces small enough to be weighed into a 500 ml round bottom flask.

In the polycondensation reactions, a 500 ml round bottom flask was charged with 150 g of the oligomer prepared above. The flask was equipped with a stainless steel stirrer and polymer head. The glassware was set up on a half mole polymer rig and the Camile sequence was initiated. The stirrer was positioned one full turn from the flask bottom once the oligomer melted. The temperature/pressure/stir rate sequence controlled by the Camile software for these examples is reported in the following table, unless otherwise specified below.

Camile Sequence for Polycondensation Reactions

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 290 | 6 | 25 |

Camile Sequence for Examples A and B

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 80 | 290 | 6 | 25 |

For Example C, the same sequence in the preceding table was used, except the time was 50 min in Stage 7.

The resulting polymers were recovered from the flask, chopped using a hydraulic chopper, and ground to a 6 mm screen size. Samples of each ground polymer were submitted for inherent viscosity in 60/40 (wt/wt) phenol/tetrachloroethane at a concentration of 0.5 g/100 ml at 25° C., catalyst level (Sn) by x-ray fluorescence, and color (L*, a*, b*) by transmission spectroscopy. Polymer composition was obtained by 1H NMR. Samples were submitted for thermal stability and melt viscosity testing using a Rheometrics Mechanical Spectrometer (RMS-800).

Examples D to K and M

The polyesters of these examples were prepared as described above for Examples A to C, except that the target tin amount in the final polymer was 150 ppm for examples A D to K and M. The following tables describe the temperature/pressure/stir rate sequences controlled by the Camile software for these examples.

Camile Sequence for Examples D, F, and H

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 400 | 50 |
| 5 | 110 | 290 | 400 | 50 |
| 6 | 5 | 290 | 8 | 50 |
| 7 | 110 | 295 | 8 | 50 |

For Example D, the stirrer was turned to 25 rpm with 95 min left in Stage 7.

Camile Sequence for Example E

| Stage | Time (min) | Temp (° C.) | Vacuum (torr) | Stir (rpm) |
|---|---|---|---|---|
| 1 | 10 | 245 | 760 | 0 |
| 2 | 5 | 245 | 760 | 50 |
| 3 | 30 | 283 | 760 | 50 |
| 4 | 3 | 283 | 175 | 50 |
| 5 | 5 | 283 | 5 | 50 |
| 6 | 5 | 283 | 1.2 | 50 |
| 7 | 71 | 285 | 1.2 | 50 |

For Example K, the same sequence in the preceding table was used, except the time was 75 min in Stage 7.

Camile Sequence for Example G

| Stage | Time (min) | Temp (° C.) | Vacuum (torr) | Stir (rpm) |
|---|---|---|---|---|
| 1 | 10 | 245 | 760 | 0 |
| 2 | 5 | 245 | 760 | 50 |
| 3 | 30 | 285 | 760 | 50 |
| 4 | 3 | 285 | 175 | 50 |
| 5 | 5 | 285 | 5 | 50 |
| 6 | 5 | 285 | 4 | 50 |
| 7 | 220 | 290 | 4 | 50 |

Camile Sequence for Example I

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 285 | 90 | 50 |
| 6 | 5 | 285 | 6 | 50 |
| 7 | 70 | 290 | 6 | 50 |

Camile Sequence for Example J

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 295 | 6 | 25 |

Examples L and K

Dimethyl terephthalate, 1,4-cyclohexanedimethanol, and 2,2,4,4-tetramethyl-1,3-cyclobutanediol were weighed into a 500-ml single neck round bottom flask. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 45 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

The table below shows the experimental data for the polyesters of this example. The data shows that an increase in the level of 2,2,4,4-tetramethyl-1,3-cyclobutanediol raises the glass transition temperature in an almost linear fashion, for a constant inherent viscosity. FIG. 3 also shows the dependence of Tg on composition and inherent viscosity.

TABLE 9

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 44.2 | 36.4 | 0.49 | 118 | NA | NA | NA |
| B | 44.3 | 36.3 | 0.51 | 119 | NA | NA | NA |
| C | 44.4 | 35.6 | 0.55 | 118 | NA | NA | NA |
| D | 46.3 | 52.4 | 0.52 | NA | NA | NA | NA |
| E | 45.7 | 50.9 | 0.54 | NA | NA | NA | NA |
| F | 46.3 | 52.6 | 0.56 | NA | NA | NA | NA |
| G | 46 | 50.6 | 0.56 | NA | NA | NA | NA |
| H | 46.5 | 51.8 | 0.57 | NA | NA | NA | NA |
| I | 45.6 | 51.2 | 0.58 | NA | NA | NA | NA |
| J | 46 | 51.9 | 0.58 | NA | NA | NA | NA |
| K | 45.5 | 51.2 | 0.59 | NA | NA | NA | NA |
| L | 46.1 | 49.6 | 0.383 | 117 | NA | NA | 387 |

TABLE 9-continued

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| K | 45.6 | 50.5 | 0.325 | 108 | NA | NA | NA |
| M | 47.2 | NA | 0.48 | NA | NA | NA | NA |

NA = Not available

Example 10

This example illustrates the effect of the predominance of the type of 2,2,4,4-tetramethyl-1,3-cyclobutanediol isomer (cis or trans) on the glass transition temperature of the polyester.

Dimethyl terephthalate, 1,4-cyclohexanedimethanol, and 2,2,4,4-tetramethyl-1,3-cyclobutanediol were weighed into a 500-ml single neck round bottom flask. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 45 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

The table below shows the experimental data for the polyesters of this Example. The data shows that cis 2,2,4,4-tetramethyl-1,3-cyclobutanediol is approximately twice as effective as trans 2,2,4,4-tetramethyl-1,3-cyclobutanediol at increasing the glass transition temperature for a constant inherent viscosity.

TABLE 10

Effect of 2,2,4,4-tetramethyl-1,3-cyclobutanediol cis/trans composition on $T_g$

| Example | mol % TMCD | IV (dL/g) | $T_g$ (° C.) | $\eta_o$ at 260° C. (Poise) | $\eta_o$ at 275° C. (Poise) | $\eta_o$ at 290° C. (Poise) | % cis TMCD |
|---|---|---|---|---|---|---|---|
| A | 45.8 | 0.71 | 119 | N.A. | N.A. | N.A. | 4.1 |
| B | 43.2 | 0.72 | 122 | N.A. | N.A. | N.A. | 22.0 |
| C | 46.8 | 0.57 | 119 | 26306 | 16941 | 6601 | 22.8 |
| D | 43.0 | 0.67 | 125 | 55060 | 36747 | 14410 | 23.8 |
| E | 43.8 | 0.72 | 127 | 101000 | 62750 | 25330 | 24.5 |
| F | 45.9 | 0.533 | 119 | 11474 | 6864 | 2806 | 26.4 |
| G | 45.0 | 0.35 | 107 | N.A. | N.A. | N.A. | 27.2 |
| H | 41.2 | 0.38 | 106 | 1214 | 757 | N.A. | 29.0 |
| I | 44.7 | 0.59 | 123 | N.A. | N.A. | N.A. | 35.4 |
| J | 44.4 | 0.55 | 118 | N.A. | N.A | N.A. | 35.6 |
| K | 44.3 | 0.51 | 119 | N.A. | N.A. | N.A. | 36.3 |
| L | 44.0 | 0.49 | 128 | N.A. | N.A. | N.A. | 71.7 |
| M | 43.6 | 0.52 | 128 | N.A. | N.A. | N.A. | 72.1 |
| N | 43.6 | 0.54 | 127 | N.A. | N.A. | N.A. | 72.3 |
| O | 41.5 | 0.58 | 133 | 15419 | 10253 | 4252 | 88.7 |
| P | 43.8 | 0.57 | 135 | 16219 | 10226 | 4235 | 89.6 |
| Q | 41.0 | 0.33 | 120 | 521 | 351 | 2261 | 90.4 |
| R | 43.0 | 0.56 | 134 | N.A. | N.A. | N.A. | 90.6 |
| S | 43.0 | 0.49 | 132 | 7055 | 4620 | 2120 | 90.6 |
| T | 43.1 | 0.55 | 134 | 12970 | 8443 | 3531 | 91.2 |
| U | 45.9 | 0.52 | 137 | N.A. | N.A. | N.A. | 98.1 |

NA = not available

Example 11—Comparative Example

This example illustrates that a polyester based on 100% 2,2,4,4-tetramethyl-1,3-cyclobutanediol has a slow crystallization half-time.

A polyester based solely on terephthalic acid and 2,2,4,4-tetramethyl-1,3-cyclobutanediol was prepared in a method similar to the method described in Example 1A with the properties shown on Table 11. This polyester was made with 300 ppm dibutyl tin oxide. The trans/cis ratio of the 2,2,4,4-tetramethyl-1,3-cyclobutanediol was 65/35.

Films were pressed from the ground polymer at 320° C. Crystallization half-time measurements from the melt were made at temperatures from 220 to 250° C. at 10° C. increments and are reported in Table 11. The fastest crystallization half-time for the sample was taken as the minimum value of crystallization half-time as a function of temperature. The fastest crystallization half-time of this polyester is around 1300 minutes. This value contrasts with the fact that the polyester (PCT) based solely on terephthalic acid and 1,4-cyclohexanedimethanol (no comonomer modification) has an extremely short crystallization half-time (<1 min) as shown in FIG. 1.

TABLE 11

Crystallization Half-times (min)

| Comonomer (mol %) | IV (dl/g) | $T_g$ (° C.) | $T_{max}$ (° C.) | at 220° C. (min) | at 230° C. (min) | at 240° C. (min) | at 250° C. (min) |
|---|---|---|---|---|---|---|---|
| 100 mol % F | 0.63 | 170.0 | 330 | 3291 | 3066 | 1303 | 1888 | where:
F is 2,2,4,4-Tetramethyl-1,3-cyclobutanediol (65/35 Trans/Cis)

Example 12

Sheets comprising a polyester that had been prepared with a target composition of 100 mole % terephthalic acid residues, 80 mole % 1,4-cyclohexanedimethanol residues, and 20 mole % 2,2,4,4-tetramethyl-1,3-cyclobutanediol residues were produced using a 3.5 inch single screw extruder. A sheet was extruded continuously, gauged to a thickness of 177 mil and then various sheets were sheared to size. Inherent viscosity and glass transition temperature were measured on one sheet. The sheet inherent viscosity was measured to be 0.69 dl/g. The glass transition temperature of the sheet was measured to be 106° C. Sheets were then conditioned at 50% relative humidity and 60° C. for 2 weeks. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example G). The thermoformed part was visually inspected for any blisters and the degree of blistering rated as none (N), low (L), or high (H). The results below demonstrate that these thermoplastic sheets with a glass transition temperature of 106° C. can be thermoformed under the conditions shown below, as evidenced by these sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 86 | 145 | 501 | 64 | N |
| B | 100 | 150 | 500 | 63 | N |
| C | 118 | 156 | 672 | 85 | N |
| D | 135 | 163 | 736 | 94 | N |
| E | 143 | 166 | 760 | 97 | N |
| F | 150 | 168 | 740 | 94 | L |
| G | 159 | 172 | 787 | 100 | L |

Example 13

Sheets comprising a polyester that had been prepared with a target composition of 100 mole % terephthalic acid residues, 80 mole % 1,4-cyclohexanedimethanol residues, and 20 mole % 2,2,4,4-tetramethyl-1,3-cyclobutanediol residues were produced using a 3.5 inch single screw. A sheet was extruded continuously, gauged to a thickness of 177 mil and then various sheets were sheared to size. Inherent viscosity and glass transition temperature were measured on one sheet. The sheet inherent viscosity was measured to be 0.69 dl/g. The glass transition temperature of the sheet was measured to be 106° C. Sheets were then conditioned at 100% relative humidity and 25° C. for 2 weeks. Sheets were subsequently thermoformed into a female mold having a draw ratio of 2.5:1 using a Brown thermoforming machine. The thermoforming oven heaters were set to 60/40/40% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example G). The thermoformed part was visually inspected for any blisters and the degree of blistering rated as none (N), low (L), or high (H). The results below demonstrate that these thermoplastic sheets with a glass transition temperature of 106° C. can be thermoformed under the conditions shown below, as evidenced by the production of sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 141 | 154 | 394 | 53 | N |
| B | 163 | 157 | 606 | 82 | N |
| C | 185 | 160 | 702 | 95 | N |
| D | 195 | 161 | 698 | 95 | N |
| E | 215 | 163 | 699 | 95 | L |
| F | 230 | 168 | 705 | 96 | L |
| G | 274 | 174 | 737 | 100 | H |
| H | 275 | 181 | 726 | 99 | H |

Example 14—Comparative Example

Sheets consisting of Kelvx 201 were produced using a 3.5 inch single screw extruder. Kelvx is a blend consisting of 69.85% PCTG (Eastar from Eastman Chemical Co. having 100 mole % terephthalic acid residues, 62 mole % 1,4-cyclohexanedimethanol residues, and 38 mole % ethylene glycol residues); 30% PC (bisphenol A polycarbonate); and 0.15% Weston 619 (stabilizer sold by Crompton Corporation). A sheet was extruded continuously, gauged to a thickness of 177 mil and then various sheets were sheared to size. The glass transition temperature was measured on one sheet and was 100° C. Sheets were then conditioned at 50% relative humidity and 60° C. for 2 weeks. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example E). The thermoformed part was visually inspected for any blisters and the degree of blistering rated as none (N), low (L), or high (H). The results below demonstrate that these thermoplastic sheets with a glass transition temperature of 100° C. can be thermoformed under the conditions shown below, as evidenced by the production of sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 90 | 146 | 582 | 75 | N |
| B | 101 | 150 | 644 | 83 | N |
| C | 111 | 154 | 763 | 98 | N |
| D | 126 | 159 | 733 | 95 | N |
| E | 126 | 159 | 775 | 100 | N |
| F | 141 | 165 | 757 | 98 | N |
| G | 148 | 168 | 760 | 98 | L |

Example 15—Comparative Example

Sheets consisting of Kelvx 201 were produced using a 3.5 inch single screw extruder. A sheet was extruded continuously, gauged to a thickness of 177 mil and then various sheets were sheared to size. The glass transition temperature was measured on one sheet and was 100° C. Sheets were then conditioned at 100% relative humidity and 25° C. for 2 weeks. Sheets were subsequently thermoformed into a female mold having a draw ratio of 2.5:1 using a Brown thermoforming machine. The thermoforming oven heaters were set to 60/40/40% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example H). The thermoformed part was visually inspected for any blisters and the degree of blistering rated as none (N), low (L), or high (H). The results below demonstrate that these thermoplastic sheets with a glass transition temperature of 100° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 110 | 143 | 185 | 25 | N |
| B | 145 | 149 | 529 | 70 | N |
| C | 170 | 154 | 721 | 95 | N |
| D | 175 | 156 | 725 | 96 | N |
| E | 185 | 157 | 728 | 96 | N |
| F | 206 | 160 | 743 | 98 | L |
| G | 253 | NR | 742 | 98 | H |
| H | 261 | 166 | 756 | 100 | H |

NR = Not recorded

Example 16—Comparative Example

Sheets consisting of PCTG 25976 (100 mole % terephthalic acid residues, 62 mole % 1,4-cyclohexanedimethanol residues, and 38 mole % ethylene glycol residues) were produced using a 3.5 inch single screw extruder. A sheet was extruded continuously, gauged to a thickness of 118 mil and then various sheets were sheared to size. The glass transition temperature was measured on one sheet and was 87° C. Sheets were then conditioned at 50% relative humidity and 60° C. for 4 weeks. The moisture level was measured to be 0.17 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 87° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 102 | 183 | 816 | 100 | N |
| B | 92 | 171 | 811 | 99 | N |

-continued

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| C | 77 | 160 | 805 | 99 | N |
| D | 68 | 149 | 804 | 99 | N |
| E | 55 | 143 | 790 | 97 | N |
| F | 57 | 138 | 697 | 85 | N |

Example 17—Comparative Example

A miscible blend consisting of 20 wt % Teijin L-1250 polycarbonate (a bisphenol-A polycarbonate), 79.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 94° C. Sheets were then conditioned at 50% relative humidity and 60° C. for 4 weeks. The moisture level was measured to be 0.25 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 94° C. can be thermoformed under the conditions shown below, as evidenced by the production of sheets having greater than 95% draw and no blistering, without predrying the sheets prior to thermoforming.

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| A | 92 | 184 | 844 | 100 | H |
| B | 86 | 171 | 838 | 99 | N |
| C | 73 | 160 | 834 | 99 | N |
| D | 58 | 143 | 787 | 93 | N |
| E | 55 | 143 | 665 | 79 | N |

Example 18—Comparative Example

A miscible blend consisting of 30 wt % Teijin L-1250 polycarbonate, 69.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 99° C. Sheets were then conditioned at 50% relative humidity and 60° C. for 4 weeks. The moisture level was measured to be 0.25 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 99° C. can be thermoformed under the conditions shown below, as evidenced by the production of sheets having greater than 95% draw and no blistering, without predrying the sheets prior to thermoforming.

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| A | 128 | 194 | 854 | 100 | H |
| B | 98 | 182 | 831 | 97 | L |
| C | 79 | 160 | 821 | 96 | N |
| D | 71 | 149 | 819 | 96 | N |
| E | 55 | 145 | 785 | 92 | N |
| F | 46 | 143 | 0 | 0 | NA |
| G | 36 | 132 | 0 | 0 | NA |

NA = not applicable.
A value of zero indicates that the sheet was not formed because it did not pull into the mold (likely because it was too cold).

Example 19—Comparative Example

A miscible blend consisting of 40 wt % Teijin L-1250 polycarbonate, 59.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 105° C. Sheets were then conditioned at 50% relative humidity and 60° C. for 4 weeks. The moisture level was measured to be 0.265 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples 8A to 8E). The thermoformed part was visually inspected for any blisters and the degree of blistering rated as none (N), low (L), or high (H). The results below demonstrate that these thermoplastic sheets with a glass transition temperature of 105° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 111 | 191 | 828 | 100 | H |
| B | 104 | 182 | 828 | 100 | H |
| C | 99 | 179 | 827 | 100 | N |
| D | 97 | 177 | 827 | 100 | N |
| E | 78 | 160 | 826 | 100 | N |
| F | 68 | 149 | 759 | 92 | N |
| G | 65 | 143 | 606 | 73 | N |

Example 20—Comparative Example

A miscible blend consisting of 50 wt % Teijin L-1250 polycarbonate, 49.85 wt % PCTG 25976, and 0.15 wt % Weston 619 was produced using a 1.25 inch single screw extruder. A sheet was extruded continuously, gauged to a thickness of 118 mil and then various sheets were sheared to size. The glass transition temperature was measured on one sheet and was 111° C. Sheets were then conditioned at 50% relative humidity and 60° C. for 4 weeks. The moisture level was measured to be 0.225 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples A to D). The thermoformed part was visually inspected for any blisters and the degree of blistering rated as none (N), low (L), or high (H). The results below demonstrate that these thermoplastic sheets with a glass transition temperature of 111° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 118 | 192 | 815 | 100 | H |
| B | 99 | 182 | 815 | 100 | H |
| C | 97 | 177 | 814 | 100 | L |
| D | 87 | 171 | 813 | 100 | N |
| E | 80 | 160 | 802 | 98 | N |
| F | 64 | 154 | 739 | 91 | N |
| G | 60 | 149 | 0 | 0 | NA |

NA = not applicable.
A value of zero indicates that the sheet was not formed because it did not pull into the mold (likely because it was too cold).

Example 21—Comparative Example

A miscible blend consisting of 60 wt % Teijin L-1250 polycarbonate, 39.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 117° C. Sheets were then conditioned at 50% relative humidity and 60° C. for 4 weeks. The moisture level was measured to be 0.215 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 117° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 114 | 196 | 813 | 100 | H |
| B | 100 | 182 | 804 | 99 | H |
| C | 99 | 177 | 801 | 98 | L |
| D | 92 | 171 | 784 | 96 | L |
| E | 82 | 168 | 727 | 89 | L |
| F | 87 | 166 | 597 | 73 | N |

Example 22—Comparative Example

A miscible blend consisting of 65 wt % Teijin L-1250 polycarbonate, 34.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 120° C. Sheets were then conditioned at 50% relative humidity and 60° C. for 4 weeks. The moisture level was measured to be 0.23 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 120° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 120 | 197 | 825 | 100 | H |
| B | 101 | 177 | 820 | 99 | H |
| C | 95 | 174 | 781 | 95 | L |
| D | 85 | 171 | 727 | 88 | L |
| E | 83 | 166 | 558 | 68 | L |

Example 23—Comparative Example

A miscible blend consisting of 70 wt % Teijin L-1250 polycarbonate, 29.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 123° C. Sheets were then conditioned at 50% relative humidity and 60° C. for 4 weeks. The moisture level was measured to be 0.205 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples A and B). The thermoformed part was visually inspected for any blisters and the degree of blistering rated as none (N), low (L), or high (H). The results below demonstrate that these thermoplastic sheets with a glass transition temperature of 123° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 126 | 198 | 826 | 100 | H |
| B | 111 | 188 | 822 | 100 | H |
| C | 97 | 177 | 787 | 95 | L |
| D | 74 | 166 | 161 | 19 | L |
| E | 58 | 154 | 0 | 0 | NA |
| F | 48 | 149 | 0 | 0 | NA |

NA = not applicable.
A value of zero indicates that the sheet was not formed because it did not pull into the mold (likely because it was too cold).

Example 24—Comparative Example

Sheets consisting of Teijin L-1250 polycarbonate were produced using a 3.5 inch single screw extruder. A sheet was extruded continuously, gauged to a thickness of 118 mil and then various sheets were sheared to size. The glass transition temperature was measured on one sheet and was 149° C. Sheets were then conditioned at 50% relative humidity and 60° C. for 4 weeks. The moisture level was measured to be 0.16 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 149° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 152 | 216 | 820 | 100 | H |
| B | 123 | 193 | 805 | 98 | H |
| C | 113 | 191 | 179 | 22 | H |
| D | 106 | 188 | 0 | 0 | H |
| E | 95 | 182 | 0 | 0 | NA |
| F | 90 | 171 | 0 | 0 | NA |

NA = not applicable.
A value of zero indicates that the sheet was not formed because it did not pull into the mold (likely because it was too cold).

It can be clearly seen from a comparison of the data in the above relevant working examples that the polyesters of the present invention offer a definite advantage over the commercially available polyesters with regard to glass transition temperature, density, slow crystallization rate, melt viscosity, and toughness.

The invention has been described in detail with particular reference to preferred embodiments thereof, but it will be understood that variations and modifications can be effected within the spirit and scope of the invention.

We claim:

1. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:
   (1) 1 to 100 weight % of a polyester comprising:
      (a) a dicarboxylic acid component comprising:
         i) from about 70 to 100 mole % of terephthalic acid residues;
         ii) 0 to about 30 mole % of an aromatic dicarboxylic acid residues having up to 20 carbon atoms; and
         iii) 0 to about 10 mole % of an aliphatic dicarboxylic acid residues having up to 16 carbon atoms; and
      (b) a glycol component comprising:
         i) about 1 to about 99 mole % of 2,2,4,4-tetramethyl-1,3-cyclobutanediol residues;
         ii) about 1 to about 99 mole % of 1,4-cyclohexanedimethanol residues; and
         iii) substantially no ethylene glycol residues,
      wherein the total mole % of the dicarboxylic acid component is 100 mole %, and the total mole % of the glycol component is 100 mole %; and
      wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.; and
   (2) 99 to 0 weight % of an aromatic polycarbonate;
      wherein the total combined weight percentage of the polyester and the polycarbonate in the polyester-containing composition equals 100 weight %.

2. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:
   (1) 1 to 100 weight % of a polyester comprising:
      (a) a dicarboxylic acid component comprising:
         i) from about 70 to 100 mole % of terephthalic acid residues;
         ii) 0 to about 30 mole % of an aromatic dicarboxylic acid residues having up to 20 carbon atoms; and
         iii) 0 to about 10 mole % of an aliphatic dicarboxylic acid residues having up to 16 carbon atoms; and
      (b) a glycol component comprising:
         i) 21 to 99 mole % of 2,2,4,4-tetramethyl-1,3-cyclobutanediol residues;
         ii) about 1 to less than 79 mole % of 1,4-cyclohexanedimethanol residues; and
         iii) substantially no ethylene glycol residues,
      wherein the total mole % of the dicarboxylic acid component is 100 mole %, and the total mole % of the glycol component is 100 mole %; and
      wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.; and
   (2) 99 to 0 weight % of an aromatic polycarbonate;
      wherein the total combined weight percentage of the polyester and the polycarbonate in the polyester-containing composition equals 100 weight %.

3. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:
   (1) 1 to 100 weight % of a polyester comprising:
      (a) a dicarboxylic acid component comprising:
         i) from about 70 to 100 mole % of terephthalic acid residues;
         ii) 0 to about 30 mole % of an aromatic dicarboxylic acid residues having up to 20 carbon atoms; and
         iii) 0 to about 10 mole % of an aliphatic dicarboxylic acid residues having up to 16 carbon atoms; and
      (b) a glycol component comprising:
         i) about 25 to 75 mole % of 2,2,4,4-tetramethyl-1,3-cyclobutanediol residues; and
         ii) about 75 to about 25 mole % of 1,4-cyclohexanedimethanol residues,
      wherein the total mole % of the dicarboxylic acid component is 100 mole %, and the total mole % of the glycol component is 100 mole %; and
      wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.;and
   (2) 99 to 0 weight % of an aromatic polycarbonate;
      wherein the total combined weight percentage of the polyester and the polycarbonate in the polyester-containing composition equals 100 weight %.

4. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:
   (1) 1 to 100 weight % of a polyester comprising:
      (a) a dicarboxylic acid component comprising:
         i) from about 70 to 100 mole % of terephthalic acid residues;
         ii) 0 to about 30 mole % of an aromatic dicarboxylic acid residues having up to 20 carbon atoms; and
         iii) 0 to about 10 mole % of an aliphatic dicarboxylic acid residues having up to 16 carbon atoms; and
      (b) a glycol component comprising:
         i) about 30 to about 70 mole % of 2,2,4,4-tetramethyl-1,3-cyclobutanediol residues; and
         ii) about 70 to about 30 mole % of 1,4-cyclohexanedimethanol residues,
      wherein the total mole % of the dicarboxylic acid component is 100 mole %, and the total mole % of the glycol component is 100 mole %; and
      wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.; and (2) 99 to 0 weight % of an aromatic polycarbonate;
wherein the total combined weight percentage of the polyester and the polycarbonate in the polyester-containing composition equals 100 weight %.

5. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:

(1) 1 to 100 weight % of a polyester comprising:
  (a) a dicarboxylic acid component comprising:
    i) from about 70 to 100 mole % of terephthalic acid residues;
    ii) 0 to about 30 mole % of an aromatic dicarboxylic acid residues having up to 20 carbon atoms; and
    iii) 0 to about 10 mole % of an aliphatic dicarboxylic acid residues having up to 16 carbon atoms; and
  (b) a glycol component comprising:
    i) about 35 to about 65 mole % of 2,2,4,4-tetramethyl-1,3-cyclobutanediol residues; and
    ii) about 65 to about 35 mole % of 1,4-cyclohexanedimethanol residues,
  wherein the total mole % of the dicarboxylic acid component is 100 mole %, and the total mole % of the glycol component is 100 mole %; and
  wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.; and (2) 99 to 0 weight % of an aromatic polycarbonate;
wherein the total combined weight percentage of the polyester and the polycarbonate in the polyester-containing composition equals 100 weight %.

6. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:

(1) 1 to 100 weight % of a polyester comprising:
  (a) a dicarboxylic acid component comprising:
    i) from about 70 to 100 mole % of terephthalic acid residues;
    ii) 0 to about 30 mole % of an aromatic dicarboxylic acid residues having up to 20 carbon atoms; and
    iii) 0 to about 10 mole % of an aliphatic dicarboxylic acid residues having up to 16 carbon atoms; and
  (b) a glycol component comprising:
    i) about 40 to about 69 mole % of 2,2,4,4-tetramethyl-1,3-cyclobutanediol residues; and
    ii) about 40 to about 60 mole % of 1,4-cyclohexanedimethanol residues,
  wherein the total mole % of the dicarboxylic acid component is 100 mole %, and the total mole % of the glycol component is 100 mole %; and
  wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.; and (2) 99 to 0 weight % of an aromatic polycarbonate;
wherein the total combined weight percentage of the polyester and the polycarbonate in the polyester-containing composition equals 100 weight %.

7. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:

(1) 1 to 100 weight % of a polyester comprising:
  (a) a dicarboxylic acid component comprising:
    i) from about 70 to 100 mole % of terephthalic acid residues;
    ii) 0 to about 30 mole % of an aromatic dicarboxylic acid residues having up to 20 carbon atoms; and
    iii) 0 to about 10 mole % of an aliphatic dicarboxylic acid residues having up to 16 carbon atoms; and
  b) a glycol component consisting essentially of:
    i) about 1 to about 99 mole % of 2,2,4,4-tetramethyl-1,3cyclobutanediol residues;
    ii) about 1 to about 99 mole % of 1,4-cyclohexanedimethanol residues; and
  wherein the total mole % of the dicarboxylic acid component is 100 mole %, and the total mole % of the glycol component is 100 mole %; and
  wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.; and (2) 99 to 0 weight % of an aromatic polycarbonate;
wherein the total combined weight percentage of the polyester and the polycarbonate in the polyester-containing composition equals 100 weight %.

8. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:

(1) 1 to 100 weight % of a polyester comprising:
  (a) a dicarboxylic acid component comprising:
    i) from about 70 to 100 mole % of terephthalic acid residues;
    ii) 0 to about 30 mole % of an aromatic dicarboxylic acid residues having up to 20 carbon atoms; and
    iii) 0 to about 10 mole % of an aliphatic dicarboxylic acid residues having up to 16 carbon atoms; and
  (b) a glycol component comprising:
    i) greater than 20 to less than 50 mole % of 2,2,4,4-tetramethyl-1,3-cyclobutanediol residues; and
    ii) greater than 50 to less than 80 mole % of 1,4-cyclohexanedimethanol residues;
    iii) less than 15 mole % ethylene glycol residues,
  wherein the combination of the 1,4-cyclohexanedimethanol residues and the ethylene glycol residues constitute less than 78 mole % of the glycol component,
  wherein the total mole % of the dicarboxylic acid component is 100 mole %, and the total mole % of the glycol component is 100 mole %; and
  wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.;and (2) 99 to 0 weight % of an aromatic polycarbonate;
wherein the total combined weight percentage of the polyester and the polycarbonate in the polyester-containing composition equals 100 weight %.

9. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:

(1) 1 to 100 weight % of a polyester comprising:
 (a) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and
 (b) a glycol component comprising:
  i) about 1 to about 99 mole % of 2,2,4,4-tetramethyl-1,3-cyclobutanediol residues; and
  ii) about 1 to less than about 99 mole % of 1,4-cyclohexanedimethanol residues,
wherein said 2,2,4,4-tetramethyl-1,3-cyclobutanediol residues are a mixture comprising greater than 55 mole % of cis-2,2,4,4-tetramethyl-1,3-cyclobutanediol and less than 45 mole % of trans-2,2,4,4-tetramethyl-1,3-cyclobutanediol,
wherein the total mole % of the dicarboxylic acid component is 100 mole %, and the total mole % of the glycol component is 100 mole %; and
wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 110 to 200° C.; and (2) 99 to 0 weight % of an aromatic polycarbonate; wherein the total combined weight percentage of the polyester and the polycarbonate in the polyester-containing composition equals 100 weight %.

10. A thermoplastic article having one or more decorative materials embedded therein obtained by applying heat and pressure to one or more laminates wherein at least one of said laminates comprises, in order, (1) an upper sheet material; (2) one or more decorative materials; and (3) a lower sheet material; wherein the upper and lower sheet materials are formed from a polyester-containing composition comprising:

(1) 1 to 100 weight % of a polyester comprising:
 (a) a dicarboxylic acid component comprising:
  i) from about 70 to 100 mole % of terephthalic acid residues;
  ii) 0 to about 30 mole % of an aromatic dicarboxylic acid residues having up to 20 carbon atoms; and
  iii) 0 to about 10 mole % of an aliphatic dicarboxylic acid residues having up to 16 carbon atoms; and
 (b) a glycol component comprising:
  i) about 1 to about 99 mole % of 2,2,4,4-tetramethyl-1,3-cyclobutanediol residues;
  ii) about 1 to about 99 mole % of 1,4-cyclohexanedimethanol residues;
  iii) less than 15 mole % ethylene glycol residues,
wherein the combination of the 1,4-cyclohexanedimethanol residues and the ethylene glycol residues constitute less than 78 mole % of the glycol component,
wherein the total mole % of the dicarboxylic acid component is 100 mole %, and the total mole % of the glycol component is 100 mole %; and
wherein the inherent viscosity of the polyester is from about 0.5 to 1.2 dL/g as determined in 60/40 (wt/wt) phenol/tetrachloroethane at a concentration of 0.5 g/100 ml at 25° C.; and wherein the polyester has a Tg of from about 90 to 200° C.; and (2) 99 to 0 weight % of an aromatic polycarbonate;
wherein the total combined weight percentage of the polyester and the polycarbonate in the polyester-containing composition equals 100 weight %.

11. The thermoplastic article of claim 10 wherein the polyester-containing composition comprises said polyester in the amount of 50 to 90 weight % and said aromatic polycarbonate in the amount of 50 to 10 weight %.

12. The thermoplastic article of claim 10 wherein the polyester-containing composition comprises said polyester in the amount of 60 to 80 weight % and said aromatic polycarbonate in the amount of 40 to 20 weight %.

13. The thermoplastic article of claim 10 wherein said aromatic diacid residue or aliphatic diacid residue of said polyester is selected from the group consisting of the following acids: malonic, succinic, glutaric, adipic, pimelic, suberic, azelaic, sebacic, dodecanedioic, 1,4-, 1,5-, and 2,6-decahydronaphthalenedicarboxylic acid, and cis- or trans-1,4-cyclohexanedicarboxylic acid, isophthalic acid, 4,4'-biphenyldicarboxylic, trans 3,3'-and trans 4,4 stilbenedicarboxylic, 4,4'-dibenzyldicarboxylic, and 1,4-, 1,5'-, 2,3-, 2,6, and 2,7-naphthalenedicarboxylic.

14. The thermoplastic article of claim 10 wherein said polyester comprises branching agents selected from polyfunctional acids, polyfunctional glycols and acid/glycol hybrids.

15. The thermoplastic article of claim 14 wherein said branching agents are selected from the group consisting of trimesic acid, pyromeflitic acid trimellitic anhydride, pyromellitic anhydride, trimethylolpropane, dimethyl hydroxyl terephthalate, and pentaerythritol.

16. The thermoplastic article of claim 10 wherein said aromatic polycarbonate is produced from the reaction of one or more dihydric phenols with a carbonate precursor.

17. The thermoplastic article of claim 16 wherein said dihydric phenol is selected from the group consisting of 2,2-bis-(4-hydroxyphenyl)-propane), 3,3,5-trimethyl-1,1 -bis(4-hydroxyphenyl)-cyclohexane, 2,4-bis-(4-hydroxyphenyl)-2-methyl-butane, 1,1 -bis-(4-hydroxyphenyl)-cyclohexane, alpha,alpha'-bis-(4-hydroxyphenyl)-p-diisopropylbenzene, 2,2-bis-(3-methyl4-hydroxyphenyl)-propane, 2,2-bis-(3-chloro-4-hydroxyphenyl)propane, bis-(3,5-dimethyl4-hydroxyphenyl)-methane, 2,2-bis-(3,5-dimethyl-4-hydroxyphenyl)-propane, bis-(3,5-dimethyl-4-hydroxyphenyl)-sulfide, bis-(3,5dimethyl-4-hydroxyphenyl)-sulfoxide, bis-(3,5dimethyl-4-hydroxyphenyl)-sulfone dihydroxybenzophenone, 2,4-bis-(3,5-dimethyl-4-hydroxyphenyl)-cyclohexane, alpha, alpha'-bis-(3,5-dimethyl-4-hydroxyphenyl)-p-diisopropylbenzene and 4,4'-sulfonyl diphenol, hydroquinone, resorcinol, bis-(hydroxyphenyl)-alkanes, bis-(hydroxyphenyl)ethers, bis-(hydroxyphenyl)-ketones, bis-(hydroxyphenyl)-sulfoxides, bis-(hydroxyphenyl)-sulfides, bis-(hydroxyphenyl)-sulfones, and alpha, alpha-bis-(hydroxyphenyl)diisopropylbenzenes.

18. The thermoplastic particle of claim 17 wherein said dihydric phenol is 2,2-bis-(4-hydroxyphenyl)-propane.

19. The thermoplastic article of claim 16 wherein said carbonate precursor is selected from the group consisting of a carbonyl halide, a diarylcarbonate, and a bishaloformate.

20. The thermoplastic article of claim 19 wherein said carbonyl halide is selected from the group consisting of carbonyl bromide, carbonyl chloride, and mixtures thereof.

21. The thermoplastic article of claim 19 wherein said bishaloformates are selected from the group consisting of bischloroformates of 2,2-bis(4-hydroxyphenyl)-propane, hydroquinone, and the like and bishaloformates of glycol.

22. The thermoplastic article of claim 19 wherein said carbonyl halide is carbonyl chloride.

23. The thermoplastic article of claim 19 wherein said diarylcarbonate is diphenyl carbonate.

24. The thermoplastic article of claim 10 wherein said polycarbonate comprises one or more branching agents selected from the group consisting of tri- and tetrafunctional phenols, carbonic acids, and bisphenols with carbonic acid side chains.

25. The thermoplastic article of claim 10 wherein said polycarbonate comprises one or more branching agents selected from 1,4-bis(4',4''-dihydroxytriphenylmethyl) benzene, and trisphenol TC.

26. The thermoplastic article of claim 10 wherein said polycarbonate comprises nitrogen-containing branching agents.

27. The thermoplastic article of claim 10 wherein said polycarbonate comprises one or more branching agents selected from the group consisting of cyanic chloride and 3,3-bis(4-hydroxyphenyl)-2-oxo-2,3-dihydroindole.

28. The thermoplastic article of claim 10 wherein said polyester-containing composition comprises one or more additives selected from the group consisting of impact modifiers, UV stabilizers, phosphorous stabilizers, nucleating agents, extenders, flame retarding agents, reinforcing agents, fillers, antistatic agents, mold release agents, colorants, antioxidants, extrusion aids, slip agents, release agents, carbon black, and other pigments.

29. The thermoplastic article of claim 10 wherein said decorative material is selected from the group consisting of selected from the group consisting of metallic wire, rods or bars; natural fibers, glass fibers, mineral fibers, fabric, papers; and printed layers, wood, stone, photographic images, wood chips, grasses, vegetation, thatch, flowers, flower petals, wheat, grains, and crushed glass.

30. The thermoplastic article of claim 10 wherein the upper and lower sheet materials have a thickness in the range of 0.76 to 6.4 mm and the thickness of said decorative material is in the range of 0.0254 mm to 5.08 mm.

31. The thermoplastic article of claim 10 wherein the article includes an abrasion-resistant coating on one or both of the outside surfaces of the article.

32. The thermoplastic article of claim 31 wherein the abrasion resistant coating is provided as a film having a thickness in the range of 0.0127 to 0.254 mm.

33. The thermoplastic article of claim 31 wherein the abrasion resistant film is provided as a fluorinated hydrocarbon, poly(perfluoroethylene), acrylic or oriented poly(ethylene terephthalate) film having a thickness in the range of 0.017 to 0.254 mm.

34. The thermoplastic article of claim 31 wherein the abrasion resistant coating is a heat-, ultraviolet- or electron beam-cured material on a film of poly(vinyl chloride), PETG copolyesters, poly(ethylene terephthalate), poly(methyl methacrylate) or polycarbonate.

35. The thermoplastic article of claim 31 wherein the abrasion resistant coating is a heat-cured silicone, polyurethane or fluorinated polyurethane or an ultraviolet- or electron beam-cured material selected from modified acrylates containing polyurethane, fluorinated polyurethane, silicone, epoxy, polyester, polyether or caprolactone residues.

36. The thermoplastic article of claim 10, wherein the inherent viscosity of the polyester is from 0.6 to 1.2 dL/g.

37. The thermoplastic article of claim 10, wherein the inherent viscosity of the polyester is from 0.6 to 1.1 dL/g.

38. The thermoplastic article of claim 10, wherein the inherent viscosity of the polyester is from 0.6 to 1.0 dL/g.

39. The thermoplastic article of claim 10, wherein the inherent viscosity of the polyester is from 0.60 to 0.9 dL/g.

40. The thermoplastic article of claim 10, wherein the inherent viscosity of the polyester is from 0.60 to 0.8 dL/g.

41. The thermoplastic article of claim 10, wherein the inherent viscosity of the polyester is from 0.60 to 0.7 dL/g.

42. The thermoplastic article of claim 10, wherein the glycol component of the polyester comprises greater than 20 to less than 50 mole % 2,2,4,4-tetramethyl-1,3-cyclobutanediol and greater than 50 to less than 80 mole % 1,4-cyclohexanedimethanol.

43. The thermoplastic article of claim 10, wherein the glycol component of the polyester comprises 10 to 30 mole % 2,2,4,4-tetramethyl-1,3-cyclobutanediol and 70 to 90 mole % 1,4-cyclohexanedimethanol.

44. The thermoplastic article of claim 10, wherein the glycol component of the polyester comprises 15 to 25 mole % 2,2,4,4-tetramethyl-1,3-cyclobutanediol and 75 to 85 mole % 1,4-cyclohexanedimethanol.

45. The thermoplastic article of claim 10, wherein the glycol component of the polyester comprises 17 to 23 mole % 2,2,4,4-tetramethyl-1,3-cyclobutanediol and 77 to 83 mole % 1,4-cyclohexanedimethanol.

46. The thermoplastic article of claim 10, wherein the glycol component of the polyester 21 to less than 50 mole % 2,2,4,4-tetramethyl-1,3-cyclobutanediol and greater than 50 to 79 mole % 1,4-cyclohexanedimethanol.

47. The thermoplastic article of claim 1, wherein the glycol component of the polyester comprises 10 to 30 mole % 2,2,4,4-tetramethyl-1,3cyclobutanediol and 70 to 90 mole % 1,4-cyclohexanedimethanol.

48. The thermoplastic article of claim 1, wherein the glycol component of the polyester comprises 15 to 25 mole % 2,2,4,4-tetramethyl-1,3-cyclobutanediol and 75 to 85 mole % 1,4-cyclohexanedimethanol.

49. The thermoplastic article of claim 1, wherein the glycol component of the polyester comprises 17 to 23 mole % 2,2,4,4-tetramethyl-1,3-cyclobutanediol and 77 to 83 mole % 1,4-cyclohexanedimethanol.

50. The thermoplastic article of claim 10, wherein the polyester has a Tg of 100 to 200° C.

51. The thermoplastic article of claim 10, wherein the polyester has a Tg of 110 to 200° C.

52. The thermoplastic article of claim 10, wherein the polyester has a Tg of 120 to 200° C.

53. The thermoplastic article of claim 10, wherein the dicarboxylic acid component comprises 80 to 100 mole % of terephthalic acid residues.

54. The thermoplastic article of claim 10, wherein the dicarboxylic acid component comprises 90 to 100 mole % of terephthalic acid residues.

55. The thermoplastic article of claim 10, wherein the dicarboxylic acid component comprises 95 to 100 mole % of terephthalic acid residues.

56. The thermoplastic article of claim 10, wherein the dicarboxylic acid component comprises 98 to 100 mole % of terephthalic acid residues.

57. The thermoplastic article of claim 10, wherein the dicarboxylic acid component comprises 99 to 100 mole % of terephthalic acid residues.

58. The thermoplastic article of claim 10, wherein the dicarboxylic acid component comprises 100 mole % of terephthalic acid residues.

59. The thermoplastic article of claim 10, wherein the polyester comprises 1,3-propanediol residues, 1,4-butanediol residues, or mixture thereof.

60. The thermoplastic article of claim 10, wherein the polyester comprises from 0.1 to 25 mole % of 1,3-propanediol residues, 1,4-butanediol residues, or mixture thereof.

61. The thermoplastic article of claim 3, wherein the polyester comprises ethylene glycol residues.

62. The thermoplastic article of claim 10, wherein the polyester comprises from 0.01 to 15 mole % of ethylene glycol residues.

63. The thermoplastic article of claim 10, wherein the 2,2,4,4-tetramethyl-1,3-cyclobutanediol is a mixture comprising greater than 50 mole % of cis-2,2,4,4-tetramethyl-1,3-cyclobutanediol and less than 50 mole % of trans-2,2,4,4-tetramethyl-1,3-cyclobutanediol.

64. The thermoplastic article of claim 7, wherein the 2,2,4,4-tetramethyl-1,3-cyclobutanediol is a mixture comprising greater than 50 mole % of cis-2,2,4,4-tetramethyl-1,3-cyclobutanediol and less than 50 mole % of trans-2,2,4,4-tetramethyl-1,3-cyclobutanediol.

65. The thermoplastic article of claim 10, wherein the polyester-containing composition comprises at least one polymer chosen from poly(etherimides), polyphenylene oxides, poly(phenylene oxide)/polystyrene blends, polystyrene resins, polyphenylene sulfides, polyphenylene sulfide/sulfones, poly (ester-carbonates), polycarbonates, polysulfones; polysulfone ethers, and poly(ether-ketones).

66. The thermoplastic article of claim 10, wherein the polyester-containing composition comprises at least one polycarbonate.

67. The thermoplastic article of claim 2, wherein the polyester comprises residues of at least one branching agent.

68. The thermoplastic article of claim 3, wherein the polyester comprises residues of at least one branching agent an amount of 0.01 to 10 weight % based on the total weight of the polyester.

69. The thermoplastic article of claim 8, wherein the polyester comprises residues of at least one branching agent an amount of 0.01 to 10 weight % based on the total weight of the polyester.

70. The thermoplastic article of claim 9, wherein the polyester comprises residues of at least one branching agent an amount of 0.01 to 10 weight % based on the total weight of the polyester.

71. The thermoplastic article of claim 10, wherein the polyester comprises residues of at least one branching agent an amount of 0.01 to 10 weight % based on the total weight of the polyester.

72. The thermoplastic article of claim 10, wherein the melt viscosity of the polyester is less than 30,000 poise as measured at 1 radian/second on a rotary melt rheometer at 290C.

73. The thermoplastic article of claim 10, wherein the polyester has a crystallization half-time of greater than 1,000 minutes at 170° C.

74. The thermoplastic article of claim 10, wherein the polyester has a crystallization half-time of greater than 10,000 minutes at 170° C.

75. The thermoplastic article of claim 10, wherein the polyester-containing composition has a density of less than 1.2 g/ml at 23° C.

76. The thermoplastic article of claim 2, wherein the polyester-containing composition comprises at least one thermal stabilizer or a reaction product thereof.

77. The thermoplastic article of claim 3, wherein the polyester-containing composition comprises at least one thermal stabilizer or a reaction product thereof.

78. The thermoplastic article of claim 10, wherein the polyester-containing composition comprises at least one thermal stabilizer or a reaction product thereof.

79. The thermoplastic article of claim 10, wherein the yellowness index of the polyester according to ASTM D-1925 is less than 50.

80. The thermoplastic article of claim 10, wherein the polyester has a notched Izod impact strength of at least 3 ft-lbs/in at 23° C. according to ASTM D256 with a 10-mil notch in a ⅛-inch thick bar.

81. The thermoplastic article of claim 10, wherein the polyester has a notched Izod impact strength of at least 10 ft-lbs/in at 23° C. according to ASTM D256 with a 10-mil notch in a ¼-inch thick bar.

82. The thermoplastic article of claim 3, wherein the polyester comprises the residue of at least one catalyst comprising a tin compound or a reaction product thereof.

83. The thermoplastic article of claim 7, wherein the polyester comprises the residue of at least one catalyst comprising a tin compound or a reaction product thereof.

84. The thermoplastic article of claim 9, wherein the polyester comprises the residue of at least one catalyst comprising a tin compound or a reaction product thereof.

85. The thermoplastic article of claim 10, wherein the polyester comprises the residue of at least one catalyst comprising a tin compound or a reaction product thereof.

86. The thermoplastic article of claim 1, wherein the polyester-containing composition includes substantially no polycarbonates.

87. The thermoplastic article of claim 2, wherein the polyester-containing composition includes substantially no polycarbonates.

88. The thermoplastic article of claim 3, wherein the polyester-containing composition includes substantially no polycarbonates.

89. The thermoplastic article of claim 4, wherein the polyester-containing composition includes substantially no polycarbonates.

90. The thermoplastic article of claim 5, wherein the polyester-containing composition includes substantially no polycarbonates.

91. The thermoplastic article of claim 6, wherein the polyester-containing composition includes substantially no polycarbonates.

92. The thermoplastic article of claim 7, wherein the polyester-containing composition includes substantially no polycarbonates.

93. The thermoplastic article of claim 8, wherein the polyester-containing composition includes substantially no polycarbonates.

94. The thermoplastic article of claim 9, wherein the polyester-containing composition includes substantially no polycarbonates.

95. The thermoplastic article of claim 10, wherein the polyester-containing composition includes substantially no polycarbonates.

* * * * *

UNITED STATES PATENT AND TRADEMARK OFFICE
CERTIFICATE OF CORRECTION

PATENT NO. : 7,510,768 B2  
APPLICATION NO. : 11/391642  
DATED : March 31, 2009  
INVENTOR(S) : Crawford et al.

Page 1 of 1

It is certified that error appears in the above-identified patent and that said Letters Patent is hereby corrected as shown below:

Column 97, Line 26, Claim 9 "1 to less than about" should read --1 to about--.

Column 98, Line 42, Claim 15 "pyromeflitic acid trimellitic" should read --pyromellitic acid, trimellitic--.

Column 101, Line 64, Claim 72, "290C." should read --290°C.--.

Signed and Sealed this

Twenty-third Day of June, 2009

JOHN DOLL
*Acting Director of the United States Patent and Trademark Office*